United States Patent
Teng et al.

(10) Patent No.: US 12,263,303 B2
(45) Date of Patent: Apr. 1, 2025

(54) SYSTEMS AND METHODS OF DETECTING INCORRECT CONNECTIONS IN A HUMIDIFICATION SYSTEM

(71) Applicant: Fisher & Paykel Healthcare Limited, Auckland (NZ)

(72) Inventors: Ivan Chih-Fan Teng, Auckland (NZ); Po-Yen Liu, Auckland (NZ); Ho Shing Lo, Auckland (NZ); Oliver Samuel Steiner, Auckland (NZ); Peter Alan Seekup, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 764 days.

(21) Appl. No.: 17/593,928

(22) PCT Filed: Mar. 27, 2020

(86) PCT No.: PCT/NZ2020/050029
§ 371 (c)(1),
(2) Date: Sep. 28, 2021

(87) PCT Pub. No.: WO2020/204731
PCT Pub. Date: Oct. 8, 2020

(65) Prior Publication Data
US 2022/0160977 A1     May 26, 2022

Related U.S. Application Data

(60) Provisional application No. 62/826,801, filed on Mar. 29, 2019.

(51) Int. Cl.
*A61M 16/08*     (2006.01)
*A61M 16/00*     (2006.01)
(Continued)

(52) U.S. Cl.
CPC .... *A61M 16/0051* (2013.01); *A61M 16/0003* (2014.02); *A61M 16/0666* (2013.01);
(Continued)

(58) Field of Classification Search
CPC ............ A61M 16/1085; A61M 16/109; A61M 16/161; A61M 2016/003; A61M 16/0003;
(Continued)

(56) References Cited

U.S. PATENT DOCUMENTS

| | | | |
|---|---|---|---|
| 3,806,102 A * | 4/1974 | Valenta | A61M 16/16 261/DIG. 65 |
| 4,778,017 A | 10/1988 | Liang | |

(Continued)

FOREIGN PATENT DOCUMENTS

| | | |
|---|---|---|
| AU | 2012216775 | 3/2014 |
| AU | 2010206053 | 8/2014 |

(Continued)

OTHER PUBLICATIONS

International Search Report corresponding International Patent Application No. PCT/NZ2020/050029, dated Jul. 21, 2020, in 15 pages.

(Continued)

*Primary Examiner* — Timothy A Stanis
*Assistant Examiner* — Nicholas B. Engel
(74) *Attorney, Agent, or Firm* — Knobbe, Martens, Olson & Bear, LLP

(57) ABSTRACT

Various control methods can indirectly determine incorrect connections between components in a respiratory therapy system. For example, incorrect connections can occur between a patient interface, a humidifier and/or a gases source. The methods can indirectly detect if reverse flow conditions or other error conditions exist. A reverse flow condition can occur when gases flows in a direction different from an intended direction of flow. The methods can be (Continued)

implemented at the humidifier side, at the gases source side, or both.

15 Claims, 50 Drawing Sheets

(51) Int. Cl.
| | |
|---|---|
| A61M 16/06 | (2006.01) |
| A61M 16/10 | (2006.01) |
| A61M 16/16 | (2006.01) |
| A61M 16/20 | (2006.01) |

(52) U.S. Cl.
CPC .... *A61M 16/0833* (2014.02); *A61M 16/0875* (2013.01); *A61M 16/0883* (2014.02); *A61M 16/1085* (2014.02); *A61M 16/109* (2014.02); *A61M 16/161* (2014.02); *A61M 16/202* (2014.02); *A61M 16/208* (2013.01); *A61M 2016/0027* (2013.01); *A61M 2016/003* (2013.01); *A61M 2205/14* (2013.01); *A61M 2205/3306* (2013.01); *A61M 2205/3334* (2013.01); *A61M 2205/3348* (2013.01); *A61M 2205/3368* (2013.01); *A61M 2205/3375* (2013.01); *A61M 2205/3389* (2013.01); *A61M 2205/505* (2013.01); *A61M 2205/584* (2013.01); *A61M 2205/6027* (2013.01); *A61M 2205/6072* (2013.01); *A61M 2205/6081* (2013.01); *A61M 2205/702* (2013.01)

(58) Field of Classification Search
CPC .............. A61M 16/0051; A61M 16/10; A61M 16/1075; A61M 16/16; A61M 16/162; A61M 16/164; A61M 16/165; A61M 16/167; A61M 16/168; A61M 16/18; A61M 16/183; A61M 16/186; A61M 2205/14; A61M 2205/3306; A61M 2205/3334; A61M 2205/3375; A61M 2205/3389; F24F 1/0087; F24F 1/037; F24F 11/0008; F24F 2006/001; F24F 2006/003; F24F 2006/005; F24F 2006/006; F24F 2006/008; F24F 2006/046; F24F 2006/065; F24F 2006/143; F24F 2006/146; F24F 2110/20; F24F 3/14; F24F 6/00; F24F 6/02; F24F 6/025; F24F 6/04; F24F 6/043; F24F 6/06; F24F 6/08; F24F 6/10; F24F 6/105; F24F 6/12; F24F 6/14; F24F 6/16; F24F 6/18

See application file for complete search history.

(56) References Cited

U.S. PATENT DOCUMENTS

| | | | | |
|---|---|---|---|---|
| 4,938,079 | A * | 7/1990 | Goldberg | G01F 1/7084 |
| | | | | 73/861.95 |
| 5,307,243 | A | 4/1994 | Sharp et al. | |
| 5,349,946 | A | 9/1994 | McComb | |
| 5,359,179 | A | 10/1994 | Desloge et al. | |
| 5,367,604 | A | 11/1994 | Murray | |
| 5,379,650 | A | 1/1995 | Kofoed et al. | |
| 5,782,233 | A | 7/1998 | Niemi et al. | |
| 6,039,696 | A | 3/2000 | Bell | |
| 6,554,260 | B1 | 4/2003 | Lipscombe et al. | |
| 6,935,192 | B2 * | 8/2005 | Sobek | G01F 1/7084 |
| | | | | 73/861.95 |
| 6,978,779 | B2 * | 12/2005 | Haveri | A61M 16/08 |
| | | | | 128/204.22 |
| 6,983,652 | B2 | 1/2006 | Blakley et al. | |
| 7,024,945 | B2 | 4/2006 | Wallace | |
| 7,093,501 | B2 | 8/2006 | Kuo et al. | |
| 7,525,663 | B2 | 4/2009 | Kwok et al. | |
| 8,049,143 | B2 | 11/2011 | Andel et al. | |
| 8,063,343 | B2 | 11/2011 | Mcghin et al. | |
| 8,381,729 | B2 | 2/2013 | Freitag et al. | |
| 8,733,349 | B2 | 5/2014 | Bath et al. | |
| 9,566,409 | B2 * | 2/2017 | Gründler | A61M 13/003 |
| 9,572,949 | B2 * | 2/2017 | Vos | A61M 16/0883 |
| 9,592,356 | B2 * | 3/2017 | Truschel | A61M 16/0057 |
| 9,642,966 | B2 * | 5/2017 | Lee | A61M 5/1414 |
| 9,937,314 | B2 | 4/2018 | Buechi et al. | |
| 9,937,316 | B2 | 4/2018 | Buechi et al. | |
| 9,943,108 | B2 | 4/2018 | Lord | |
| 10,226,592 | B2 * | 3/2019 | Acker | A61M 16/01 |
| 10,279,140 | B2 | 5/2019 | Winski | A61M 16/16 |
| 10,363,382 | B2 * | 7/2019 | Vos | A61M 16/0883 |
| 10,398,871 | B2 | 9/2019 | Cortez, Jr. et al. | |
| 10,449,323 | B2 * | 10/2019 | Cheung | A61M 16/167 |
| 10,663,420 | B2 * | 5/2020 | Haick | G01N 27/127 |
| 10,751,490 | B2 * | 8/2020 | Martin | A61M 16/0051 |
| 10,905,843 | B2 * | 2/2021 | Smith | A61M 16/109 |
| 10,942,140 | B2 * | 3/2021 | Haick | G01N 27/127 |
| 11,260,186 | B2 * | 3/2022 | Vos | A61M 16/1095 |
| 11,445,996 | B2 * | 9/2022 | Qi | A61B 8/445 |
| 11,471,641 | B2 * | 10/2022 | Acker | A61M 16/1005 |
| 11,511,069 | B2 * | 11/2022 | Jackson | A61M 16/0833 |
| 11,684,736 | B2 | 6/2023 | Liu et al. | |
| 11,779,719 | B2 * | 10/2023 | Vos | A61M 16/0883 |
| | | | | 128/204.17 |
| 2002/0100320 | A1 | 8/2002 | Smith et al. | |
| 2003/0116556 | A1 | 6/2003 | Li | |
| 2003/0196660 | A1 * | 10/2003 | Haveri | A61M 16/147 |
| | | | | 128/203.12 |
| 2005/0066747 | A1 * | 3/2005 | Sobek | G01F 1/7084 |
| | | | | 73/861.95 |
| 2006/0211981 | A1 | 9/2006 | Sparks et al. | |
| 2007/0181127 | A1 | 8/2007 | Jin et al. | |
| 2007/0265877 | A1 | 11/2007 | Rice et al. | |
| 2007/0272239 | A1 | 11/2007 | Aylsworth et al. | |
| 2008/0308100 | A1 | 12/2008 | Pujol et al. | |
| 2009/0045829 | A1 | 2/2009 | Awazu et al. | |
| 2009/0110379 | A1 | 4/2009 | Mcghin et al. | |
| 2009/0194106 | A1 | 8/2009 | Smith et al. | |
| 2010/0206308 | A1 | 8/2010 | Klasek et al. | |
| 2011/0023874 | A1 | 2/2011 | Bath et al. | |
| 2011/0049123 | A1 | 3/2011 | Frock et al. | |
| 2011/0088693 | A1 | 4/2011 | Somervell et al. | |
| 2011/0162647 | A1 | 7/2011 | Huby et al. | |
| 2011/0253136 | A1 | 10/2011 | Sweeney et al. | |
| 2012/0017904 | A1 | 1/2012 | Ratto et al. | |
| 2012/0073573 | A1 | 3/2012 | Thudor et al. | |
| 2012/0125333 | A1 | 5/2012 | Bedford et al. | |
| 2012/0248636 | A1 | 10/2012 | Fridberg et al. | |
| 2013/0081621 | A1 | 4/2013 | Korneff et al. | |
| 2013/0171733 | A1 * | 7/2013 | Haick | G01N 27/223 |
| | | | | 436/39 |
| 2013/0269697 | A1 * | 10/2013 | Truschel | A61M 16/0051 |
| | | | | 128/204.23 |
| 2014/0007872 | A1 * | 1/2014 | Grundler | A61M 13/003 |
| | | | | 128/203.14 |
| 2014/0202460 | A1 | 7/2014 | Bath et al. | |
| 2014/0216459 | A1 * | 8/2014 | Vos | A61M 16/16 |
| | | | | 128/204.17 |
| 2014/0238394 | A1 | 8/2014 | Beuchi | |
| 2014/0261418 | A1 | 9/2014 | Huang | |
| 2015/0048530 | A1 * | 2/2015 | Cheung | A61M 16/024 |
| | | | | 261/135 |
| 2015/0273144 | A1 * | 10/2015 | Lee | A61M 5/16886 |
| | | | | 73/204.11 |
| 2015/0273175 | A1 * | 10/2015 | Acker | A61M 16/1005 |
| | | | | 128/203.14 |
| 2015/0306335 | A1 * | 10/2015 | Winski | A61M 16/16 |
| | | | | 128/203.14 |
| 2016/0228671 | A1 * | 8/2016 | Jackson | A61M 16/0833 |
| 2017/0113009 | A1 * | 4/2017 | Vos | A61M 16/1095 |
| 2017/0266399 | A1 | 9/2017 | Campana et al. | |
| 2017/0336086 | A1 * | 11/2017 | Lin | A61M 16/109 |

(56) References Cited

U.S. PATENT DOCUMENTS

| | | | |
|---|---|---|---|
| 2018/0028773 A1 | 2/2018 | Klasek et al. | |
| 2018/0236191 A1* | 8/2018 | Martin | A61M 16/026 |
| 2019/0076617 A1* | 3/2019 | Smith | A61M 16/0069 |
| 2019/0290866 A1* | 9/2019 | Vos | A61M 16/0003 |
| 2019/0357875 A1* | 11/2019 | Qi | A61B 8/06 |
| 2020/0206442 A1 | 7/2020 | Knepper et al. | |
| 2020/0284743 A1* | 9/2020 | Haick | G01N 27/127 |
| 2021/0268195 A1* | 9/2021 | Kitaguchi | G01P 5/26 |
| 2022/0152325 A1* | 5/2022 | Vos | A61M 16/0057 |
| 2023/0302240 A1 | 9/2023 | Liu et al. | |
| 2023/0310779 A1* | 10/2023 | Liu | A61M 16/0051 |
| | | | 128/200.24 |
| 2024/0325648 A1* | 10/2024 | Kitaguchi | G01P 13/0006 |

FOREIGN PATENT DOCUMENTS

| | | |
|---|---|---|
| AU | 2017268523 A1 | 12/2017 |
| CN | 205227470 U | 5/2016 |
| EP | 1014527 A2 | 6/2000 |
| EP | 2039387 A1 | 3/2009 |
| EP | 2143459 | 1/2010 |
| EP | 2229973 | 9/2010 |
| EP | 2524714 | 11/2012 |
| EP | 3139986 | 3/2017 |
| GB | 2495771 | 7/2018 |
| JP | H9-70437 A | 3/1997 |
| JP | 2016118511 A | 6/2016 |
| NZ | 587113 A | 12/2011 |
| WO | WO 2000/027457 | 5/2000 |
| WO | WO 2003/048721 | 6/2003 |
| WO | WO 2006/092001 | 9/2006 |
| WO | WO 2008/055307 | 5/2008 |
| WO | WO 2008/091164 | 7/2008 |
| WO | WO 2009/085995 | 7/2009 |
| WO | WO 2010/031126 | 3/2010 |
| WO | WO 2010/141983 A1 | 12/2010 |
| WO | WO 2012/080941 A1 | 6/2012 |
| WO | WO 2012/135912 | 10/2012 |
| WO | WO 2012/164407 | 12/2012 |
| WO | WO 2013/057146 | 4/2013 |
| WO | WO 2013/147623 | 10/2013 |
| WO | WO 2013/165263 | 11/2013 |
| WO | WO 2013/176557 A1 | 11/2013 |
| WO | WO 2014/052983 | 4/2014 |
| WO | WO 2015/038014 A1 | 3/2015 |
| WO | WO 2015/135040 | 9/2015 |
| WO | WO 2017/027906 A1 | 2/2017 |
| WO | WO 2017/126980 | 7/2017 |
| WO | WO 2017/126980 A2 | 7/2017 |
| WO | WO 2018/070883 A1 | 4/2018 |
| WO | WO 2020/204731 A1 | 10/2020 |
| WO | WO 2022/023984 | 2/2022 |

OTHER PUBLICATIONS

Written Opinion in corresponding International Patent Application No. PCT/NZ2020/050029, dated Jul. 21, 2020, in 12 pages.

International Preliminary Report on Patentability in corresponding International Patent Application No. PCT/NZ2020/050029, dated Sep. 28, 2021, in 13 pages.

\* cited by examiner

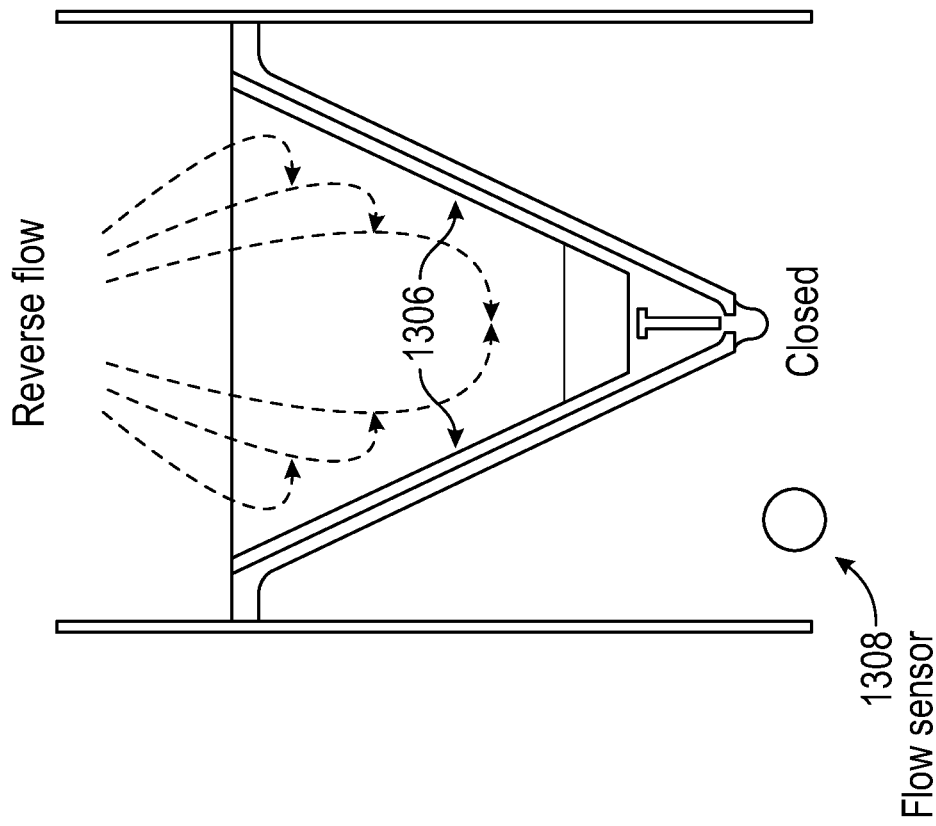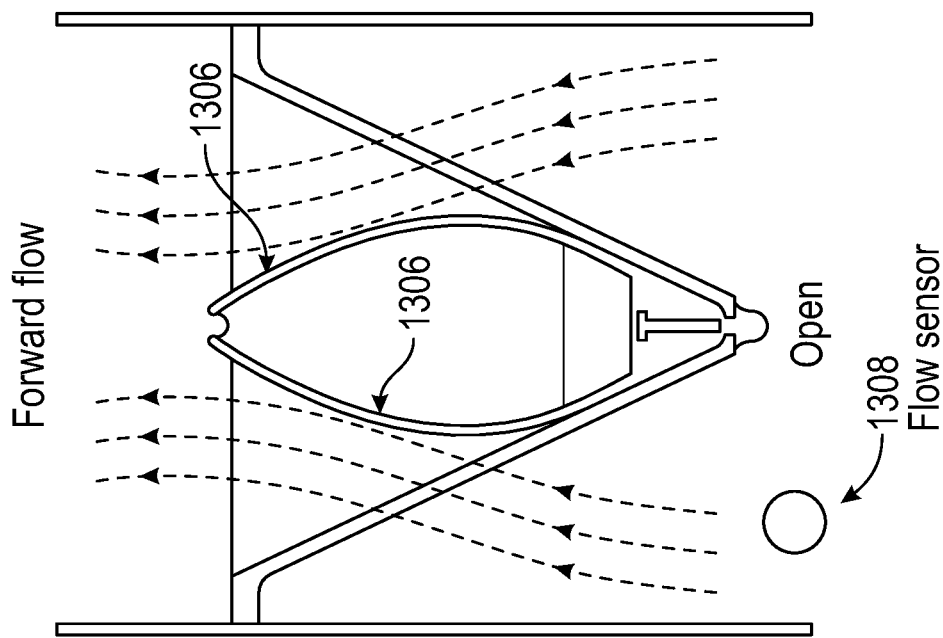
FIG. 13B

SYSTEMS AND METHODS OF DETECTING INCORRECT CONNECTIONS IN A HUMIDIFICATION SYSTEM

FIELD

The present application relates to a humidification system for providing humidified gases to a user or a patient. In particular, the present application relates to detecting connection errors and/or a condition indicative of connection errors between components in the humidification system.

BACKGROUND

A number of methods can be used to supply humidified gases to a user or a patient. Respiratory assistance humidification systems generally include a source of pressurized gases (for example, air, oxygen or other mixtures of gases) such as a ventilator, a humidifier including a source of water and a heating element to vaporize the water so as to humidify the gases from the gases source, a tube (that is, a dry line) for conveying breathing gases from the gases source to the humidifier, and a conduit (that is, an inspiratory conduit) to convey the humidified gases to a patient interface, such as a mask, a nasal cannula, and the like. Humidification systems can be single-limb or dual-limb. In a single-limb system, exhaled gases from the patient can be released into the ambient air via vent holes on the patient interface or some other venting device. In a dual-limb system, exhaled gases can be conveyed from the patient back to the gases source via an expiratory conduit.

SUMMARY

For proper functioning of a humidification system the gases flow should flow in a normal (that is, correct or operative or therapeutic) direction from the gases source through the humidifier to the patient and the components of the humidification system must be connected correctly in order to facilitate gases flow in the normal direction (i.e. correct or operative or therapeutic direction). The correct or normal direction can be termed as a forward flow direction. The correct connections and normal flow direction can ensure that the gases are delivered to the patient at a desired humidity and a desired temperature. The desired humidity is a therapeutic humidity level. Incorrect connections in the humidification system can occur between various components, for example, between two or more of the patient interface, conduits that transport gases, humidifier and/or to/from gases source.

Incorrect connections in the humidification system (which can include at least a gases source, a dry line, a humidifier, an inspiratory conduit, a patient interface, an expiratory conduit, and any connectors therebetween) can be due to a set up error. The gases source can include one or more sources of respiratory gases, which will be shortened to "gases source" throughout this disclosure. Caregivers can incorrectly couple conduits that have the corresponding end connectors of the same type, such as for example the 22 mm male and female medical taper connectors or other standard connectors. The caregiver can connect the humidifier and gases source incorrectly (for example, such that the gas does not flow from the gases source to the humidifier). Non-standard connections may help ameliorate this issue, such as, for example, at the humidifier outlet or on a conduit. However, other components of the humidification system can also be incorrectly connected to each other.

The incorrect connections can result in reverse flow conditions. A reverse flow condition can be a condition when the gases flow in the wrong (that is, incorrect or reverse) direction as compared to a forward flow direction (that is, desired or therapeutic or normal direction). A reverse flow condition is a condition when gases flow in an opposite direction to the forward flow direction. Incorrect connections of the components can result in the gases being delivered to the patient outside therapeutic humidity ranges and/or outside desired temperature or therapeutic temperature ranges. This can lead to unsatisfactory treatments, discomfort, and/or adverse reactions in the patient. In one example of a reverse flow condition, dry air can be delivered from the gases source directly to the patient, whereas humidified gases can be delivered to the gases source. In this regard, such incorrect configuration can result in the humidifier being bypassed, resulting in dry gas being delivered to the patient. Dry gases can cause discomfort and/or may also cause damage to the patient's airways. In some examples, incorrect connections can cause exhaled air from the patient to be delivered to the humidifier. In a reverse flow condition, damage can also occur to the gases source (for example, the ventilator or other gases source) due to provision of humidity to the gases source. The humidity provided to the gases source can cause condensate formation that can damage the gases source.

A reverse flow condition can be indicative of incorrect connections or an incorrect set up by a clinician or nurse. Many current humidification systems cannot directly detect a reverse flow condition due to a lack of such detection systems. Further, components of humidification systems (for example, conduits) have identical connectors or standardized connectors that can couple to multiple other components, thereby creating a risk of misconnection between components. Often humidification systems do not have a detection system to detect incorrect connection between components.

Some humidification systems can detect if the patient is exhaling through the inspiratory conduit by detecting a higher temperature at a humidifier inlet than at a gases source, and/or by comparing flow rates and/or power dissipation curves at the humidifier inlet and outlet. These detection features can help in identifying whether the system is single-limb or dual-limb.

Some humidification systems can minimize errors in the connections of the components by having non-standard end connectors for dedicated tubes and conduits. For example, the inspiratory conduit can have an end connector with distinguishing connecting features that can only be connected to the humidifier outlet. However, these humidification systems cannot detect reverse flow conditions.

Humidification systems of the present disclosure can detect, for example, automatically detect incorrect connections and alert a user. The system can detect errors in the connections between components such as for between patient interface, humidifier, and/or gases source, in the system. Humidification systems of the present disclosure can detect incorrect conduit connection within the system. Humidification systems of the present disclosure can detect the existence of a reverse flow condition/situation (that is, a condition where gases are flowing in the wrong direction) where a patient is receiving sub-optimal humidity and/or temperature. The methods disclosed herein can detect if the gases are flowing in the wrong direction. The wrong direction is a reverse flow direction. A reverse flow condition detected by the methods described herein likely indicates errors in the connections between two or more components of the humidification system. The incorrect connection can include improper connection and/or disconnection of the expiratory conduit. The reverse flow condition detection can include warning a user. The disclosed methods may also determine a fault or an incorrect operation parameter detected in the system, which is indicative of incorrect connections in the system (that is, incorrect connections between components in the system).

The present disclosure also relates to detection of incorrect connection of the expiratory conduit in dual-limb systems, such as systems used for providing invasive mechanical ventilation therapies, noninvasive mechanical ventilation therapies, neonatal invasive or noninvasive therapies and/or other therapies.

In some configurations, a method of detecting reverse flow condition in a humidification system comprising a gases source, a humidifier, and a breathing circuit, the humidifier comprising a base comprising a heater plate and a chamber that carries humidification fluid, the chamber positionable on the base, the breathing circuit comprising an inspiratory conduit, an expiratory conduit, and a dryline, can include, using a controller of the humidification system, controlling a tracer injection unit to introduce or remove a tracer at a first location along a gases flow path in the system. The method can also include detecting the tracer or absence of the tracer, or determining a change in the system in response to the tracer or absence of the tracer, at a second location along the gases flow path in the system, the second location being different than the first location. The method can also include outputting an indication of reverse flow condition based on detecting the tracer or absence of the tracer or determining the change in the system in response to the tracer or absence of the tracer.

In some configurations, the tracer can include radiant energy, thermal energy, moisture, dye, chemical, or a gas.

In some configurations, the detecting or the determining can include a visual detecting or determining a presence of the tracer or an absence of the tracer.

In some configurations, the detecting or the determining can be performed using one or more sensors.

In some configurations, the one or more sensors can include a temperature sensor, a pressure sensor, or a humidity sensor.

In some configurations, the one or more sensors can be located at the first location.

In some configurations, the one or more sensors can be located at the second location.

In some configurations, the one or more sensors can be located at the first location and the second location.

In some configurations, the determining a change in the system can include comparing sensor measurement at the first location and the second location.

In some configurations, the first location can be located downstream with respect to the second location, in relation to a normal or therapeutic flow condition.

In some configurations, the one or more sensors at the first location may be downstream of the tracer injection unit and the one or more sensors at the second location can be upstream of the tracer injection unit, so that the one or more sensors at the first location detecting the tracer is indicative of a normal flow condition and the one or more sensors at the second location detecting the tracer can be indicative of a reverse flow condition.

In some configurations, the tracer is introduced periodically.

In some configurations, the tracer is introduced once.

In some configurations, the tracer is introduced during setup of the system or just after setup of the system.

In some configurations, the introducing can be during operation of the system.

In some configurations, the breathing circuit can comprise the chamber.

In some configurations, the tracer injection unit is upstream of the humidifier, or positioned in or along the inspiratory conduit, or adjacent a wye-piece, or between the chamber and the inspiratory conduit.

In some configurations, the method can further include outputting a warning to a user of the system if a reverse flow condition is detected.

In some configurations, the method can include wherein the reverse flow condition is indicative of incorrect connection of at least one component of the humidification system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, the method can be performed during setup of the system or just after setup is finished. In some configurations, the method can be performed during steady state operation of the system.

In another configuration, a method of detecting reverse flow condition in a respiratory humidification system comprising a gases source, a humidifier, and a breathing circuit, the humidifier comprising a base comprising a heater plate and a chamber that carries humidification fluid, the chamber positionable on the base, the breathing circuit comprising an inspiratory conduit, an expiratory conduit, and a dryline can include, using a controller of the humidification system, introducing a flow of gas into a humidification chamber inlet. The method can also include detecting a change in the humidification chamber and/or detecting a change in the contents of the humidification chamber. The method can also include outputting an indication of reverse flow condition based on the detected change in the humidification chamber and/or detecting a change in the contents of the humidification chamber.

In some configurations, the breathing circuit can comprise the chamber.

In some configurations, the humidification chamber can include a flow guide near the humidification chamber inlet. The flow guide can be configured to direct the flow of gas into the chamber. The chamber can include a sensor positioned adjacent the inlet. The sensor can detect a change in the contents in the humidification chamber that can include measuring a parameter of the flow of gas passing into the chamber. The controller can output an indication of a reverse flow condition based on comparing the measured parameter with a threshold. A detected reverse flow condition can be indicative of incorrect connections between one or more components within the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, the detecting can include measuring a temperature of a water surface below or adjacent the inlet of the humidification chamber. The reverse flow condition can be detected based on comparing the measured temperature with a threshold. In some configurations, the measured temperature being higher than the threshold can be indicative of a reverse flow condition.

In some configurations, the detecting can include monitoring a contour of a water surface in the humidification chamber.

In some configurations, the detecting of the contour of the water surface can be performed by an optical sensor. In some configurations, the contour of the water surface changing can be indicative of a flow direction.

In some configurations, the optical sensor can be adjacent the humidification chamber inlet and detect a change in the contour of the water surface adjacent the humidification chamber inlet that is indicative of a normal flow condition, wherein the change in the water contour can be compared to a threshold, the change being greater than a threshold can be indicative of normal flow, and the change being below a threshold or different to the threshold by a set amount can be indicative of a reverse flow.

In some configurations, the optical sensor may be adjacent the humidification chamber outlet of the humidifier, the contour of the water surface being detected adjacent the humidification chamber outlet being indicative of a reverse flow condition.

In some configurations, the chamber can include a flow sensor positioned adjacent the inlet of the chamber and the detecting comprises measuring a flow rate at the humidification chamber inlet.

In some configurations, the chamber can include a pressure sensor adjacent the inlet of the chamber and the detecting can include measuring pressure drops at the humidification chamber inlet and a humidification chamber outlet.

In some configurations, the chamber can include a sensor configured to detect a presence of condensation at or near an inner surface of the chamber.

In some configurations, the sensor can be configured to detect the presence of condensation directly or indirectly.

In some configurations, the sensor can include a humidity sensor. In some configurations, the sensor can include a capacitive humidity sensor. In some configurations, the sensor can include an optical sensor. In some configurations, the sensor can include a thermopile.

In some configurations, the sensor can be positioned at or near the inlet of the chamber.

In some configurations, the detecting can be periodic.

In some configurations, the detecting can be done once.

In some configurations, the detecting can be during setup of the system or just after setup is finished.

In some configurations, the detecting can be during steady state operation of the system.

In some configurations, the method can include outputting a warning to a user of the system.

In some configurations, a method of detecting reverse flow condition in a respiratory humidification system comprising a gases source, a humidifier, and a breathing circuit, the humidifier comprising a base comprising a heater plate and a chamber that carries humidification fluid, the chamber positionable on the base, the breathing circuit comprising an inspiratory conduit, an expiratory conduit, and a dryline, can include emitting an ultrasonic signal using a first ultrasonic transducer positioned at a first location in a gases flow path of the system. The method can also include detecting the ultrasonic signal using a second ultrasonic transducer position at a second location in the gases flow path different than the first location. The method can also include determining an indication of reverse flow condition based at least on the detected ultrasonic signal.

In some configurations, the breathing circuit can comprise the chamber.

In some configurations, the first location being upstream of the second location in a normal flow condition.

In some configurations, the second location can be located downstream in relation to the first location in a normal flow condition.

In some configurations, the first location can be closer to an inlet of a conduit and the second location can be closer to an outlet of the conduit.

In some configurations, the method can include measuring a time of flight of the ultrasonic signal.

The method further comprises comparing the time of flight of the ultrasound signal with a threshold, and a reverse flow condition being determined if the time of flight is greater than a threshold.

In some configurations, the method can also include emitting a second ultrasonic signal using the second ultrasonic transducer. The method can also include detecting the second ultrasonic signal using the first ultrasonic transducer position. The method can also include determining reverse flow and/or incorrect connection based at least on the detected ultrasonic signal and the second detected ultrasonic signal.

In some configurations, the determining a reverse flow condition can be based on a time of flight of the detected ultrasonic signal (that is, a first ultrasonic signal) and a time of flight of the second detected ultrasonic signal. A reverse flow condition can be detected if the time of flight of detected ultrasonic signal (that is, the first ultrasonic signal) is greater than the time of flight of the second detected ultrasonic signal.

In some configurations, the detecting can be during setup of the system or just after setup is finished. In some configurations, the detecting can be during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a respiratory humidification system configured to deliver a respiratory therapy to a patient can include a gases source. The respiratory humidification system can also include a humidification chamber. The respirator humidification system can also include a user interface. The respiratory humidification system can also include a first breathing circuit configured for connecting the gases source and the humidification chamber. The respiratory humidification system can also include a second breathing circuit configured for connecting the gases source and the patient. The first breathing circuit can be configured to be upstream of the second breathing circuit in a normal flow condition. The respiratory humidification system can also include a reverse flow indicator located in a gases flow path of the system, wherein the reverse flow indicator is in a first configuration during normal flow and a second configuration different from the first configuration during reverse flow.

In some configurations, the reverse flow indicator can include a moveable flap, the flap being moveable between a first position and a second position.

In some configurations, the flap being in a second position can be indicative of reverse flow conditions.

In some configurations, the reverse flow indicator can include an indicator having different color indicators for normal and reverse flow conditions.

In some configurations, the reverse flow indicator can include a valve.

In some configurations, the valve can be closed in reverse flow conditions.

In some configurations, the respiratory humidification system can include a flow sensor downstream of the valve.

In some configurations, the reverse flow indicator can include a turbine.

In some configurations, a polarity of an electrical current generated by rotation of the turbine due to gases flow can be different for normal and reverse flow conditions.

In some configurations, the reverse flow indicator can include a whistle.

In some configurations, a whistling noise can be generated in reverse flow conditions.

In some configurations, the reverse flow indicator can include a flexible attachment including a head and a tail.

In some configurations, a position of a free end of the tail relative to the head can be different in normal and reverse flow conditions.

In some configurations, the reverse flow indicator can include a protrusion into the gases flow path.

In some configurations, the protrusion can include a first end comprising a narrower tip and a second end comprising a rounder tip. The shapes of the first end and the second end can create different flow profiles based at least on a direction of flow.

In some configurations, the protrusion can be teardrop shaped.

In some configurations, the reverse flow indicator can include alternating vortices detected using a flow sensor located upstream of the protrusion, the protrusion creating alternating vortices in reverse flow conditions.

In some configurations, the respiratory humidification system can include a flow sensor upstream of the protrusion. The flow sensor can be configured to detect alternating vortices in reverse flow due to the protrusion.

In some configurations, the first breathing circuit can comprise a dryline. The second breathing circuit can be further configured for connecting the patient and the gases source. The second breathing circuit can comprise inspiratory and expiratory conduits.

In some configurations, the reverse flow indicator can be located in the first or the second breathing circuit.

In some configurations, the system can be configured to detect whether a reverse flow condition is present during setup of the system or just after setup is finished. In some configurations, the system can be configured to detect whether a reverse flow condition is present during steady state operation of the system.

In some configurations, a controller of the system can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a respiratory humidification system configured to deliver a respiratory therapy to a patient can include a gases source. The respiratory humidification system can also include a humidification chamber. The respiratory humidification system can also include a first breathing circuit configured for connecting the gases source and the humidification chamber to allow gases flowing from the gases source to the humidification chamber and a second breathing circuit configured for connecting the humidification chamber and the gases source to allow gases flowing from the humidification chamber to the gases source. The respiratory humidification system can also include a flow path controller configured to redirect a gases flow path in a reverse flow condition.

In some configurations, the first breathing circuit can comprise a dryline, and the second breathing circuit can comprise inspiratory and expiratory conduits in a normal flow condition.

In some configurations, the flow path controller can include a valve configured to switch the gases flow path.

In some configurations, the flow path controller can be activated in response to flow or pressure measurements at humidifier inlet and outlet.

In some configurations, the flow path controller can be activated in response to flow or pressure measurements at gases source inlet or outlet.

In some configurations, the system can be configured to detect whether a reverse flow condition is present during setup of the system or just after setup is finished. In some configurations, the system can be configured to detect whether a reverse flow condition is present during steady state operation of the system.

In some configurations, a controller of the system can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting reverse flow condition in a respiratory humidification system comprising a gases source, a humidifier, and a breathing circuit, the humidifier comprising a base comprising a heater plate and a chamber that carries humidification fluid, the chamber positionable on the base, the breathing circuit comprising an inspiratory conduit, an expiratory conduit, and a dryline, can include, using a controller of the gases source, detecting at a gases source inlet or outlet a characteristic of a gas or a breathing circuit component connected to the gases source. The method can also include determining that a reverse flow condition is present based on the characteristic of the gas.

In some configurations, the breathing circuit can comprise the chamber.

In some configurations, the characteristic can include humidity. The reverse flow condition can be detected if humidity is measured at an inlet of the gases source or if a humidity above a threshold is measured at the inlet of the gases source.

In some configurations, the method can include identifying a type of the breathing circuit component connected to the gases source.

In some configurations, the characteristic can include a resistance of an embedded resistor.

In some configurations, the breathing circuit component can include an RFID tag, a bar code, or a QR code.

In some configurations, the breathing circuit component can include a color code detectable by an optical sensor.

In some configurations, the breathing circuit component can include a magnet, magnets in different breathing circuit components having opposite polarities facing the gases source.

In some configurations, the breathing circuit component can include different features, detection of a presence of the different features providing identification of the type of the breathing circuit component.

In some configurations, the detecting can be during setup of the system or just after setup is finished. In some configurations, the detecting can be during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the gases source to the humidifier and/or the patient monitoring station.

In some configurations, the controller of the gases source may be configured to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting reverse flow in a humidification system comprising a gases source, a humidifier, and a breathing circuit, the humidifier including a base comprising a heater plate and a chamber that carries humidification fluid, the chamber positionable on the base, the breathing circuit comprising an inspiratory conduit, an expiratory conduit, and a dryline can include, using a controller of the gases source, instructing a user to disconnect a conduit that is connected to a gases source outlet. The method can also include sending a test flow. The method can also include measuring a resistance to the test flow at the gases source outlet. The method can also include determining reverse flow conditions based on the resistance to the test flow.

In some configurations, the breathing circuit can also include the chamber.

In some configurations, the resistance to the test flow can be higher when the expiratory conduit is correctly connected to a gases source inlet than when the expiratory conduit is incorrectly connected to the gases source outlet.

In some configurations, the method can be performed during setup of the system or just after setup is finished. In some configurations, the method can be performed during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the gases source to the humidifier and/or the patient monitoring station.

In some configurations, the controller of the gases source may be configured to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting reverse flow in a humidification system comprising a humidifier including a base comprising a heater plate and a chamber that carries humidification fluid, the chamber positionable on the base, the breathing circuit comprising an inspiratory conduit, an expiratory conduit, and a dryline, can include, using a controller of the humidifier, communicating with a controller of the gases source. The method can also include beginning a reverse flow condition test. The method can also include determining that a reverse flow condition is present based on a change at the humidifier or a change at the gases source in response to the test.

In some configurations, the breathing circuit can comprise the chamber.

In some configurations, the beginning the reverse flow condition test can include sending a test flow to the humidifier by the controller of the gases source.

In some configurations, the beginning the reverse flow condition test can include sending a tracer to the gases source by the controller of the humidifier.

In some configurations, the beginning the reverse flow condition test can include sending a tracer to the humidification chamber by a controller of the gases source.

In some configurations, the detecting can be during setup of the system or just after setup is finished. In some configurations, the detecting can be during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a humidification system configured to detect a reverse flow condition in a humidification system can include a controller. The controller can be a controller of a gases source or a humidifier of the humidification system. The controller can control a tracer injection unit to introduce or remove a tracer at a first location along a gases flow path of the system, the gases flow path located in at least a gases source, a humidifier, and a breathing circuit of the system, the humidifier comprising a base comprising a heater plate and a chamber that carries humidification fluid, the chamber positionable on the base, the breathing circuit comprising an inspiratory conduit, an expiratory conduit, and a dryline. The controller can detect the tracer or absence of the tracer, or determining a change in the system in response to the tracer or absence of the tracer, at a second location along the gases flow path in the system, the second location being different than the first location. The controller can output an indication of reverse flow condition based on detecting the tracer or absence of the tracer or determining the change in the system in response to the tracer or absence of the tracer.

In some configurations, the breathing circuit can comprise the chamber.

In some configurations, the tracer can include radiant energy, thermal energy, moisture, dye, chemical, or a gas.

In some configurations, the first sensor can be an optical sensor configured to visually detecting or determining a presence of the tracer or the absence of the tracer.

In some configurations, the system can include one or more sensors.

In some configurations, the one or more sensors can include a temperature sensor, a pressure sensor, or a humidity sensor.

In some configurations, the one or more sensors can be located at the first location.

The In some configurations, the one or more sensors can be located at the second location.

In some configurations, the one or more sensors can be located at the first location and the second location.

In some configurations, the one or more sensors at the first location and the second location can collect sensor measurements. The sensor measurements of the one or more sensors can be compared to determining whether there is a change in the humidification system.

In some configurations, the first location can be located downstream with respect to the second location in relation to a normal or therapeutic flow condition.

In some configurations, the one or more sensors at the first location may be downstream of the tracer injection unit and the one or more sensors at the second location can be upstream of the tracer injection unit, so that the one or more sensors at the first location detecting the tracer is indicative of a normal flow condition and the one or more sensors at the second location detecting the tracer can be indicative of a reverse flow condition.

In some configurations, the tracer injection unit can periodically introduce the tracer.

In some configurations, the tracer injection unit can introduce the tracer once when performing reverse flow detection.

In some configurations, the tracer injection unit can introduce the tracer during setup of the humidification system or just after setup of the system.

In some configurations, the tracer injection unit can introduce the tracer during operation of the humidification system.

In some configurations, the user interface can generate and output a warning if a reverse flow condition is detected.

In some configurations, the reverse flow condition can be indicative of incorrect connection of at least one component of the humidification system.

In some configurations, the user interface can generate an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, the detecting can be during setup of the system or just after setup is finished. In some configurations, the detecting can be during steady state operation of the system.

In some configurations, a system for detecting a reverse flow condition in a humidification system can include a controller. The controller can be a controller of a gases source or a humidifier of the system. The controller can introduce a flow of gas into a humidification chamber inlet of a humidification chamber of the system, the humidification chamber comprising a base comprising a heater plate and a chamber that carries humidification fluid, the chamber positionable on the base. The controller can detect a change in the humidification chamber and/or detect a change in the contents of the humidification chamber. The controller can output an indication of reverse flow condition based on the detected change in the humidification chamber and/or the detected change in the contents of the humidification chamber.

In some configurations, the humidification chamber can include a flow guide near the inlet. The flow guide can direct the flow of gas into the humidification chamber, the humidification chamber including a sensor positioned adjacent the inlet. The change in the contents in the humidification chamber can include a parameter of the flow of gas passing into the chamber. The reverse flow condition can be outputted based on comparing the measured parameter with a threshold.

In some configurations, the controller can be configured to generate an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, the system can comprise a sensor which can measure a temperature of a water surface below or adjacent the inlet of the humidification chamber. The reverse flow condition can be detected based on comparing the measured temperature with a threshold. In some configuration, the temperature higher than the threshold can be indicative of a reverse flow condition.

In some configurations, the sensor can monitor the contour of a water surface in the humidification chamber.

In some configurations, the sensor can be an optical sensor that detects the contour of the water surface. In some configurations, the contour of the water surface changing can be indicative of a flow direction.

In some configurations, the optical sensor can be adjacent the humidification chamber inlet and detect a change in the contour of the water surface adjacent the humidification chamber inlet that is indicative of a normal flow condition, wherein the change in the water contour can be compared to a threshold, the change being greater than a threshold can be indicative of normal flow, and the change being below a threshold or different to the threshold by a set amount can be indicative of a reverse flow.

In some configurations, the optical sensor may be adjacent the humidification chamber outlet of the humidifier, the contour of the water surface being detected adjacent the humidification chamber outlet being indicative of a reverse flow condition.

In some configurations, the sensor can be a flow sensor positioned adjacent the inlet of the chamber and configured to measure a flow rate at the inlet of the humidification chamber.

In some configurations, the sensor can be a pressure sensor positioned adjacent the inlet of the chamber and configured to measure pressure drops at the humidification chamber inlet and a humidification chamber outlet.

In some configurations, the chamber can include a sensor configured to detect a presence of condensation at or near an inner surface of the chamber.

In some configurations, the sensor can be configured to detect the presence of condensation directly or indirectly.

In some configurations, the sensor can include a humidity sensor. In some configurations, the sensor can include a capacitive humidity sensor. In some configurations, the sensor can include an optical sensor. In some configurations, the sensor can include a thermopile.

In some configurations, the sensor can be positioned at or near the inlet of the chamber.

In some configurations, the sensor can periodically detect the change in the humidification chamber.

In some configurations, the sensor can detect the changes in the humidification chamber during setup of the system or just after setup is finished.

In some configurations, the first sensor can detect the changes in the humidification system during setup of the humidification system or just after setup is finished.

In some configurations, the first sensor can detect the changes in the humidification system during steady state operation of the humidification system.

In some configurations, the user interface can output a warning to a user of the humidification system.

In some configurations, a system configured to detect reverse flow condition in a humidification system can include a controller configured to emit an ultrasonic signal using a first ultrasonic transducer positioned at a first location in a gases flow path of the system, the gases flow path located in at least a gases source, a humidifier, and a breathing circuit of the system, the humidifier including a base comprising a heater plate and a chamber that carries humidification fluid, the chamber positionable on the base, the breathing circuit including an inspiratory conduit, an expiratory conduit, and a dryline. The controller can detect the ultrasonic signal using a second ultrasonic transducer position at a second location in the gases flow path different than the first location. The controller can determine an indication of reverse flow condition based at least on the detected ultrasonic signal.

In some configurations, the breathing circuit can include the chamber.

In some configurations, the second location can be located downstream in relation to the first location in a normal flow condition.

In some configurations, the controller can determine a time of flight of the first ultrasonic signal.

In some configurations, the controller can further emit a second ultrasonic signal using the second ultrasonic transducer. The controller can detect the second ultrasonic signal using the first ultrasonic transducer position. The controller can determine a reverse flow condition based at least on the detected ultrasonic signal and the second detected ultrasonic signal.

In some configurations, the controller can determine whether there is a reverse flow condition based on a time of flight of the first ultrasonic signal and a time of flight of the second ultrasonic signal.

In some configurations, the determining can be during setup of the system or just after setup is finished. In some configurations, the determining can be during steady state operation of the system.

In some configurations, the controller can be configured to generate an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting a reverse flow condition in a humidification system configured to deliver a respiratory therapy to a patient, the humidification system including a gases source, a humidifier, and a breathing circuit, the humidifier including a base comprising a heater plate and a chamber that carries humidification fluid, the chamber positionable on the base, the breathing circuit including an inspiratory conduit, an expiratory conduit, and a dryline, can include monitoring a reverse flow indicator located in a gases flow path of the humidification system, the reverse flow indicator having a first configuration during normal flow conditions and a second configuration during reverse flow conditions, the second configuration being different from the first configuration. The method can include determining whether the reverse flow indicator is in at least one of the first or second configuration. The method can include upon determining that the reverse flow indicator is in the second configuration and/or not in the first configuration, generating and outputting an indication that a reverse flow is present.

In some configurations, the breathing circuit can comprise the chamber.

In some configurations, the monitoring the reverse flow indicator can include monitoring a flap of the reverse flow indicator. The flap can be moveable between a first position and a second position.

In some configurations, the monitoring the flap can include determining if the flap is in the second position indicative of reverse flow conditions.

In some configurations, the monitoring the flap can include monitoring the flap for different color indicators for normal and reverse flow conditions.

In some configurations, the monitoring the reverse flow indicator can include monitoring a valve configuration.

In some configurations, the determining whether the reverse flow indicator is in the second configuration can include determining whether the valve is closed.

In some configurations, the method can include detecting a flow rate using a flow sensor downstream of the valve.

In some configurations, the monitoring the reverse flow indicator can include monitoring rotation of a turbine.

In some configurations, the monitoring the reverse flow indicator can include monitoring a polarity of an electrical current generated by the rotation of the turbine caused by a gases flow.

In some configurations, the monitoring the reverse flow indicator can include monitoring a flexible attachment including a head and a tail.

In some configurations, the monitoring the reverse flow indicator can include monitoring a position of a free end of the tail relative to the head.

In some configurations, the monitoring the reverse flow indicator can include monitoring a protrusion positioned within the gases flow path.

In some configurations, the monitoring the reverse flow indicator can include monitoring different flow profiles based at least on a direction of flow and created by the protrusion including a first end having a narrower tip and a second end having a rounder tip.

In some configurations, the monitoring the reverse flow indicator can include monitoring the protrusion that is teardrop shaped.

In some configurations, the monitoring the reverse flow indicator can include detecting alternating vortices using a flow sensor located upstream of the protrusion, the protrusion creating alternating vortices in reverse flow conditions.

In some configurations, the monitoring the reverse flow indicator can include monitoring the reverse flow indicator located in an inspiratory conduit, an expiratory conduit, or a dryline of the humidification system.

In some configurations, the monitoring the reverse flow indicator can include monitoring the reverse flow indicator located in the breathing circuit of the humidification system.

In some configurations, the detecting can be during setup of the system or just after setup is finished. In some configurations, the detecting can be during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of redirecting a flow in a humidification system configured to deliver a respiratory therapy to a patient, the humidification system including a gases source, a humidifier, and a breathing circuit, the humidifier including a base including a heater plate and a chamber that carries humidification fluid, the chamber positionable on the base, the breathing circuit including an inspiratory conduit, an expiratory conduit, and a dryline can include collecting a first data at a first location. The method can include collecting a second data at a second location. The method can include comparing the first data to the second data. The method can include based at least on the comparison between the first data and the second data, determining that a reverse flow condition is present. The method can include upon determining that a reverse flow condition is present, redirecting flow in the humidification system using a flow path controller.

In some configurations, the breathing circuit can comprise the chamber.

In some configurations, the redirecting flow in the humidification system can include actuating a valve system to switch a gas path of the humidification system.

In some configurations, the collecting the first data at the first location can include taking flow or pressure measurements at a humidifier inlet. The collecting the second data at the second location can include taking flow or pressure measurements at a humidifier outlet.

In some configurations, the collecting the first data at the first location can include taking flow or pressure measurements at a gases source inlet. The collecting the second data at the second location can include taking flow or pressure measurements at a gases source outlet.

In some configurations, the determining can be during setup of the system or just after setup is finished. In some configurations, the determining can be during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a system configured to detect a reverse flow condition in a humidification system can include a controller. The controller can be a controller of a gases source or a humidifier. The controller can be configured to detect at a gases source inlet or outlet a characteristic of a gas or a breathing circuit component of the humidification system connected to a gases source, the breathing circuit comprising an inspiratory conduit, an expiratory conduit, and a dryline. The controller can be configured to determine that a reverse flow condition is present based on the characteristic of the gas.

In some configurations, the breathing circuit can comprise the chamber.

In some configurations, the characteristic of the gas can include humidity. A reverse flow condition can be detected if humidity is measured at an inlet of the gases source or if a humidity above a threshold is measured at the inlet of the gases source.

In some configurations, the system can include a first sensor that can identify a type of the breathing circuit component connected to the gases source.

In some configurations, the characteristic can include a resistance of an embedded resistor.

In some configurations, the breathing circuit component can include an RFID tag, a bar code, or a QR code.

In some configurations, the breathing circuit component can include a color code detectable by an optical sensor.

In some configurations, the breathing circuit component can include a magnet, magnets in different breathing circuit components having opposite polarities facing the gases source.

In some configurations, the breathing circuit component can include different features, detection of a presence of the different features providing identification of the type of the breathing circuit component.

In some configurations, the detecting can be during setup of the system or just after setup is finished. In some configurations, the detecting can be during steady state operation of the system.

In some configurations, the controller can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a system configured to detect a reverse flow condition in a humidification system can include a controller. The controller can be a controller of a gases source or a humidifier. The controller can instruct a user to disconnect a conduit of the humidification system, wherein the conduit is connected to a gases source outlet of a gases source of the humidification system. The controller can send a test flow. The controller can measure a resistance to the test flow at the gases source outlet. The controller can determine that a reverse flow condition is present based on the resistance to the test flow.

In some configurations, the resistance to the test flow can be higher when the inspiratory conduit is correctly connected to a gases source outlet than when the expiratory conduit is incorrectly connected to the gases source outlet.

In some configurations, the determining can be during setup of the system or just after setup is finished.

In some configurations, the controller can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a system configured to detect a reverse flow condition in a humidification system can include a controller of a humidifier. The controller can be a controller of a gases source. The controller can communicate with a controller of a gases source of the system, the gases source in fluid communication with the humidifier, the humidifier including a heater plate and a chamber that carries humidification fluid, the chamber positionable on a base. The controller can begin a reverse flow condition test. The controller can determine that a reverse flow condition is present based on a change at the humidifier or a change at the gases source in response to the test.

In some configurations, the reverse flow condition test can include sending a test flow to the humidifier by the controller of the gases source.

In some configurations, the reverse flow condition test can include sending a tracer to the gases source by the controller of the humidifier.

In some configurations, the reverse flow condition test can include sending a tracer to the humidifier by a controller of the gases source.

In some configurations, the determining can be during setup of the system or just after setup is finished. In some configurations, the determining can be during steady state operation of the system.

In some configurations, the controller can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a system configured to detect a reverse flow condition in the humidification system configured to deliver respiratory therapy to a patient can include a sensor configured to output a signal indicative of presence of condensation at or near an inner surface of an inlet of a humidification chamber of the humidification system, the humidification system further comprising a gases source, and a breathing circuit comprising an inspiratory conduit, an expiratory conduit, and a dryline; a controller configured to receive the signal from the sensor and determine a reverse flow condition based at least in part on the received signal.

In some configurations, the breathing circuit can comprise the chamber.

In some configurations, the sensor can be configured to detect the presence of condensation directly or indirectly.

In some configurations, the sensor can include a humidity sensor. In some configurations, the sensor can include a capacitive humidity sensor. In some configurations, the sensor can include an optical sensor. In some configurations, the sensor can include a thermopile configured to detect a temperature change of the inner surface.

In some configurations, the sensor can be positioned at or near the inlet of the humidification chamber.

In some configurations, the determining can be during setup of the system or just after setup is finished. In some configurations, the determining can be during steady state operation of the system.

In some configurations, the controller can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller can include a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting a reverse flow condition in a humidification system configured to deliver respiratory therapy to a patient, the humidification system comprising a gases source, a humidification chamber comprising an inlet and an outlet, and a breathing circuit comprising an inspiratory conduit, an expiratory conduit, and a dryline, can include, using a controller of the humidification system, receiving a signal from a sensor in the humidification system, the signal being indicative of a presence of condensation at or near an inner surface of the inlet of the humidification chamber; and determining a reverse flow condition based at least in part on the received signal.

In some configurations, the sensor can be configured to detect the presence of condensation directly or indirectly.

In some configurations, the sensor can include a humidity sensor. In some configurations, the sensor can include a capacitive humidity sensor. In some configurations, the sensor can include an optical sensor. In some configurations, the sensor can include a thermopile configured to detect a temperature change of the inner surface.

In some configurations, the sensor can be positioned at or near the inlet of the humidification chamber.

In some configurations, the method can be performed during setup of the system or just after setup is finished. In some configurations, the method can be performed during steady state operations of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting a reverse flow condition in a respiratory humidification system comprising a gases source, a humidifier, and a breathing circuit, the humidifier including a base comprising a heater plate and a chamber that carries humidification fluid, the chamber positionable on the base, the breathing circuit comprising an inspiratory conduit, an expiratory conduit, a dryline, and a wye-piece, can include, using a control system of the humidification system: identifying a component of the breathing circuit; controlling the gases source to output a known flow based on the identifying; measuring a resistance to flow measurement; comparing the resistance to flow measurement to an expected resistance to flow value; and outputting a reverse flow condition in response to the resistance to flow measurement being lower than the expected resistance to flow value.

In some configurations, the breathing circuit can comprise the chamber.

In some configurations, the identifying can include directly or indirectly identifying the component of the breathing circuit based upon a capacitance value, an inductance value, or a resistance value.

In some configurations, the control system can be located at the humidifier. In some configurations, the control system is located at the gases source.

In some configurations, the control system can include a humidifier controller and a gases source controller.

In some configurations, the humidifier controller can be configured to be in electrical and/or data communication with the gases source controller.

In some configurations, the reverse flow condition can be determined based at least in part on the humidifier controller being in communication with the gases source controller.

In some configurations, the resistance to flow measurement can be measured by the gases source controller, the humidifier controller communicating with the gases source controller to receive the resistance to flow measurement.

In some configurations, the expected resistance to flow value can be stored in a memory of the humidifier controller or the gases source.

In some configurations, a first end of the wye-piece can be unimpeded as the gases source outputs the known flow.

In some configurations, the first end of the wye-piece can be disconnected from a patient interface as the gases source outputs the known flow.

In some configurations, the method can be performed during setup of the system or just after setup is finished. In some configurations, the method can be performed during steady state operation of the system.

In some configurations, the method can include generating an alarm or indication that an incorrect connection exists in the humidification system. In some configurations, the alarm or indication may be presented to a user via a user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

In some configurations, the controller can be a controller of the humidifier.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a humidification system configured to detect a reverse flow condition in the system can include a control system configured to: identify a component of a breathing circuit that includes an inspiratory conduit, an expiratory conduit, a dryline, and a wye-piece; control a gases source to output a known flow based on the identifying, the gases source in fluid communication with the breathing circuit and a humidifier, the humidifier including a heater plate and a chamber that carries humidification fluid, the chamber positionable on the base; measure a resistance to flow measurement; compare the resistance to flow measurement to an expected resistance to flow value; and output a reverse flow condition in response to the resistance to flow measurement being lower than the expected resistance to flow value.

In some configurations, the breathing circuit can comprise the chamber.

In some configurations, the control system can be configured to directly or indirectly identify the component of the breathing circuit based upon a capacitance value, an inductance value, or a resistance value.

In some configurations, the control system can be located at the humidifier.

In some configurations, the control system can be located at the gases source.

In some configurations, the control system can include a humidifier controller and a gases source controller.

In some configurations, the humidifier controller can be configured to be in electrical and/or data communication with the gases source controller.

In some configurations, the reverse flow condition can be detected when the humidifier controller is in communication with the gases source controller.

In some configurations, the resistance to flow measurement can be measured by the gases source controller, the humidifier controller communicating with the gases source controller to receive the resistance to flow measurement.

In some configurations, the expected resistance to flow value can be stored in a memory of the humidifier controller or the gases source.

In some configurations, a first end of the wye-piece can be unimpeded as the gases source outputs the known flow.

In some configurations, the first end of the wye-piece can be disconnected from a patient interface as the gases source outputs the known flow.

In some configurations, the detecting can be performed during setup of the system or just after setup is finished. In some configurations, the detecting can be performed during steady state operation of the system.

In some configurations, the control system can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a method of detecting reverse flow condition in a respiratory humidification system comprising a gases source, a humidifier, and a breathing circuit, the humidifier including a base comprising a heater plate and a chamber that carries humidification fluid, the chamber positionable on the base, the breathing circuit comprising an inspiratory conduit, an expiratory conduit, and a dryline, can include, using a control system of the humidification system: measuring a first temperature indicative of a temperature of an outlet of the gases source and/or a first end of the dryline using a first sensor; measuring a second temperature indicative of a temperature of an inlet of the chamber and/or a second end of the dryline using a second sensor; comparing a difference between the first temperature and the second temperature; and outputting a reverse flow condition in response to the difference being above a pre-determined temperature threshold.

In some configurations, the breathing circuit can comprise the chamber.

In some configurations, the first sensor can be located in or near the first end of the dryline.

In some configurations, the second sensor can be located at the inlet of the chamber.

In some configurations, the second sensor can be located at or near the second end of the dry line.

In some configurations, the control system can be located at the humidifier.

In some configurations, the first sensor can be located in the outlet of the gases source.

In some configurations, the second sensor can be located at the inlet of the chamber.

In some configurations, the second sensor can be located at or near the second end of the dry line.

In some configurations, the control system can include a humidifier controller and a gases source controller.

In some configurations, the humidifier controller can be configured to be in electrical and/or data communication with the gases source controller.

In some configurations, the reverse flow condition can be detected based at least in part on the humidifier controller being in communication with the gases source controller.

In some configurations, the gases source controller can be configured to receive a signal of the first temperature from the first sensor, the humidifier controller communicating with the gases source controller to receive the signal.

In some configurations, the pre-determined temperature threshold can be between 0.1° C. to 5° C.

In some configurations, the pre-determined temperature threshold can be 1° C. to 3° C.

In some configurations, the outputting a reverse flow condition can be further in response to a fluctuation of the second temperature exceeding a pre-determined limit.

In some configurations, the method can be performed during setup of the system or just after setup is finished. In some configurations, the method can be performed during steady state operation of the system.

In some configurations, the control system can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, a humidification system configured to detect a reverse flow condition in the humidification system can include a control system configured to: measure a first temperature indicative of a temperature of an outlet of a gases source and/or a first end of a dryline using a first sensor, the gases source in fluid communication with a breathing circuit and a humidifier, the humidifier including a heater plate and a chamber that carries humidification fluid, the chamber positionable on the base, the breathing circuit comprising an inspiratory conduit, an expiratory conduit, and the dryline; measure a second temperature indicative of a temperature of an inlet of the chamber and/or a second end of the dryline using a second sensor; compare a difference between the first temperature and the second temperature; and output a reverse flow condition in response to the difference being above a pre-determined temperature threshold.

In some configurations, the breathing circuit can also include the chamber.

In some configurations, the first sensor can be located in or near the first end of the dryline.

In some configurations, the second sensor can be located at the inlet of the chamber.

In some configurations, the second sensor can be located at or near the second end of the dry line.

In some configurations, the control system can be located at the humidifier.

In some configurations, the first sensor can be located in the outlet of the gases source.

In some configurations, the second sensor can be located at the inlet of the chamber.

In some configurations, the second sensor can be located at or near the second end of the dry line.

In some configurations, the control system can include a humidifier controller and a gases source controller.

In some configurations, the humidifier controller can be configured to be in electrical and/or data communication with the gases source controller.

In some configurations, the reverse flow condition can be detected based at least in part on the humidifier controller being in communication with the gases source controller.

In some configurations, the gases source controller can be configured to receive a signal of the first temperature from the first sensor, the humidifier controller communicating with the gases source controller to receive the signal.

In some configurations, the pre-determined temperature threshold can be between 0.1° C. to 5° C.

In some configurations, the pre-determined temperature threshold can be 1° C. to 3° C.

In some configurations, the outputting a reverse flow condition can be further in response to a fluctuation of the second temperature exceeding a pre-determined limit.

In some configurations, the dryline may not include a heater wire.

In some configurations, the dryline can be between 100 mm to 1000 mm in length.

In some configurations, the dryline can be between 300 mm to 900 mm in length.

In some configurations, the dryline can be between 400 mm to 800 mm in length.

In some configurations, the dryline can be between 500 mm to 800 mm in length.

In some configurations, the dryline can be between 500 mm to 600 mm in length.

In some configurations, the dryline can be between 700 mm to 800 mm in length.

In some configurations, the control system can generate an alarm or indication that an incorrect connection exists in the humidification system. In some configurations, the alarm or indication may be presented to a user via the user interface. The user interface may include a touchscreen or a combination of screen and buttons. The user interface may be a user interface of a humidifier, a user interface of the gases source, and/or a user interface of a patient monitoring station. The alarm may be communicated from the humidifier to the gases source and/or the patient monitoring station.

In some configurations, the controller of the humidifier may be configured to transmit a control signal to the gases source to switch off the gases source, or reduce the gases source output, or change operation of the gases source to a safe mode if a reverse flow condition is detected.

In some configurations, the controller of the humidifier may be configured to reduce power to the heater plate or control the humidifier to reduce humidity output if a reverse flow condition is detected.

In some configurations, the detecting can be performed during setup of the system or just after setup is finished. In some configurations, the detecting can be performed during steady state operation of the system.

In one configuration the dryline, the inspiratory conduit, and the expiratory conduit each have an indicia on their respective connectors indicating direction of connection. In some configurations, the connectors may have indicia that indicate the corresponding structure or element the connector of that conduit is to connect to. For example, the expiratory conduit may have indicia on one connector indicating the connector is to connect to the gases source inlet and the other end is to connect to a wye piece. The dryline can have indicia on one connector to indicate that connector is to connect to an outlet of the gases source and the other connector of the dryline can include indicia indicating the other connector connects to an inlet of the humidifier. The indicia on the connectors are preferably unique indicia to avoid confusion. The indicia may be symbols, text, images, graphics, numerals, or any combination thereof.

In some configurations, a method of detecting incorrect connections of components in a humidification system can include the steps of detecting reverse flow according to methods disclosed herein and providing an alarm or indication that an incorrect connection exists in the humidification system.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 13A-16 illustrate example setups of various mechanical structures configured to detecting incorrect flows.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Throughout this disclosure, the term "circuit" or "breathing circuit" may refer to a gases pathway that is configured to transport gases and generally includes one or more conduits that are interconnected to define a gases path. The circuit may also include a humidification chamber, which also forms part of the gases pathway.

Throughout this disclosure, the term "conduit" may refer to an individual component of a gases pathway or circuit, and may be a tube with connectors on both ends of the tube.

Throughout this disclosure, the terms "inlet," "outlet," "inspiratory conduit," "expiratory conduit," "dryline" or "dryline conduit," "patient end," "upstream," "downstream" and the like refer to the intended gases pathway coupling and normal flow direction, regardless of the actual coupling and flow direction.

Figure 1:
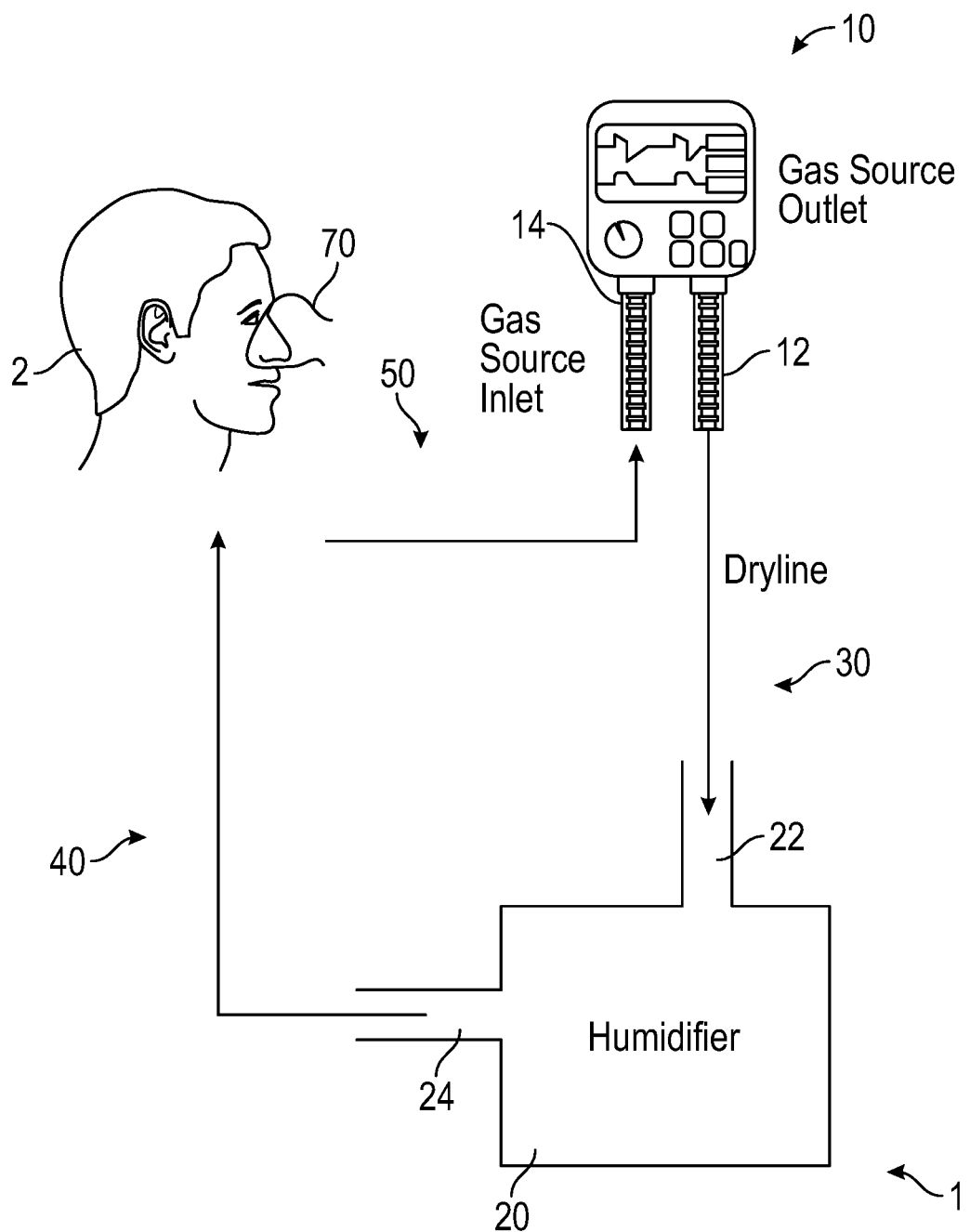
FIGS. 1 and 1A illustrate schematic representations of a dual-limb humidification system.
Figure 1A:
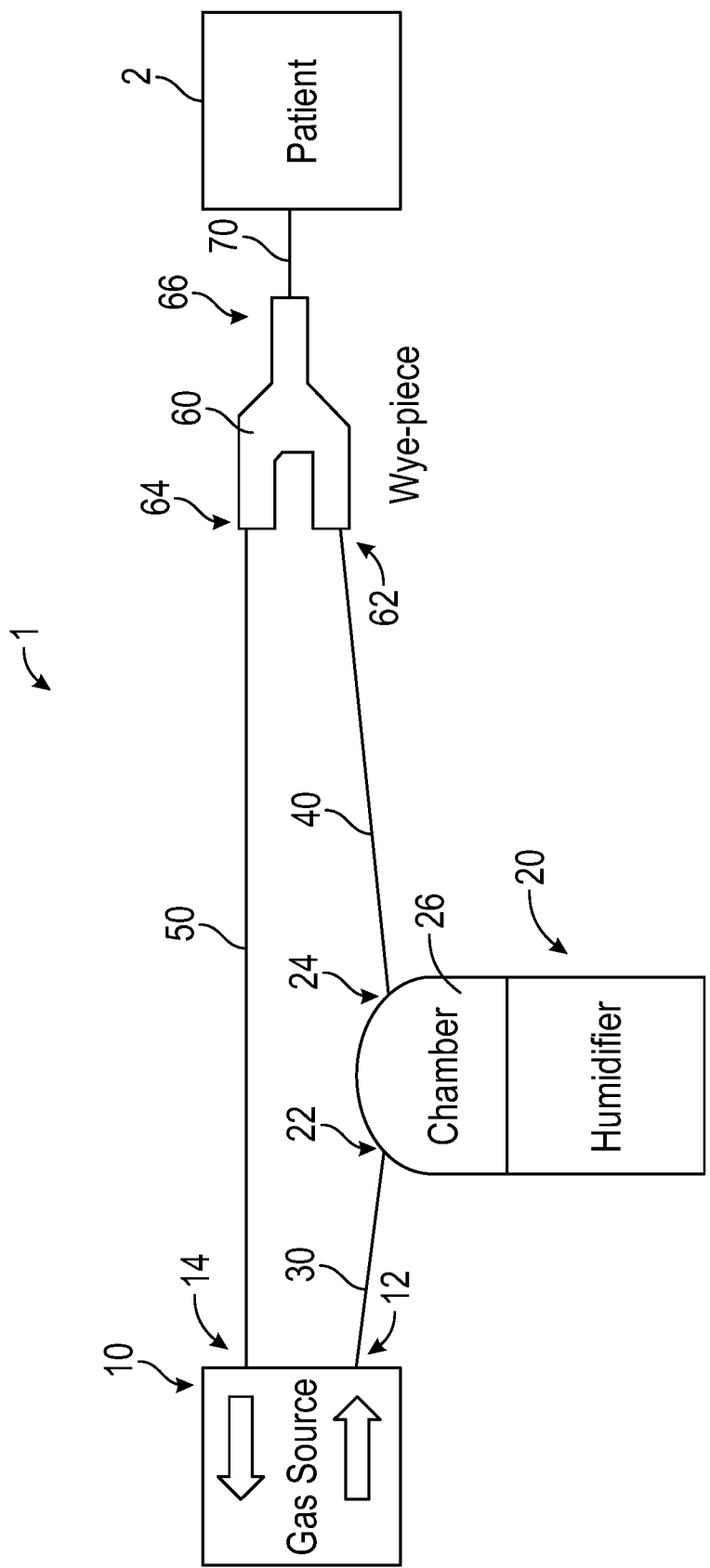

FIGS. 1 and 1A illustrate schematic representations of an example dual-limb humidification system 1. The humidification system 1 can include a gases source 10 in fluid communication with a humidifier 20 via a dryline conduit 30. In this disclosure the example of a gases source is a ventilator. Other gases sources may also be contemplated, for example, a wall gases source or a compressed gas tank. The dryline conduit 30 can be a tube that is shaped and configured to transfer gases from a gases source to the humidifier 20. The "dryline conduit refers to a conduit (for example, a tube or a corrugated tube) that is used to transport unhumidified (for example, dry or ambient) gases from the gases source to the humidifier 20. When correctly connected (that is, in an operational configuration) the dry line conduit pneumatically connects between the gases source and the humidifier. The humidifier 20 can include various components, including, for example, a chamber 26 (see FIG. 1A), and a heat source. The heat source can include a humidifier heat source that is used to heat the contents of the chamber 26 in order to vaporize the contents of the chamber 26 such that the gases flowing through the chamber can be humidified by the vaporized contents. In one example the heat source is used to heat and vaporize water to humidify the gases. The heat source also heats the gases passing through the chamber 26 to a desired temperature (for example, a therapeutic temperature). Examples of the humidifier heat source can include chemical heaters, radiant heaters, induction heaters, and the like. By way of example, the heat source can be a heater plate using a resistive heater. The humidifier 20 can also optionally include one or more processors, such as hardware and/or software processors. The humidifier 20 can include a controller that can include one or more processors and memory. The controller can control operation of the humidifier 20, for example, the steady state operation of the humidifier 20. The gases source can be single direction gases sources, blower, ventilator unit, compressed air tanks, hospital wall gases sources, oxygen bottles, or pressurized gas bottles. Some gases sources may provide gases to the patient and withdraw gases from the patient, especially when the patient is sedated to simulate breathing and to encourage gases exchange within the patient. These systems generally require an inspiratory conduit and an expiratory conduit. The gases source can also include a high flow gases source configured to deliver high flow of air or gases, for example, in excess of 30 L/min and/or up to 150 L/min. The gases source can be configured to deliver gases flow rates in other ranges e.g. for neonatal applications the flow rates can be less than 8 L/min. Gases supplied by the gases source can include either dry air, ambient air, oxygen, and/or a mixture of gases (for example, therapeutic gases or breathing gases). One or more controllers can control the gases source 10 to generate a gases flow at a desired flow rate, temperature, and/or pressure. The gases from a gases source outlet 12 can comprise dry gases.

The dry gases can be provided to a humidifier inlet 22 via the dryline conduit 30. The humidifier inlet 22 can comprise a humidifier inlet temperature sensor and/or flow sensor. The chamber 26 of the humidifier 20 can contain a liquid, such as water. The humidifier 20 can have a heat source such as a heater plate for vaporizing the water to humidify and heat the dry gases from the dryline conduit 30. Water can be supplied to the humidifier 20 from a water source. The humidified gases can leave a humidifier outlet 24 and enter an inspiratory conduit 40. The humidifier outlet 24 can comprise a humidifier outlet temperature sensor, humidity sensor, and/or flow rate sensor. The humidifier inlet 22 and outlet 24 can be the humidification chamber 26 inlet and outlet, respectively.

The inspiratory conduit 40 (that is, gases delivery conduit) can provide the humidified gases to a patient 2. The inspiratory conduit 40 can be a gas delivery conduit that carries gases from the humidifier to a patient interface 70. The inspiratory conduit 40 (that is, gas delivery conduit) can pneumatically couple the patient interface 70 and the humidifier 20. The inspiratory conduit 40 can be coupled to a patient interface 70. Although the patient 2 is illustrated as wearing a mask in FIG. 1, a person of ordinary skill in the art would appreciate from the disclosure herein that the patient 2 can be wearing other types of patient interfaces 70 disclosed herein, such as a nasal cannula or an endotracheal tube. The patient interface 70 can also comprise an interface tube, which is a short section of tube, which may be heated or unheated, and the inspiratory conduit 40 can be coupled or connected to the interface tube. The short section of tube may be a breathable tube. The short section of tube can decouple the patient interface from the inspiratory conduit to prevent the patient interface from being dislodged. Alternatively, the inspiratory conduit 40 can be coupled to a wye-piece 60 (see FIG. 1A) at an inspiratory conduit connection port 62. The wye-piece 60 can be connected to the patient interface 70 at a patient interface connection portion 66. Optionally, the inspiratory conduit 40 can include a heater. A patient interface end of the inspiratory conduit 40 can comprise a patient end temperature sensor, humidity sensor, and/or flow rate sensor. The inspiratory conduit 40 can have an inspiratory heat source to reduce or prevent condensate formation. Examples of the inspiratory conduit heat source can include a heater wire, heating tape, and/or water jacket heating. Condensate can be formed when a temperature of the humidified gases leaving the humidifier 20 drops below the dew point temperature due to heat loss when the gases travel through an unheated inspiratory conduit 40. The humidification system 1 can include an expiratory conduit 50 (that is, a gases transport conduit or expired gases transport conduit). The expiratory conduit 50 can be a gas transport conduit that directs gases away from the patient. The expiratory conduit 50 can direct expired gases away from the patient and transport the expired gases to the gases source or to some other device (for example, a vent) that may release the gases to atmosphere. The expiratory conduit 50 can direct gases expired from the patient 2 back to a gases source inlet 14. The expiratory conduit 50 can include an expiratory conduit heat source, such as a heater wire, heating tape, and/or water jacket heating. Optionally, the expiratory conduit 50 can be formed of a breathable material such that moisture within the expired gases are transferred from the expired gas to the atmosphere. In this regard, gases can be dried while travelling through the expiratory conduit 50. The expiratory conduit 50 can be coupled to the patient interface 70 via the wye-piece 60 at the expiratory conduit connection portion 64.

Sensors can be placed in various locations in the humidification system. For example, the sensors can include flow rate, pressure, temperature, and/or humidity sensors. The sensors can comprise a thermistor. The thermistor can act as a temperature sensor and can be switched to act as a flow sensor by applying a voltage to the thermistor to heat the thermistor. Output of the sensors can be received by the controllers to assist the controllers to operate the humidification system 1 in a manner that can provide optimal therapy. Other sensors that may be used include thermocouples, thermostats, semiconductor sensors, infrared sensors, and resistive temperature devices. Types of humidity sensors that may be used can include capacitive humidity sensor, chilled mirror hygrometer, dry bulb humidity sensor, wet bulb humidity sensor, and the like.

Example Incorrect Connection Conditions

Example methods of detecting incorrect flow conditions in a humidification system, such as the humidification system 1 components will now be described with respect to FIGS. 2A-D. These are examples only, and it should be appreciated that other conduit incorrect connections may be possible, such as connecting conduits backwards and/or in different locations in the circuit to where they should normally be connected. The reverse flow detection methods disclosed herein may detect or suggest one or more types of potential incorrect connections.

A control system of the humidification system can generate an alarm or indication that an incorrect connection exists in the humidification system. The alarm or indication may be presented to a user via the user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

The controller of the humidifier may be configured to transmit a control signal to the gases source to switch off the gases source, or reduce the gases source output, or change operation of the gases source to a safe mode if a reverse flow condition is detected. The controller of the humidifier may be configured to reduce power to the heater plate or control the humidifier to reduce humidity output if a reverse flow condition is detected.

Figure 2A:
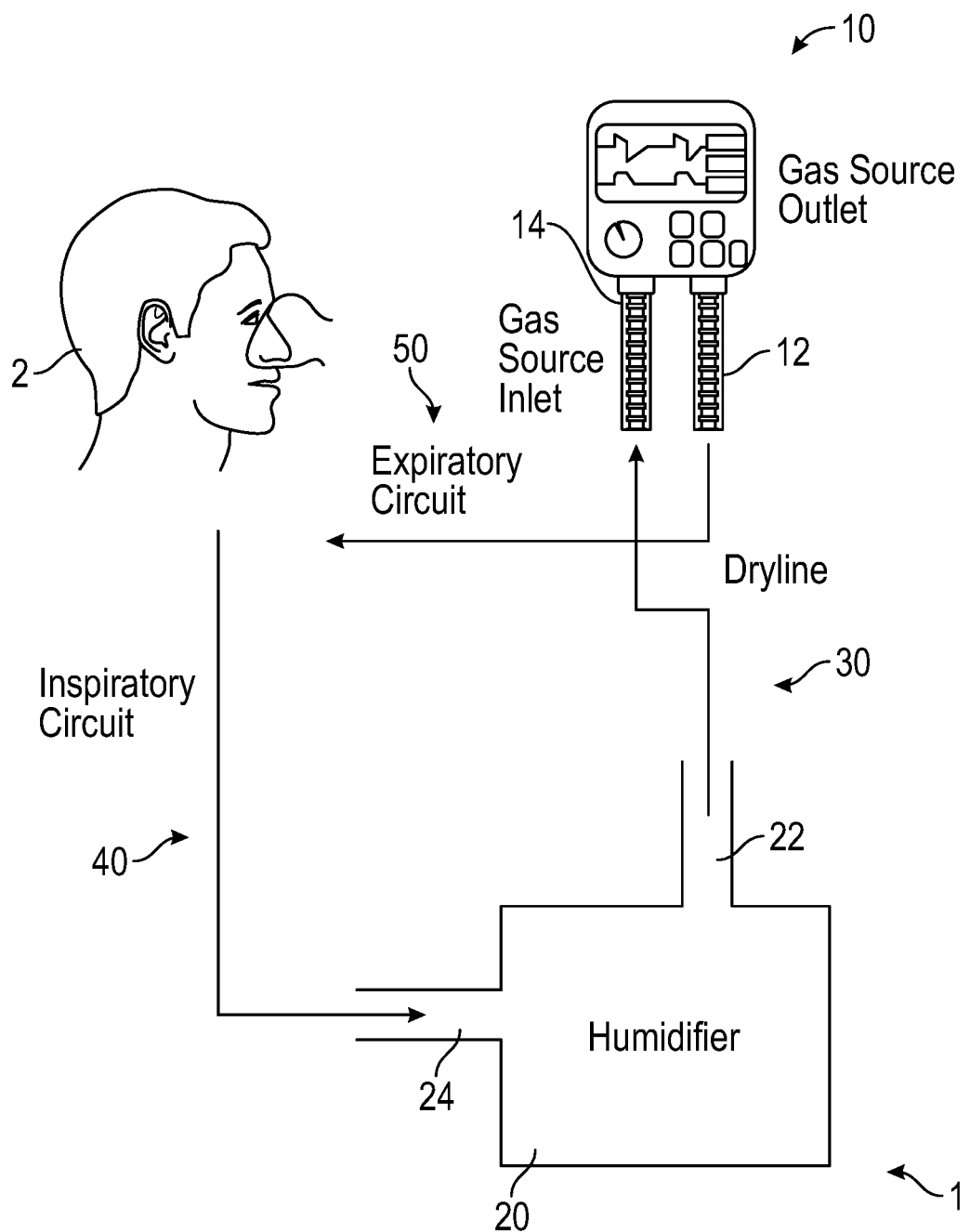
FIGS. 2A-2D illustrate example connection errors and/or incorrect connections in the humidification system of FIG. 1.

In Error 1 as shown in FIG. 2A, connections of the dryline conduit 30 and the expiratory conduit 50 with the gases source 10 are reversed. Specifically, the dryline conduit 30 is incorrectly coupled to the gases source inlet 14 and the expiratory conduit 50 is incorrectly coupled to the gases source outlet 12. As a result, the dry gases can flow directly to the patient 2 in the expiratory conduit 30 without being humidified or heated because the dry gases do not pass through the humidifier 20. The dry gases can be heated by an expiratory heat source in the expiratory conduit 50, wherein the heating is not properly regulated by the controllers. Expired gases from the patient 2 can become humidified through the humidifier 30 before returning to the gases source 10, resulting in condensation forming in the gases source 10.

Figure 2B:
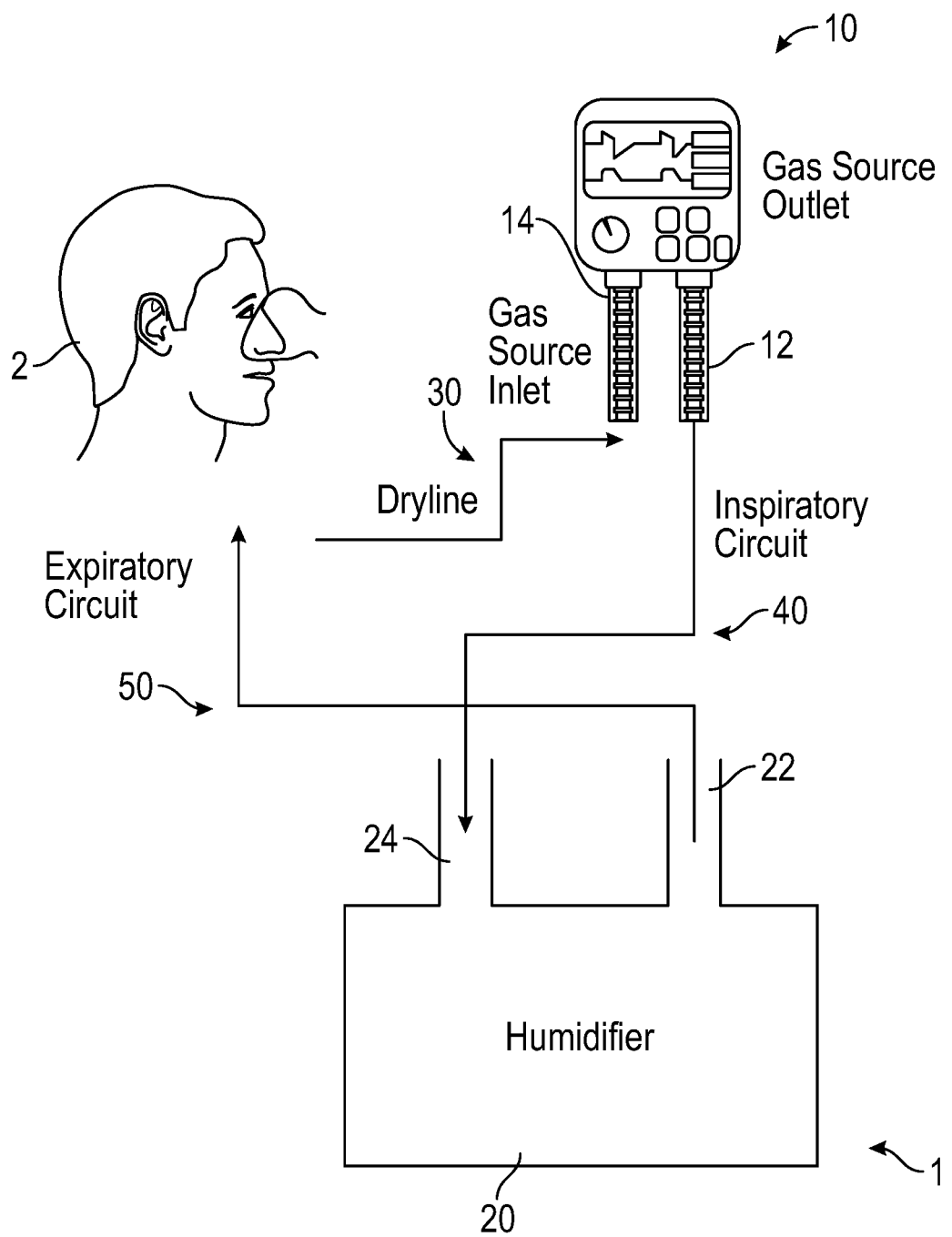

In Error 2 as shown in FIG. 2B, there is an incorrect flow condition in the humidifier 20. Specifically, the inspiratory conduit 40 is incorrectly coupled to the gases source outlet 12 and the humidifier outlet 24, rather than humidifier outlet 24 and patient 2. The expiratory conduit 50 is incorrectly coupled to the humidifier inlet port 22 and the patient 2, rather than patient 2 and gases source 10. The dryline conduit 30 is incorrectly coupled to the patient 2 and the gases source inlet 14, rather than gases source outlet 12 and humidifier inlet 22. The system receives outputs from the patient end sensor in the inspiratory conduit 40 and the sensors at the humidifier inlet and/or outlet 22, 24 that are not indicative of the actual patient end temperature, and/or inlet/outlet temperatures. The humidifier heat source and the inspiratory heat source may not function properly because of the incorrect outputs from the sensors, due to the incorrect feedback from the sensors. The gases leaving the humidifier inlet 22 for the patient 2 may not be heated because the expiratory conduit 50 may not have a heating wire, or may be heated by an expiratory conduit heat source in the expiratory conduit 50, wherein the heating is not properly regulated by the controllers. The expiratory conduit 50 transporting humidified gases from the humidifier 20 can cause the gases to lose moisture (that is, be dried out) before reaching the patient 2.

Figure 2C:
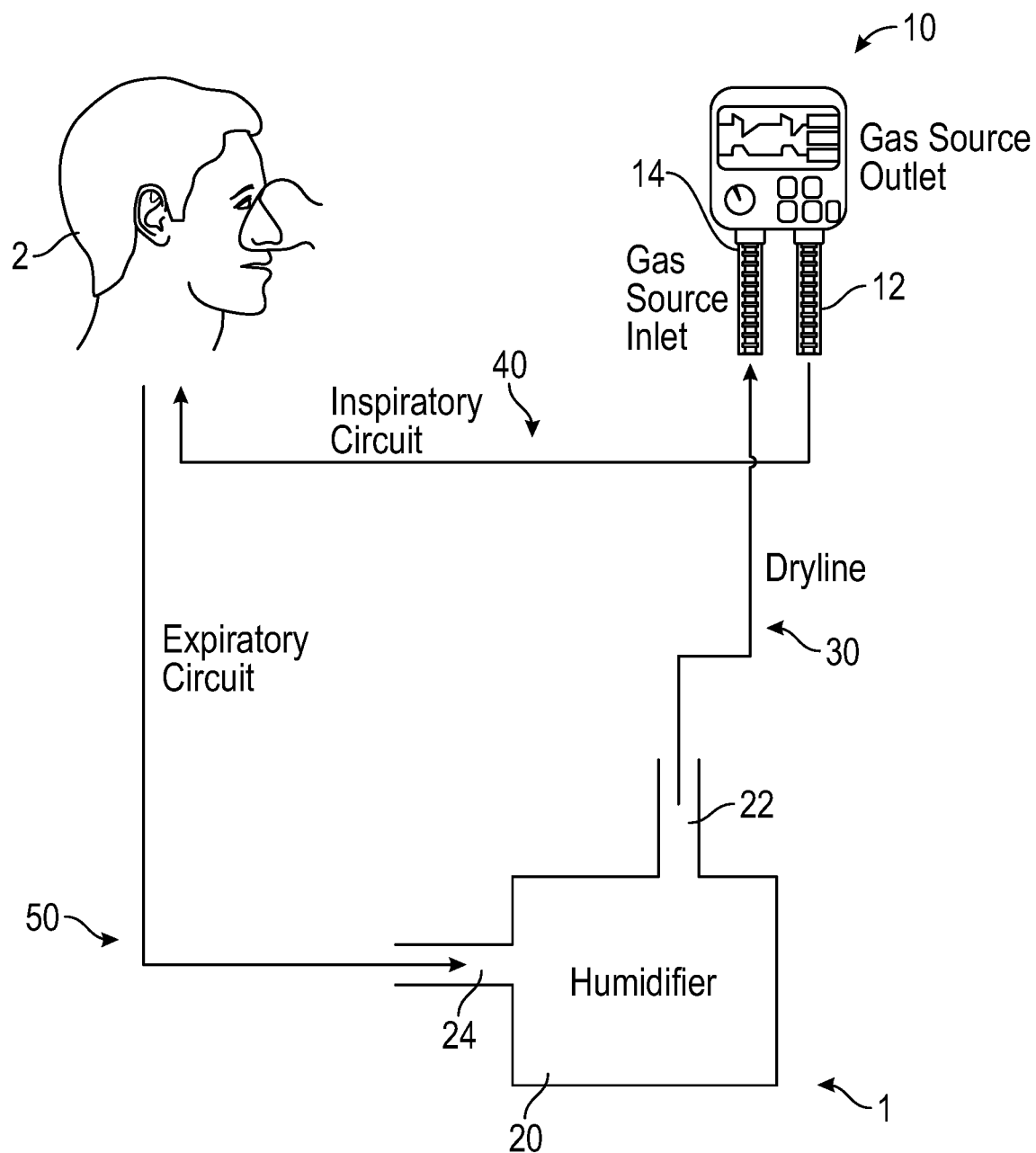

In Error 3 as shown in FIG. 2C, one of the errors includes connections of the gases source inlet 14 and outlet 12 being reversed. Specifically, the dryline conduit 30 is incorrectly coupled to the gases source inlet 14 and the humidifier inlet 22. Another error is that the expiratory conduit 50 is incorrectly coupled to the humidifier outlet 24 and the patient 2. Another error is that the inspiratory conduit 40 is incorrectly coupled to the patient 2 and the gases source inlet 12. As a result, the dry gases can flow directly to the patient 2 in the expiratory conduit 30 without being humidified or heated because the dry gases do not pass through the humidifier 20. The expired gases from the patient 2 can become humidified in the humidifier 30 before returning to the gases source 10. The configuration shown in FIG. 2C can result in humidified gases returning to the gases source without any drying of the gases. The excess moisture in the gases can potentially cause damage to the gases source due to condensation.

Figure 2D:
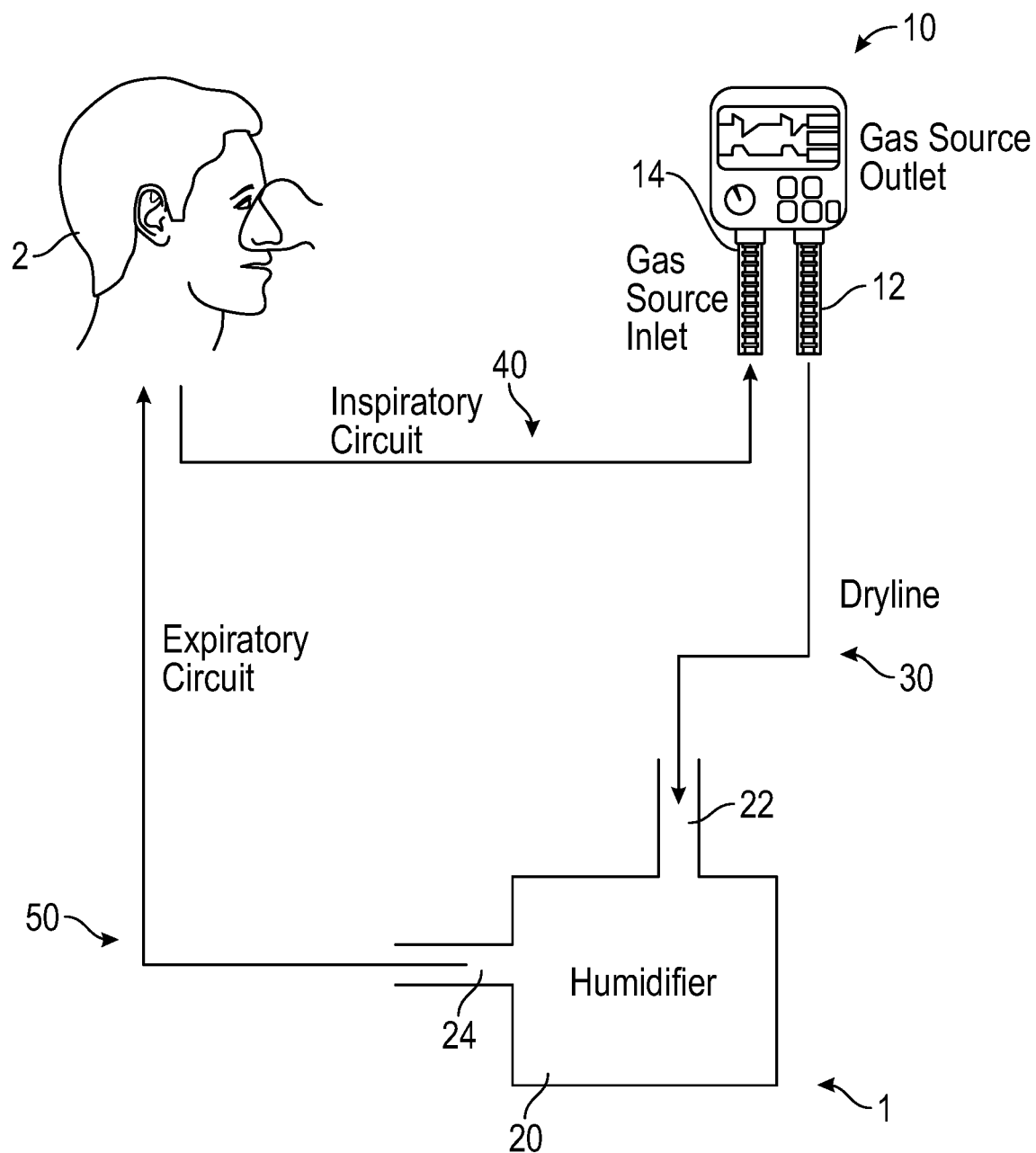

In Error 4 as shown in FIG. 2D, the gases flow in the normal direction, but there are errors in the connections. Specifically, the expiratory conduit 50 is incorrectly coupled to the humidifier outlet 24 and the patient 2. The inspiratory conduit 40 is incorrectly coupled to the gases source inlet 14 and the patient 2. That is, the inspiratory conduit 40 and expiratory conduit 50 have been switched from their intended positions in the breathing circuit. As a result, the patient end sensor in the inspiratory conduit 40 cannot properly measure the temperature of the gases delivered to the patient 2, but measures the temperature of the exhaled gases from the patient 2. The gases leaving the humidifier 20 cannot be heated to ensure that the patient end temperature reaches the patient end set-point. This can be due to the expiratory conduit 50 not having a heat source, or the expiratory conduit heat source not being properly energized by the controllers receiving the patient end temperature input from the sensor in the inspiratory conduit 40. The gases reaching the patient 2 can exceed or fall below the patient end set-point as the gases travel through the expiratory conduit 50. In the case of a breathable expiratory conduit, the gases delivered to the patient will also have sub-optimal humidity. The configuration shown in FIG. 2D can result in humidified gases delivered to the gases source 10. The inspiratory conduit 40 transporting expired gases may not be able to dry the gases like the expiratory conduit 50. Therefore, humidity can be retained in the inspiratory conduit 40 (incorrectly coupled to the gases source inlet 14 and the patient 2) and the moisture can be delivered to the gases source 10. As discussed above, this moisture can potentially cause damage to the gases source 10 due to condensation.

Processes Based on Injection of Traceable Element(s)

One or more controllers of the humidification system can detect incorrect flows in the humidification system via introduction of a traceable element or a tracer into the system. The controller can be a controller of the gases source 10 and/or the controller of the humidifier 20. Examples of a traceable element or tracer can include, for example, a dye or chemical, thermal or radiant energy, moisture, carbon dioxide, oxygen, or other gases. By injecting the traceable element into the humidification system at a first location and detecting the traceable element at a second location, a direction of flow within the humidification system can be determined. Conversely, energy or the traced particle can be removed from the gas stream to enable detection of flow direction. Examples of other tracer gases include nitrogen, argon and helium.

Figure 3:
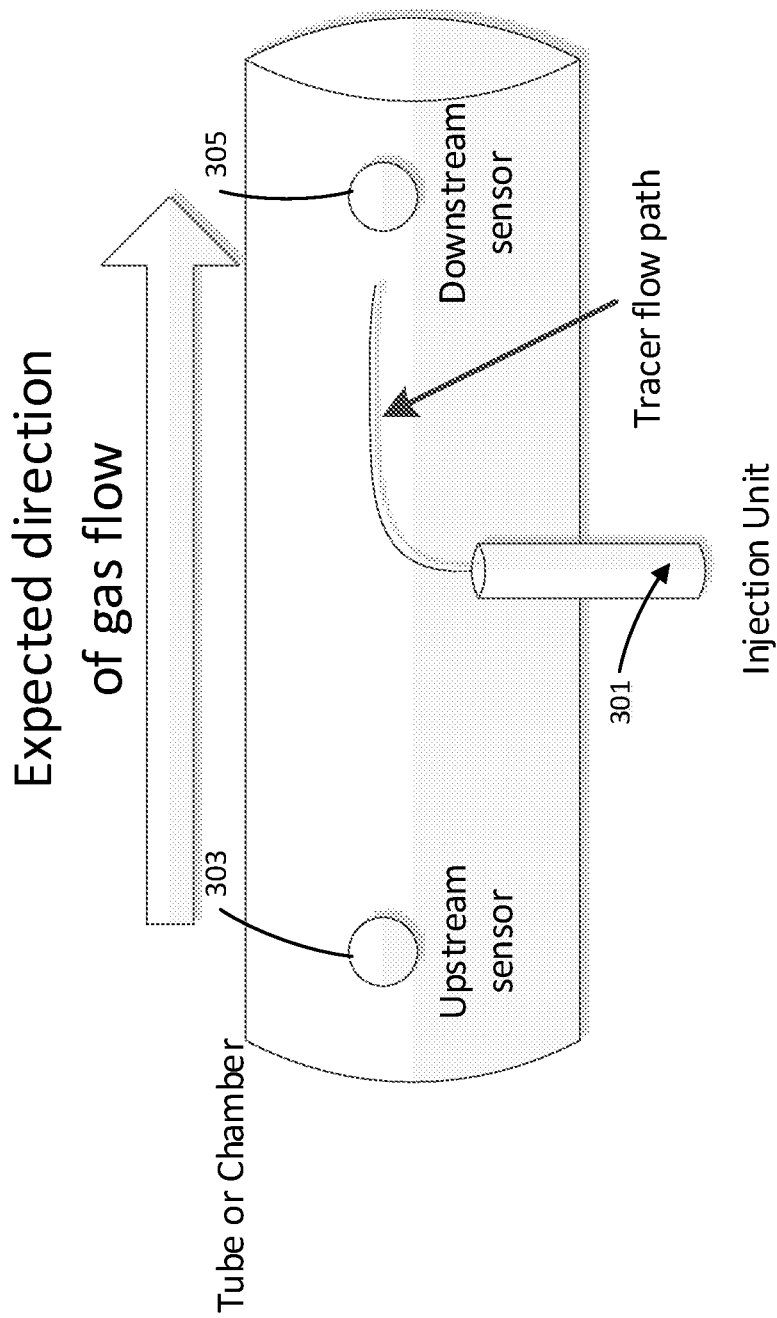
FIG. 3 illustrates an example tracer injection unit.

FIG. 3 illustrates an example tracer injection unit 301 located on a tube (such as the expiratory or inspiratory limb) or the humidifier. The direction in which a tracer flows, a tracer flow path, may indicate flow direction. Detection may be via a sensor or via visual inspection. The tracer can be introduced into the gases flow path via a humidification chamber which can be mounted or be integrally formed with the humidifier 20 or a separate injection unit within the breathing circuit, such as the inspiratory conduit. The injection unit can be integrated with any other conduit. For example, if the injection unit 301 is positioned in the inspiratory conduit then during a normal flow, the tracer can travel towards the patient interface. During an incorrect flow, for example, the tracer can flow towards the ventilator or the gases source. In some examples, the tracer injection unit may be situated in the expiratory conduit. In this regard, during a normal flow, the tracer can travel towards the ventilator or the gases source. During an incorrect flow, the tracer can flow towards the patient interface. As discussed above, the injector unit can be in the humidification chamber or positioned in any conduit such that a tracer can be used to determine an incorrect flow condition based on detecting a property of the gases or detecting the direction of flow of the tracer.

The system can utilize a suitable sensor that can detect the presence of the tracer or change in physical properties of gases flowing through the humidification system 1 (for example, temperature, pressure, humidity) from the injection of the tracer to determine the direction of flow. The location of the sensor can be downstream or upstream with respect to the location of the tracer injection unit 301. If the sensor is located upstream, the tracer will be detected in incorrect flow conditions. If the sensor is located downstream, the tracer can be detected in normal flow conditions. More than one sensor can also be positioned both downstream and upstream of the location where the tracer is introduced. For example, as shown in FIG. 3, the tube or humidifier can include an upstream sensor 303 and a downstream sensor 305. In the illustrated configuration of FIG. 3, being positioned in the inspiratory conduit, if the downstream sensor detects the tracer this is indicative of normal flow. If the upstream sensor detects the tracer this is indicative of a reverse flow condition. The occurrence of a reverse flow condition is indicative of incorrect connections in the system.

The injector unit and/or the suitable sensor(s) can be in electronic communication with a controller. The controller can be a controller of the gases source 10 or a controller of the humidifier 20. The controller can control the injector unit, for example, to instruct the operation of the injector unit. The controller can receive measurements from the sensor(s) and process the received measurements. The controller can determine a reverse flow condition and/or indication of incorrect connections. The electrical communication can be wired or wireless.

In one example the tracer can also cause another substance, material, and/or surface in the humidification system to change color, acting as a visual cue to the user. For example, a tracer of a certain pH can chemically react with the contacting inner wall of the expiratory conduit, thereby causing a visible change in color. Alternatively the sensors in the tube associated with the tracer injection unit may undergo a physical change when a tracer is detected to provide a visual indication of the flow direction, and hence provide a visual indication of potential incorrect connections. The humidification system 1 can include sensors that may include a substance that changes color when a tracer is detected.

Injection of the tracer may be during the humidification system's start-up or during therapy or interruption of therapy. The injection may be one time, periodic, intermittent, or continuous. The tracer injection unit and/or sensor can be in communication with the controllers of the humidification system. The controllers may control when the tracer is injected and/or detected. Alternatively, the tracer injection unit may control when the tracer is injected and the sensor is controlled by the controllers of the humidification system.

Processes Based on Injection of Particle

Various methods of detecting an incorrect flow condition or a normal flow condition in a humidification system, such as the humidification system 1, are shown in FIGS. 3A-3D. Moisture may be injected via external sources and/or already-present sources (for example, ambient air or exhaled air from the patient). In all the reverse flow condition and/or incorrect connection detection processes described herein, the controller of the humidifier and/or the gases source can also optionally output a warning (for example, audible, visual, haptic, or any combinations thereof) when the controller determines that incorrect flow is present. The controller can also optionally output indications to a user that incorrect flow condition is not detected or normal flow is detected. Once the controller detects an incorrect flow condition, the controller can generate an indication that an incorrect connection is present. A presence of an incorrect flow condition may be an indication of an incorrect connection. The controller may be further configured to output a signal to a user interface to display the direction of flow detected and/or display a message or alarm if a reverse flow condition is detected.

Figure 3A:
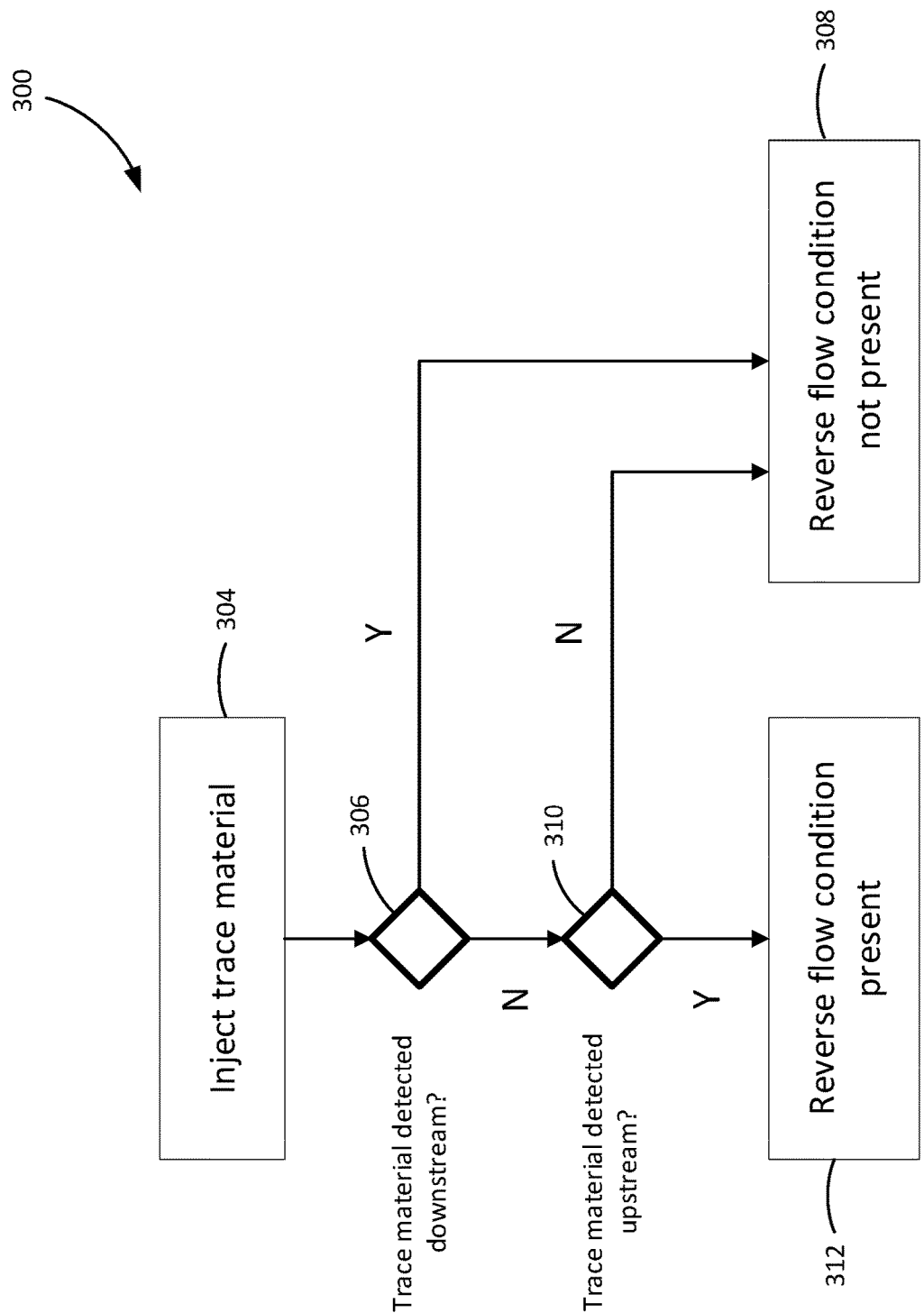
FIGS. 3A-3D illustrate example methods of detecting incorrect flows by introducing a tracer into the humidification system.

In a method 300 shown in FIG. 3A, a controller of the humidification system can begin a reverse flow detection algorithm. At step 304, the controller of the humidification system (or a separate controller, such as that of a separate injection unit) can cause traceable particle(s) (for example, a dye or chemical) to be introduced into the humidification system. At step 306, the controller can determine whether the traceable particle is detected downstream of the injection location. If the traceable particle is detected downstream by a downstream sensor, the controller can determine that there is no incorrect flow at step 308. Alternatively and/or additionally, the controller can determine whether the traceable particle is detected upstream by an upstream sensor at step 310. If the traceable particle is not detected upstream, the controller can determine that there is no incorrect flow at step 308. If the traceable particle is detected upstream, the controller can determine that there is an incorrect flow at step 312. Once the controller detects an incorrect flow condition, the controller can generate an indication that an incorrect connection is present. A presence of an incorrect flow condition may be an indication of an incorrect connection.

The suitable sensor(s) can be in electronic communication with a controller. The controller can be a controller of the gases source or a controller of the humidifier. The controller can receive measurements from the sensor(s) and process the received measurements. The controller can determine a reverse flow condition and/or indication of incorrect connections. The same controller may be in communication with the sensor(s) and for controlling the injection of the particles. The electrical communication can be wired or wireless.

Processes Based on Injection of Thermal or Radiant Energy

Figure 3B:
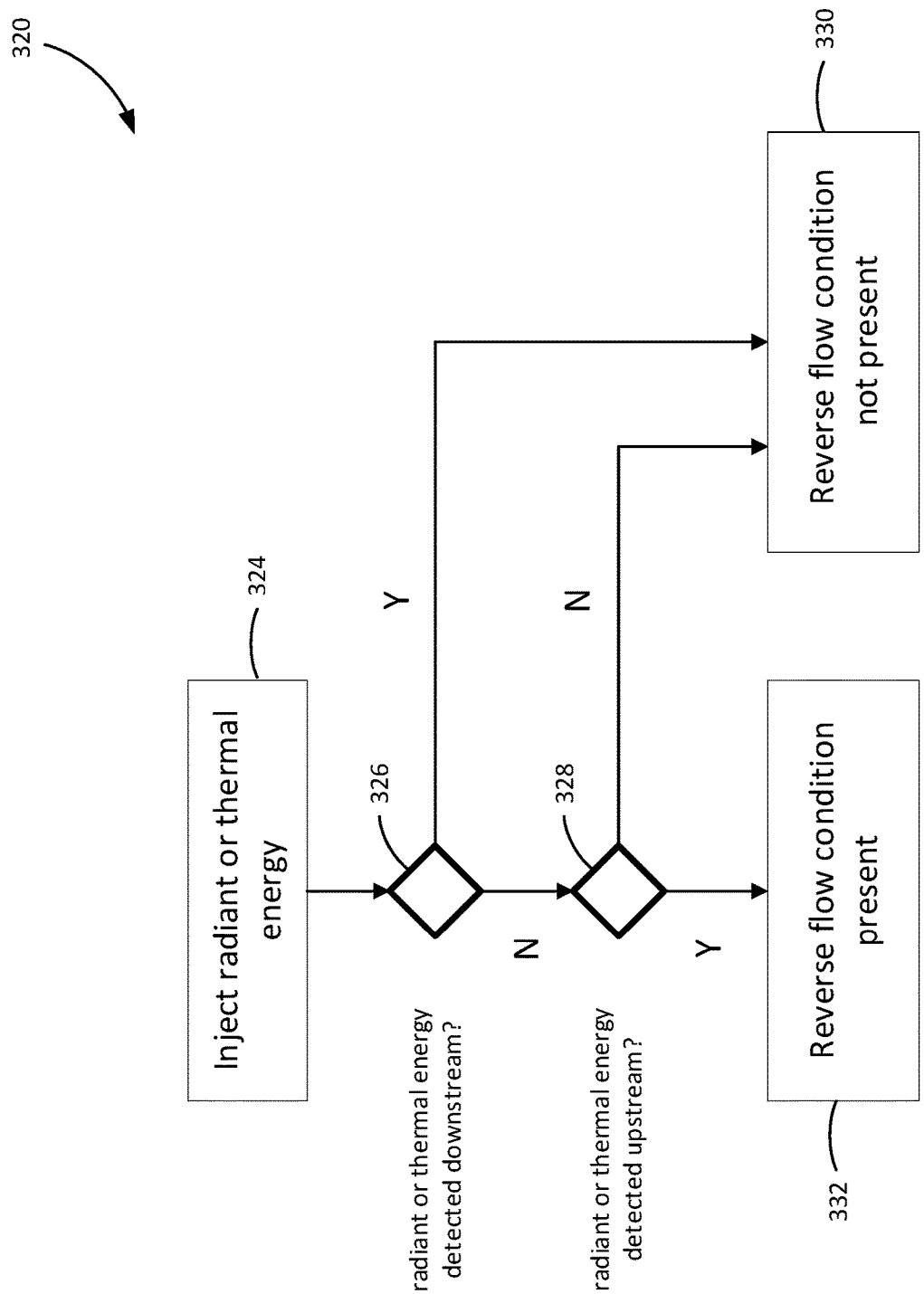

In a method 320 shown in FIG. 3B, a controller begins a reverse flow detection algorithm. At step 324, the controller can cause thermal or radiant energy to be introduced into the humidification system. For example the injection unit may be heater or heat source. At step 326, the controller of the humidification system can determine whether the injected thermal or radiant energy is detected downstream. If the thermal energy is detected downstream by a downstream sensor, the controller can determine that there is no incorrect flow at step 330. Alternatively and/or additionally, the controller can determine whether the injected thermal or radiant energy is detected upstream by an upstream sensor at step 328. If the injected thermal or radiant energy is not detected upstream, the controller can determine that there is no incorrect connection at step 330. If the injected thermal or radiant energy is detected upstream, the controller can determine that there is incorrect flow and/or at step 332. Once the controller detects an incorrect flow condition, the controller can generate an indication that an incorrect connection is present. A presence of an incorrect flow condition may be an indication of an incorrect connection. The methods shown in FIGS. 3A and 3B can be executed by a system that includes an injection unit, an upstream sensor and a downstream sensor, similar to the illustrated configuration of FIG. 3. In one example the injection unit and the sensors are located in the inspiratory conduit or adjacent an outlet of the humidification chamber. This arrangement allows sensing to be conducted in a dual limb or single limb gases delivery system. A detection of a reverse flow condition can be displayed to a user on a user interface or an alarm can be communicated to a user as a reverse flow condition is indicative of incorrect connections. The detection of a reverse flow condition can also act as a detection of incorrect connections within the gases delivery system.

The injector unit and/or the suitable sensor(s) can be in electronic communication with a controller. The controller can be a controller of the gases source or a controller of the humidifier. The controller can control the injector unit, for example, to instruct the operation of the injector unit. The controller can receive measurements from the sensor(s) and process the received measurements. The controller can determine a reverse flow condition and/or indication of incorrect connections. The electrical communication can be wired or wireless.

Processes Based on Injection of Water

For at least this section, water can include moisture. An incorrect flow condition can be detected by injecting water and detecting a change in humidity at different locations of the humidification system and/or ventilator. Injection of water can include injecting from external and already present water sources (for example, the humidification chamber, or exhalation from the patient). The water injected may be liquid water or vapor, for example the water may be a mist or small droplets that are injected or water vapor. The injection unit would be configured to deliver water into the gases flow path. One or more humidity sensors may be positioned downstream of the water source. The humidity sensor may be any type of sensor that detects the presence of water molecules or the change of a property due to the presence of water, for example, capacitance sensors. In positions downstream of the water source, humidity may be expected to be higher and/or correlate to the water temperature. If the controller of the humidification system determines that humidity measured by the downstream humidity sensor is lower than expected and/or does not increase when the heater plate energizes, the controller can determine that there is incorrect flow. Examples of locations where the downstream humidity sensor may be placed include, but are not limited to, humidifier outlet, inspiratory conduit inlet, any location within the inspiratory conduit, inspiratory conduit outlet, the wye-piece, and the like. Once the controller detects an incorrect flow condition, the controller can generate an indication that an incorrect connection is present. A presence of an incorrect flow condition may be an indication of an incorrect connection.

The humidity sensors can be placed in the expiratory conduit. During normal flow conditions, the expiratory conduit inlet can measure the humidity of a patient's expired gas as well as humidity from the humidifier, which can typically range from 37° C. dew point or lower. However, when in incorrect flow conditions, the humidity measured in the expiratory conduit can be much lower as the expiratory conduit is incorrectly provided upstream of the patient. In particular, the humidity will be much lower where the expiratory conduit is used as a dryline (that is, between the gases source outlet and the humidifier).

The injector unit and/or the humidity sensor(s) can be in electronic communication with a controller. The controller can be a controller of the gases source or a controller of the humidifier. The controller can control the injector unit, for example, to instruct the operation of the injector unit. The controller can receive measurements from the sensor(s) and process the received measurements. The controller can determine a reverse flow condition and/or indication of incorrect connections. The electrical communication can be wired or wireless.

Figure 3C:
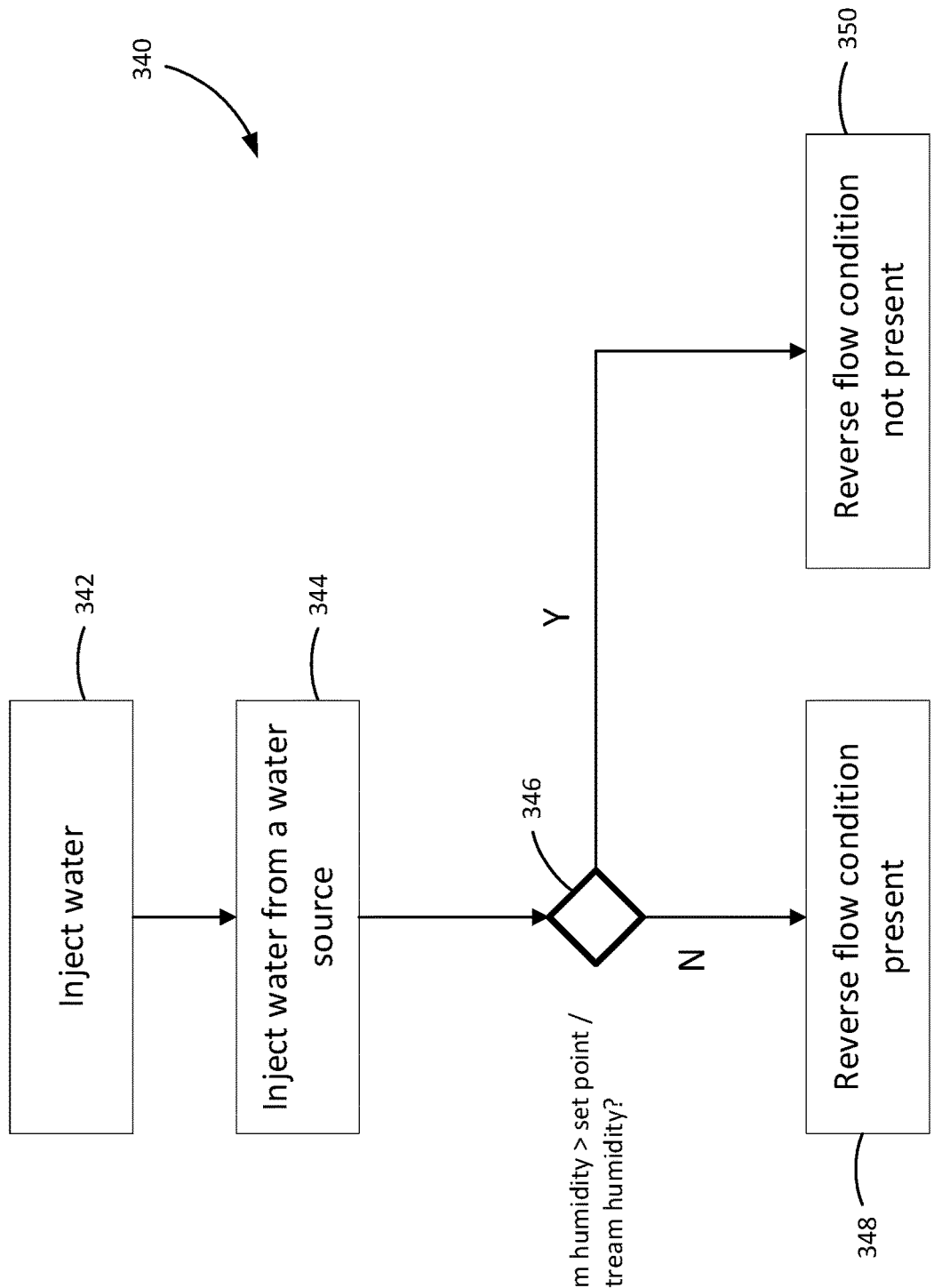
Figure 3D:
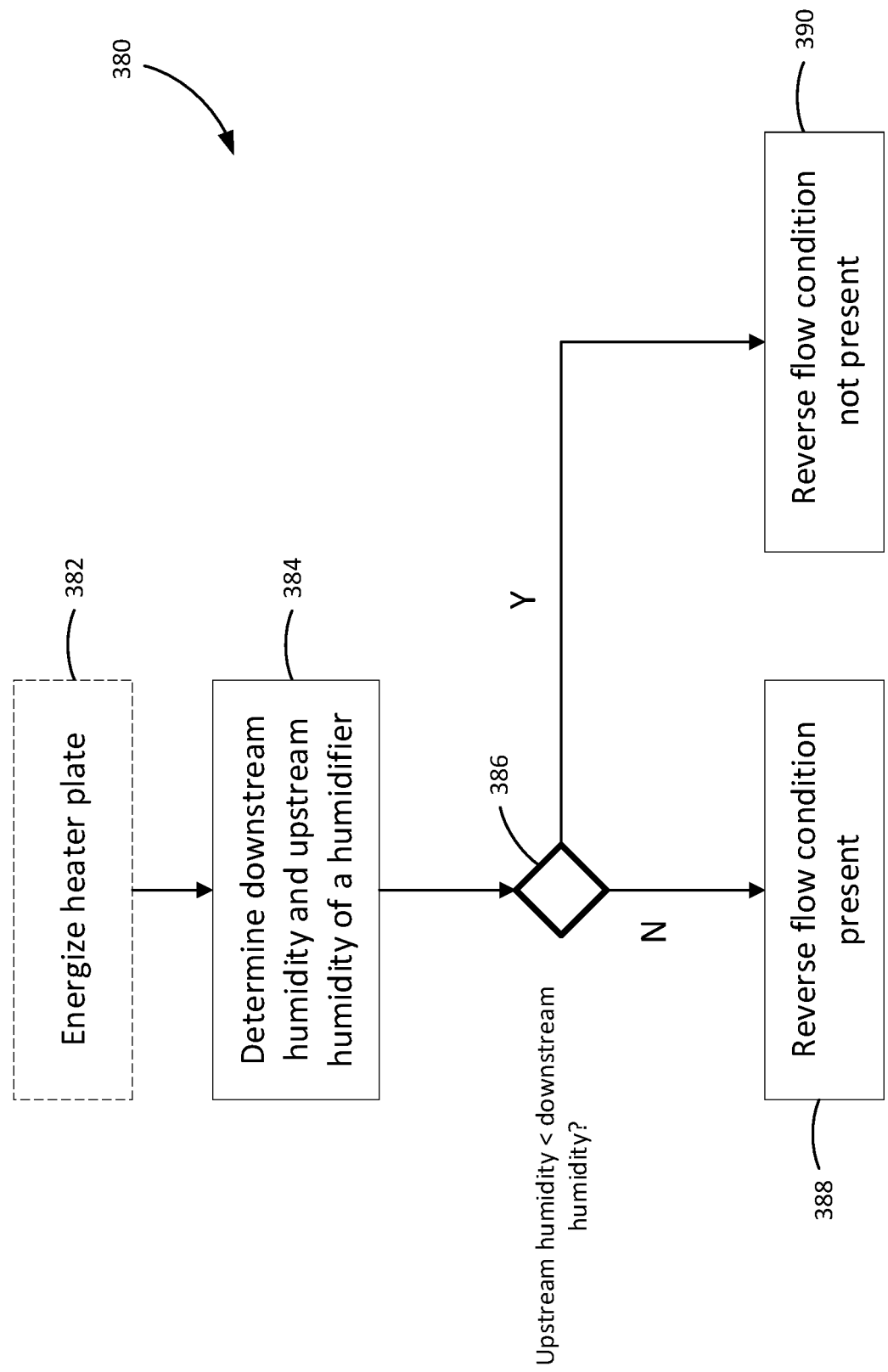

In a method 340 shown in FIG. 3C, a controller of the humidification system can begin a reverse flow detection algorithm. The detection of a reverse flow condition is indicative of incorrect connections. At step 344, the controller can cause water to be introduced into the humidification system at an injection location. At step 346, the controller of the humidification system can determine whether a downstream humidity detected by a sensor downstream from the injection location is greater than a set point and/or than an upstream humidity detected by an upstream sensor. If the downstream humidity is greater than the set-point and/or the upstream humidity, the controller can determine that there is no incorrect flow at step 350. If the downstream humidity is no greater than the set-point and/or the upstream humidity, the controller can determine that there is incorrect flow at step 348. Once the controller detects an incorrect flow condition, the controller can generate an indication that an incorrect connection is present. A presence of an incorrect flow condition may be an indication of an incorrect connection.

Upstream humidity can also be determined and compared to a predetermined set-point. For example, a humidity sensor may be positioned upstream of a water source. In positions upstream of the water source, humidity may be expected to be low and/or not correlate to the water temperature. If the controller of the humidification system determines that an upstream humidity detected by an upstream humidity sensor is higher than expected and/or increases when the heater plate energizes (thus resulting in a rise in water temperature), the controller of the humidification system can determine that there is incorrect flow. Once the controller detects an incorrect flow condition, the controller can generate an indication that an incorrect connection is present. A presence of an incorrect flow condition may be an indication of an incorrect connection.

Both downstream humidity and upstream humidity of the humidifier can be used to determine whether there is incorrect flow in the humidification system. Humidity may be generated when heater plate power is applied, resulting in a rise in water temperature. Humidity may also be generated when dry gas passes over the water in the humidifier. In a method 380 shown in FIG. 3D, a controller of the humidification system can begin a reverse flow detection algorithm. At step 384, the controller of the humidification system determines a downstream humidity of a humidifier using a downstream humidity sensor and an upstream humidity of the humidifier using an upstream humidity. At step 386, the controller determines if the upstream humidity is less than the downstream humidity. If the upstream humidity is higher than the downstream humidity, the controller of the humidification system can determine that there is incorrect flow at step 388. Conversely, the controller can determine that there is no incorrect flow at step 390 if the upstream humidity is less than the downstream humidity, as expected. Once the controller detects an incorrect flow condition, the controller can generate an indication that an incorrect connection is present. A presence of an incorrect flow condition may be an indication of an incorrect connection.

The heater plate can optionally be energized, for example, at step 382, to increase detection reliability in presence of alternate humidity source, such as a patient or room entrained (via ventilator) humidity. The controller may delay before proceeding to step 384, due to the thermal inertia of the volume of water in the humidifier. Alternatively, the delay may be omitted if the controller is configured to monitor a corresponding rise in humidity over a predetermined period of time by, for example, comparing a derivative of the two sensor readings as the water is heated. The humidity sensors can be placed anywhere upstream and downstream (in the expected gases flow path) of the water source (for example, the humidifier) or multiple water sources. Example upstream and downstream sensor locations include, but are not limited to, the humidifier inlet and outlet; the humidifier inlet and patient end of the inspiratory conduit, the dryline and the humidifier outlet, the dryline and the patient end of the inspiratory conduit, the dryline and the expiratory conduit, or others.

Processes Based on $CO_2$ or Other Gases Detection

Figure 4:
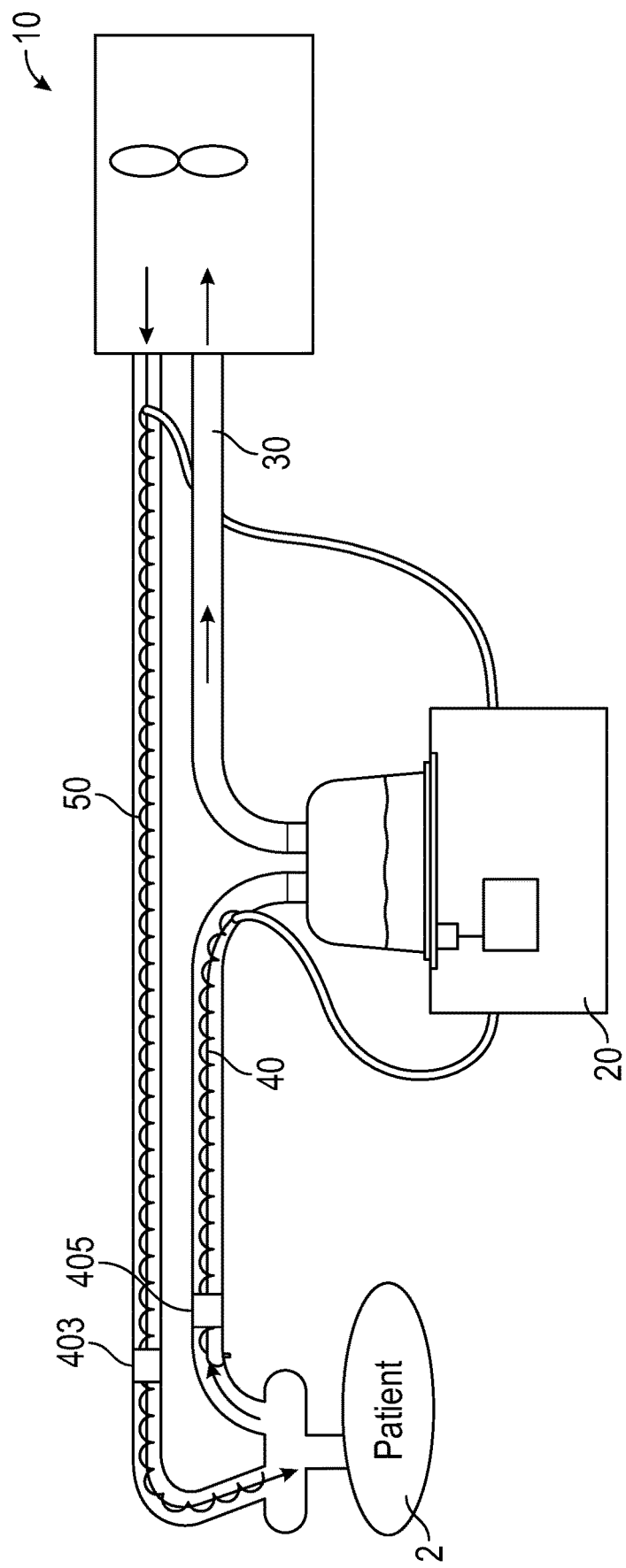
FIG. 4 illustrates an example setup for detecting incorrect condition using CO2 sensors.

Carbon Dioxide ($CO_2$) is exhaled from a patient. A $CO_2$ sensor detecting the presence of $CO_2$ within the inspiratory conduit of the breathing circuit (including the humidifier) can indicate incorrect flow in the humidification system. FIG. 4 illustrates an example setup for detecting reverse flow conditions. In some examples, the setup can include a sensing arrangement or a sensing apparatus that can detect $CO_2$. The sensing arrangement or sensing apparatus can include one or more $CO_2$ sensors 403, 405. The sensor 403, 405 can be located in either the inspiratory conduit 40 or the expiratory conduit 50, as shown in FIG. 4. A single sensor or a pair of sensors can be fitted into a cuff or connector of the inspiratory conduit 40 or expiratory conduit 50 or both. Alternatively or optionally, the sensor 403, 405 may be moulded into the conduits. The conduits can include wires to power the sensor or sensors and transmit signals from the sensor or sensors to the controller.

If a single $CO_2$ sensor is used in the inspiratory conduit (for example, adjacent the patient interface or adjacent the patient end of the inspiratory conduit), the $CO_2$ sensor can detect the presence of $CO_2$. If the sensor detects $CO_2$ above a threshold, this can be indicative of a reverse flow condition since the patient is expiring into the inspiratory conduit. This can also be indicative of incorrect connections.

Alternatively, if a single $CO_2$ sensor is used in the expiratory conduit, then the sensor can again be positioned adjacent the patient end of the expiratory conduit. In this example if the $CO_2$ sensor detects a $CO_2$ value below a threshold this can be indicative or a reverse flow condition because fresh gases are being transported through the expiratory conduit. As discussed above, this can also be indicative of incorrect connections.

In the example as per the illustrated embodiment where two sensors are used one upstream and one downstream, the controller can receive $CO_2$ readings from both sensors and compares them. If the inspiratory conduit (that is, upstream) $CO_2$ sensor detects a $CO_2$ reading higher than the $CO_2$ reading by the expiratory conduit $CO_2$ sensor then this can be indicative or a reverse flow condition. This can be indicative of incorrect connections. The controller can communicate with a user interface (for example, a user interface of the humidifier, the gases source, or a patient monitoring station) to raise an alarm.

Only one of the upstream sensor 403 and the downstream sensor 405 may be sufficient to detect an incorrect flow condition. Both sensors 403, 405 can be present. Alternatively and/or additionally, the $CO_2$ sensor can be placed anywhere upstream of the patient, including but not limited to, the humidifier inlet, humidifier outlet, inside the humidifier, and the dryline. Alternatively, a $CO_2$ sensor may be positioned in the expiratory conduit such that it can detect $CO_2$ during normal flow conditions, but may not detect elevated $CO_2$ levels in an incorrect flow condition. The $CO_2$ sensor can also be placed anywhere downstream of the patient. To improve detection of $CO_2$, the sensors can be placed both downstream and upstream of the patient. The $CO_2$ sensor can detect carbon dioxide in the expired air using various chemicals sensitive to the presence of carbon dioxide on a substrate, such as cellulous filter paper (for example, Whatman paper).

The CO2 sensor(s) can be in electronic communication with a controller. The controller can be a controller of the gases source or a controller of the humidifier. The controller can receive measurements from the $CO_2$ sensor(s) and process the received measurements. The controller can determine a reverse flow condition and/or indication of incorrect connections as described herein. The electrical communication can be wired or wireless.

Figure 4A:
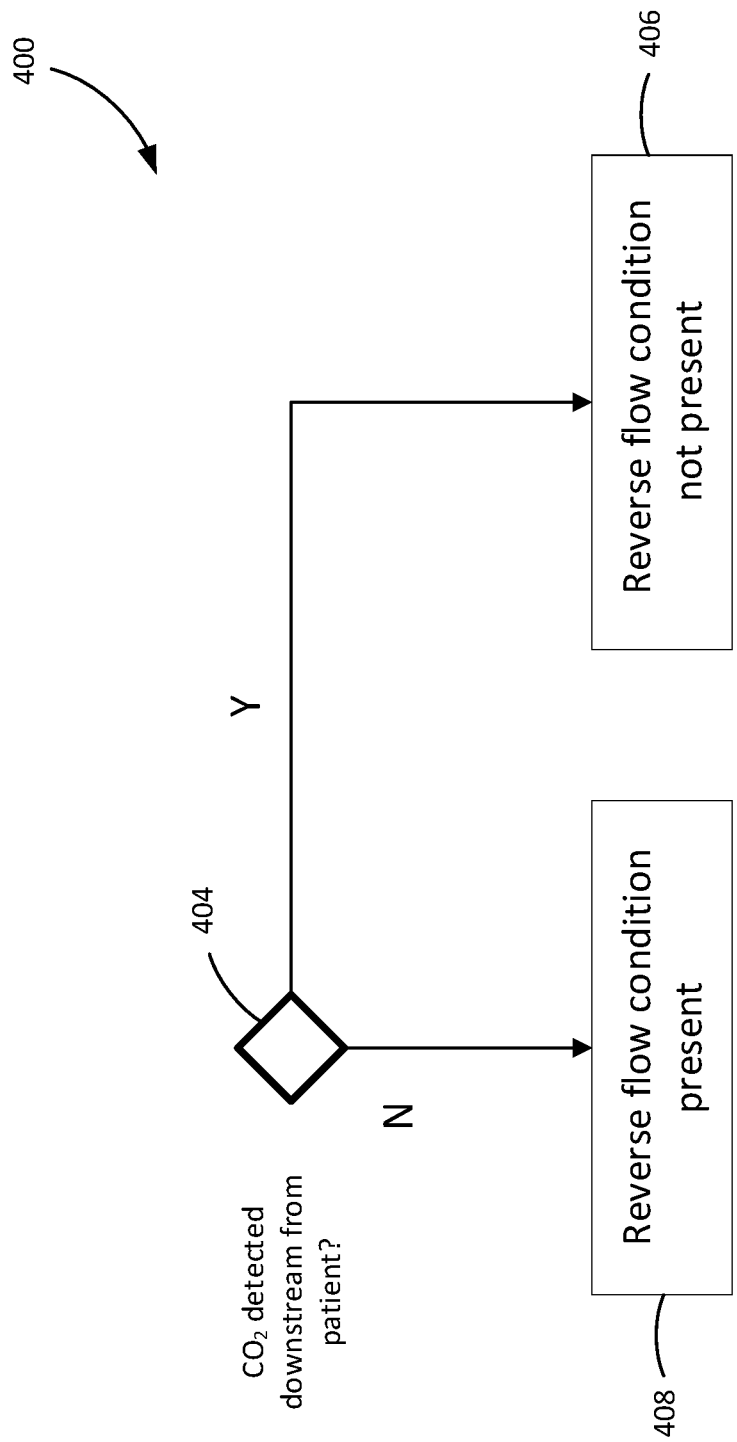
FIGS. 4A-4C illustrate example methods of detecting incorrect flows by detecting properties of gases.

In a method 400 shown in FIG. 4A, a controller of the humidification system can begin a reverse flow detection algorithm. At step 404, the controller of the humidification system can determine whether $CO_2$ is detected downstream from a patient by a downstream $CO_2$ sensor. The downstream $CO_2$ sensor can be, for example, located in the expiratory conduit 50. If $CO_2$ is detected downstream from the patient interface, the controller can determine that there is no incorrect flow at step 406. If $CO_2$ is not detected downstream from the patient interface, the controller can determine that there is incorrect flow at step 408.

Figure 4B:
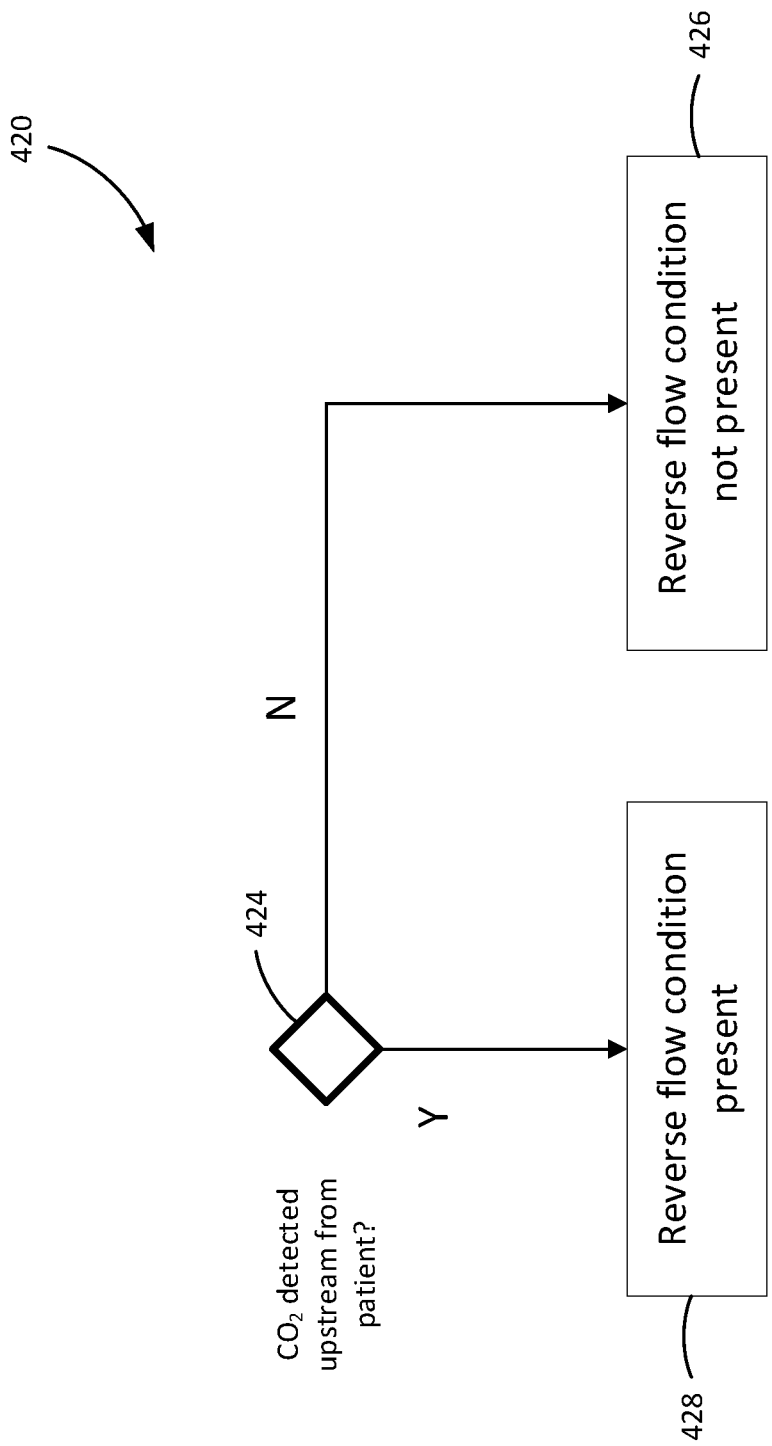

Presence of $CO_2$ upstream from the patient can also be used to indicate incorrect flow in the humidification system. In a method 420 shown in FIG. 4B, the controller can begin a reverse flow detection algorithm. The controller can determine whether $CO_2$ is detected upstream of the patient at step 424. A $CO_2$ sensor can be located, for example, in the inspiratory conduit 40. If $CO_2$ is detected upstream of the patient, the controller can determine that there is incorrect flow at step 428. If $CO_2$ is not detected upstream of the patient, the controller can determine that there is no incorrect flow at step 426.

The controller can also optionally compare an upstream $CO_2$ concentration relative to the patient to downstream $CO_2$ concentration relative to the patient. For example, a gas composition analyzer or other types of sensors can calculate carbon dioxide concentrations in a gases flow. If the upstream $CO_2$ concentration is greater than the downstream $CO_2$ concentration, the controller can determine that there is incorrect flow in the humidification system. On the other hand, if the upstream $CO_2$ concentration is less than the downstream $CO_2$ concentration, the controller can determine that there is no incorrect flow.

Processes Based on Removal of Oxygen or Other Gases

Oxygen ($O_2$) is consumed by the patient. When a normal flow condition is present, the oxygen concentration is lower downstream of the patient compared with upstream of the patient because the patient inhales a portion of the oxygen supplied by the gases source. Furthermore, the oxygen concentration is decreased downstream of the patient due to the patient exhaling $CO_2$.

An $O_2$ sensor detecting $O_2$ within the inspiratory section of the breathing circuit (including the humidifier) can indicate incorrect flow in the humidification system. The $O_2$ sensor can be placed at various locations anywhere upstream of the patient including, but not limited to, the humidifier inlet, the humidifier outlet, inside the humidifier, the dryline, and the like. Such $O_2$ sensor may detect a higher level of $O_2$ during normal flow conditions, but a reduced level of $O_2$ during incorrect flow conditions. An $O_2$ sensor can additionally, or alternatively, be placed anywhere downstream of the patient, such as in the expiratory conduit. Such $O_2$ sensor may detect reduced level of $O_2$ during normal flow conditions, but a higher level of $O_2$ during incorrect flow conditions. To improve detection, sensors can be placed at both downstream and upstream of the patient.

Figure 7:
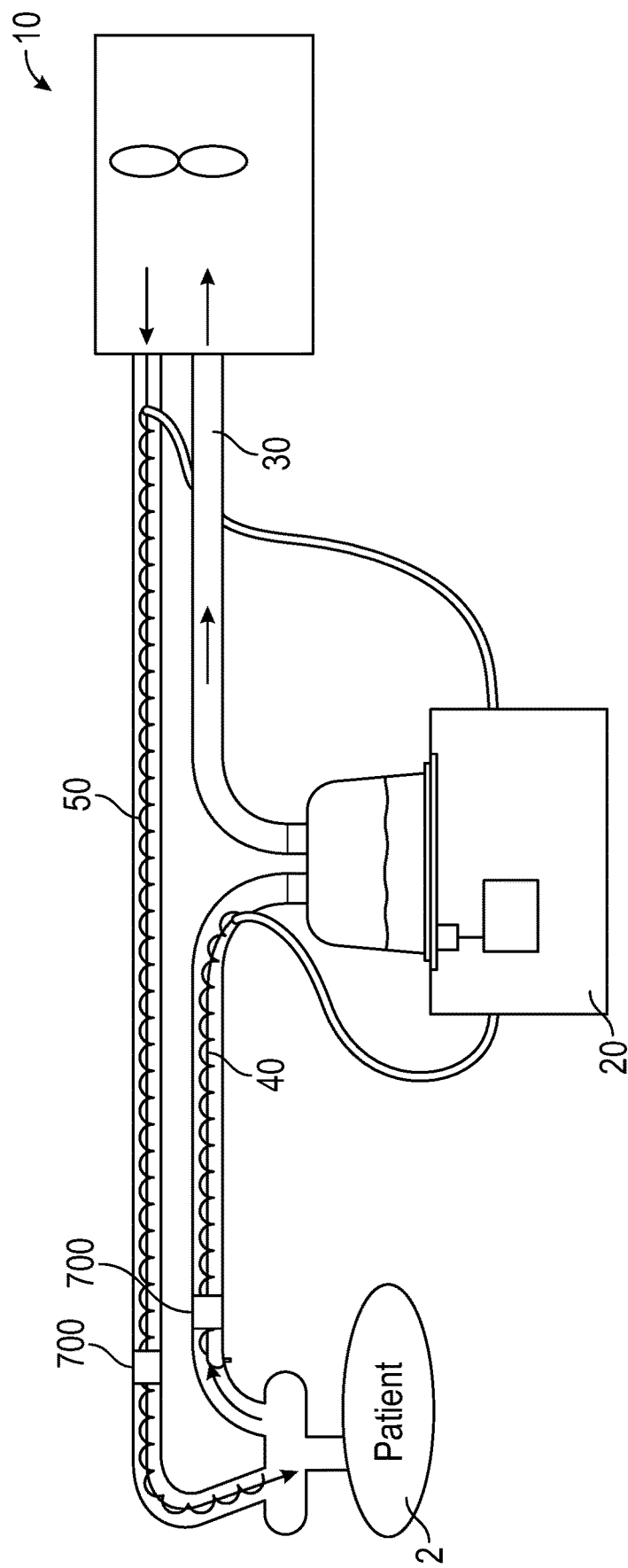
FIG. 7 illustrates an example setup for detecting incorrect flows using oxygen concentration measurements in a humidification system.

As shown in FIG. 7, a humidification can include a gases source (also referred to as a ventilator) 10 in fluid communication with a humidifier 20 via a dryline conduit 30. The humidifier 20 can include various components, including, for example, a chamber, and a heat source. The humidifier 20 can also optionally include one or more processors, such as hardware and/or software processors. The humidifier 20 can include a controller that can include one or more processors and memory. The controller can control operation of the humidifier 20. Humidified gases can leave the humidifier 20 and enter an inspiratory conduit 40. The inspiratory conduit 40 (that is, gases delivery conduit) can provide the humidified gases to a patient 2. The patient interface can also comprise an interface tube, which is a short section of unheated tube, and the inspiratory conduit 40 can be coupled or connected to the interface tube. Optionally, the inspiratory conduit 40 can include a heater. The humidification system 1 can include an expiratory conduit 50. The expiratory conduit 50 can be a gas transport conduit that directs gases away from the patient 2. The expiratory conduit 50 can direct expired gases away from the patient and transport the expired gases to the gases source (or to some other device (for example, a vent) that may release the gases to atmosphere). The expiratory conduit 50 can direct gases expired from the patient 2 back to a gases source inlet.

As shown in FIG. 7, when an incorrect flow condition is present, the gases can travel through the expiratory conduit 50 to the patient. Therefore, the concentration of $O_2$ can be higher in the expiratory conduit 50 in an incorrect flow condition than when a normal flow condition is present. An oxygen sensor 700 can be placed downstream of the patient with respect to the normal flow direction (for example, in the expiratory conduit 50) to detect the presence of or measure the concentration of oxygen. If the concentration of the oxygen downstream of the patient with respect to the normal flow direction (for example, in the expiratory conduit 50) exceeds a threshold concentration value, then an incorrect flow condition can be present. As discussed above, a controller of the humidifier 20 or a controller of the gases source can determine that a reverse flow condition is present based at least on the presence or the concentration of oxygen determined by an oxygen sensor 700. The controller can receive electronic signals indicative of presence or concentration of oxygen.

Additionally or alternatively, an oxygen sensor 700 may be placed upstream of the patient (for example, in the inspiratory conduit 40). When an incorrect flow condition is present, gases exhaled by the patient can travel from the patient towards the humidifier. This can reduce the concentration of oxygen in the humidifier 20, inspiratory conduit 40 and dryline conduit 30. If the oxygen concentration measured by an oxygen sensor located downstream of the patient goes below a threshold, then an incorrect flow condition can be present.

Optionally, the system can include a sensing arrangement or a sensing apparatus for sensing $O_2$ concentration downstream and upstream of the patient. The sensing arrangement or sensing apparatus can include two oxygen sensors 700 respectively placed downstream and upstream of the patient, such as shown in FIG. 7. FIG. 7 illustrates two oxygen sensors 700 measuring oxygen concentration level downstream and upstream of a patient. In this regard, if oxygen concentration measured by a downstream oxygen sensor is greater than a threshold and/or oxygen concentration measured by an upstream $O_2$ sensor is below another threshold, then an incorrect flow condition can be present. Another way of detecting reverse flow using two $O_2$ sensors can be monitoring the difference between the readings of the downstream and upstream $O_2$ sensors. If the upstream sensor does not detect a higher concentration than the downstream sensor, then an incorrect flow condition can be present. This is because concentration of $O_2$ downstream the patient (in the inspiratory path) can be higher than the concentration of $O_2$ upstream the patient during incorrect flow conditions. However, in normal flow conditions, concentration of $O_2$ downstream from the patient (in the expiratory limb) can be lower than concentration of $O_2$ upstream from the patient.

The $O_2$ sensor(s) can be in electronic communication with a controller. The controller can be a controller of the gases source or a controller of the humidifier. The controller can receive measurements from the $O_2$ sensor(s) and process the received measurements. The controller can determine a reverse flow condition and/or indication of incorrect connections as described herein. The electrical communication can be wired or wireless.

Figure 4C:
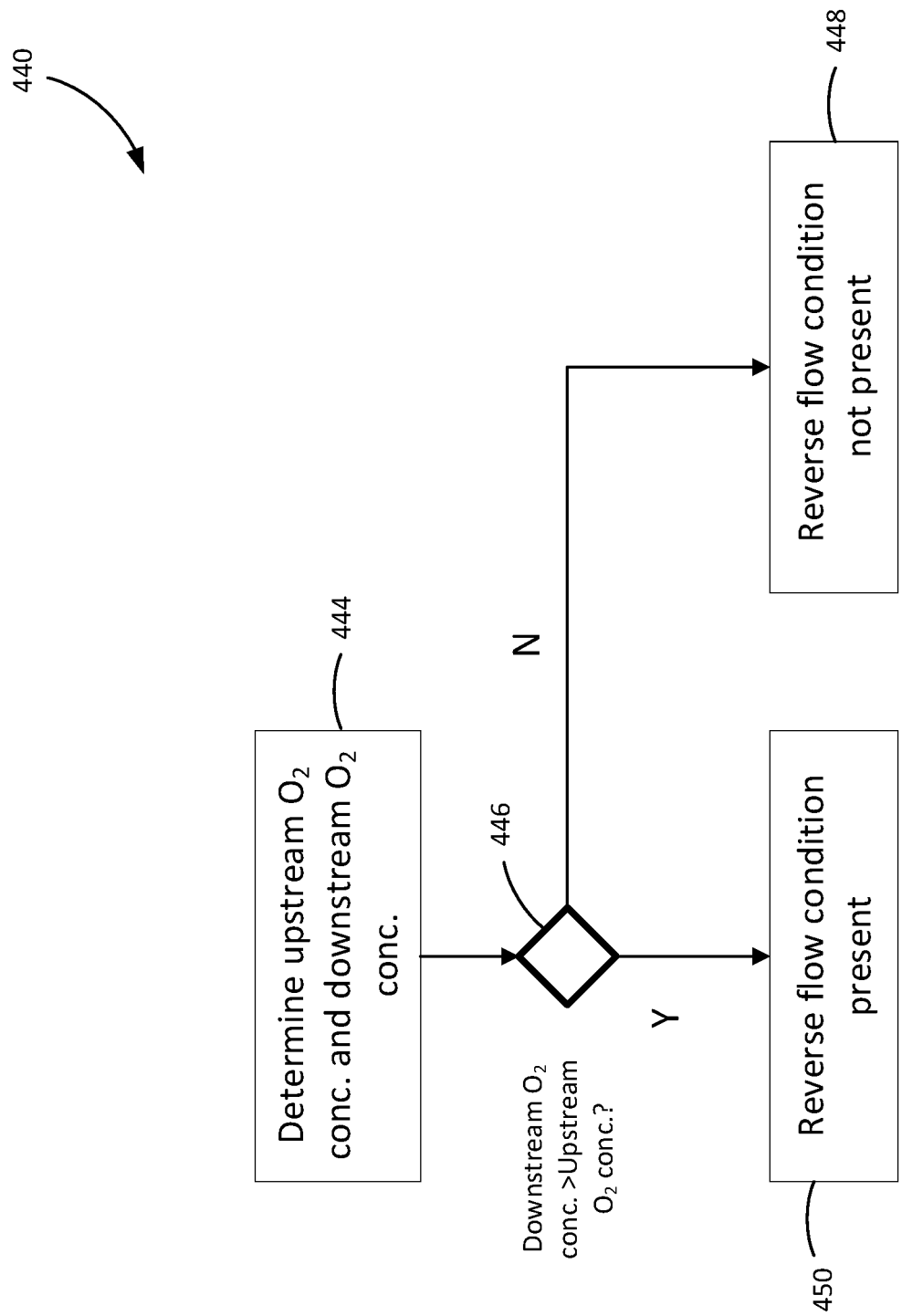

The configuration shown in FIG. 7 can be used with the method 440 shown and described in FIG. 4C. In a method 440 shown in FIG. 4C, the controller can begin a reverse flow detection algorithm. The upstream $O_2$ concentration and the downstream $O_2$ concentration can be determined at step 444. Oxygen concentration can be determined using a gas composition analyzer or sensors that can determine oxygen concentration in a gases flow. An example set up of for the method 400 is shown in FIG. 4 and the sensor 403, 405 can be $O_2$ sensor. The upstream $O_2$ concentration can be $O_2$ concentration in the inspiratory conduit and the downstream $O_2$ concentration can be $O_2$ concentration in the expiratory conduit. There can be one or more $O_2$ sensors in this configuration.

The controller can determine whether the upstream $O_2$ concentration is greater than the downstream $O_2$ concentration at step 446. If the upstream $O_2$ concentration is greater than the downstream $O_2$ level, the controller can determine that there is no incorrect flow at step 448. If the upstream $O_2$ concentration is less than the downstream $O_2$ concentration, the controller can determine that there is incorrect flow at step 450.

Processes Based on Addition or Removal of Thermal Energy

Incorrect flow can be detected by increasing or lowering the temperature of the heater plate or humidification chamber and comparing an inlet temperature and an outlet temperature of the humidifier. To inject thermal energy, the controller can set the humidifier heating element to a first duty cycle. The temperature at the outlet of the humidifier is expected to be higher than the temperature at the inlet of the humidifier during normal flow conditions, because the gases can be heated by the humidifier heating element at the first duty cycle when the gases flow from the humidifier inlet to the humidifier outlet. The first duty cycle is large enough to heat the humidifier heat source to cause a more significant change at one of the humidifier inlet and outlet. If there is incorrect connection resulting in incorrect flow conditions (that is, different from normal flow conditions), the gases may be heated from the outlet to the inlet of the humidifier instead.

To remove thermal energy, the first duty cycle to the humidifier heating element can also be set to or near to zero. In this case, the expected temperature change seen at the humidifier inlet and outlet can be reversed. However, a predetermined amount of time may elapse after setting the duty cycle of the humidifier to or near zero to observe the reversal of the expected temperature change at the humidifier inlet and the outlet. Alternatively, the duty cycle to the humidifier heat source can be set to or near zero after a predetermined period of time. After the predetermined period of time has elapsed, the controller (for example, controller of the humidifier 20 and/or the gases source) can implement the methods described below. Evaporation from the surface of the water in the humidifier cools the gases from the outlet to the inlet in an incorrect flow condition. This first duty cycle can minimize or prevent humidity from being delivered to the ventilator in an incorrect flow condition, which could cause damage to the ventilator or affect its performance.

Optionally, for detecting incorrect flow conditions, a patient end temperature ($T_{PE}$) set point can be set to 34° C. or at least lower than 37° C. Patients can exhale gases having temperature around 37° C. or at least higher than $T_{PE}$. The duty cycle of a heater wire can be reduced to prevent over-heating of the gases (for the normal direction of flow). In incorrect flow conditions, gases can travel from the patient to the chamber outlet and decrease in temperature. The temperature of the gases can drop below a chamber outlet set point. When the temperature drops below the chamber outlet set point, the heater plate power can be increased by the humidifier controller to try to raise the gases temperature back to the chamber outlet set point (under the assumption that the gases are traveling in a normal flow direction). When the heater plate power increases (or turns on), gases travelling in the reverse flow direction from the outlet to the inlet can be heated and humidified. In some implementations, if a chamber outlet temperature drops below a chamber outlet temperature set point and humidifier inlet temperature is greater than a set point or humidifier outlet temperature, such condition can be indicative of an incorrect flow condition.

Optionally, if the above condition is detected for a certain period of time, the controller can set the heater plate duty cycle to zero. This can result in a decrease of the temperature of the gases as they travel from the outlet to the inlet. Cooling can be further achieved as a result of evaporation from the water's surface. In this regard, a decrease in the inlet temperature can be indicative of an incorrect flow condition.

Temperature sensor(s) at various locations described herein can be in electronic communication with a controller. The controller can be a controller of the gases source or a controller of the humidifier. The controller can be the same controller for controlling the heater plate power. The controller can receive measurements from the temperature sensor(s) and process the received measurements. The controller can determine a reverse flow condition and/or indication of incorrect connections as described herein. The electrical communication can be wired or wireless.

Figure 5A:
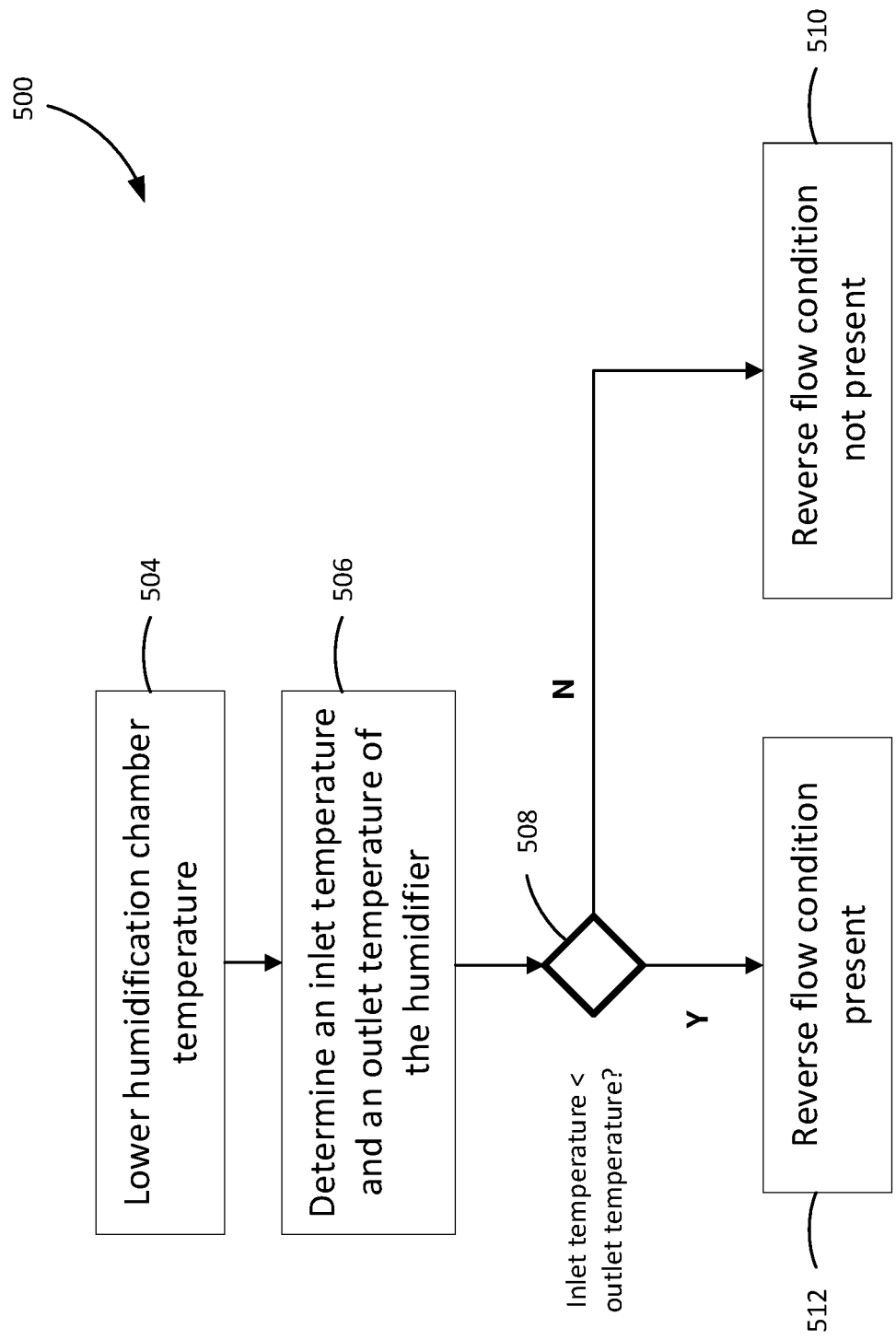
FIGS. 5A-5B illustrate example methods of detecting incorrect flows by lowering temperature in a humidification system.

A method 500, shown in FIG. 5A, is an example method executed by a controller of the system (for example, the controller of the humidifier). The method 500, shown in FIG. 5A, uses a comparison between an inlet temperature and an outlet temperature of the breathing gases at the inlet and the outlet of the humidification chamber, respectively, to determine whether there is incorrect flow in the humidification system when the humidification chamber temperature is lowered. At step 504, the temperature of the humidification chamber is lowered using various internal or external methods (for example, active cooling controlled by the controller, evaporation of water inside the humidification chamber, turning off the heater plate, or any combinations thereof). At step 506, the controller of the humidification system can determine the inlet temperature of the humidification chamber using an inlet sensor and the outlet temperature of the humidification chamber using an outlet sensor. The temperature sensor disclosed herein can include a thermistor, an optical based temperature sensor (for example, an infrared sensor, or otherwise). At step 508, the controller can determine whether the inlet temperature is lower than the outlet temperature. If the inlet temperature is not lower than the outlet temperature, the controller can determine that incorrect flow is not present at step 510. If the inlet temperature is lower than the outlet temperature, the controller can determine that incorrect flow is present at step 512. This method can determine reverse flow provided that the energy input into the system (such as via the heater plate or walls of the humidification chamber) is less than the energy used by evaporation. Some of the energy for evaporation can be from the gases' thermal energy, thereby cooling the gases down. However, if setting the heater plate duty cycle to zero under a normal flow condition with the gases traveling from the inlet to the outlet, the cooling effect can cause the outlet temperature to be less than the inlet temperature.

Figure 5B:
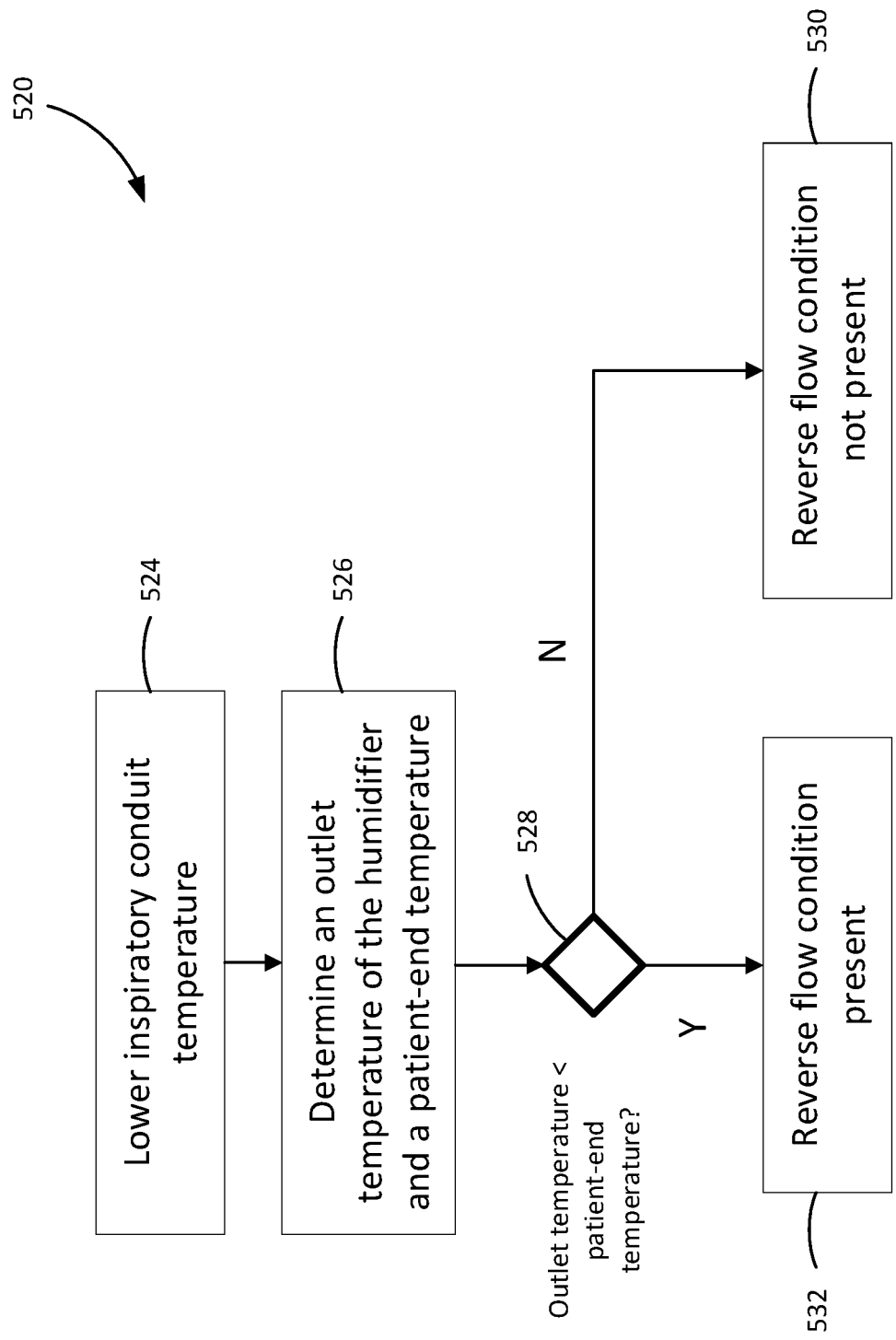

A method, shown in FIG. 5B, uses a comparison between an outlet temperature of the humidification chamber and an inspiratory conduit patient-end temperature to determine whether there is incorrect flow in the humidification system when the inspiratory conduit temperature is lowered. At step 524, the temperature of the inspiratory conduit is lowered using various internal or external methods (for example, active cooling, evaporation of water inside the inspiratory conduit, turning off the heater wire inside the inspiratory conduit, or any combinations thereof). At step 526, the controller of the humidification system can determine the outlet temperature of the humidification chamber using an outlet temperature sensor and the patient-end temperature using a patient-end temperature sensor. At step 528, the controller can determine whether the outlet temperature is lower than the patient-end temperature. If the outlet temperature is not lower than the patient-end temperature, the controller can determine that incorrect flow is not present at step 530. If the outlet temperature is lower than the patient-end temperature, the controller can determine that incorrect flow is present at step 532. That is, gases expired by the patient at 37° C. are cooling along the length of the inspiratory conduit 40.

Processes Based on Removal of Water (that is, Moisture)

For this section, water can include moisture. A change in gas humidity can be used to detect incorrect connection in the humidification system. The humidification system disclosed herein can incorporate tubes, particularly expiratory tubes made of a breathable material (for example, porous enough for water vapor to escape but not for liquid to escape) that allow diffusion of water through their walls. Therefore, as humidified gas travels through the tubes, humidity level of the gas can decrease as the gas travels downstream. Humidity sensors can be placed on both ends of the tubes. The downstream (of the normal flow) sensor is expected to measure a lower humidity than the upstream (of the normal flow) sensor. For example, humidity can be measured at an inlet and an outlet of the expiratory conduit, which can be made at least partially of the breathable material. In normal flow conditions, humidity level at the inlet (patient side) is expected to be higher than humidity level at the outlet (gases source side) of the expiratory conduit.

Figure 6:
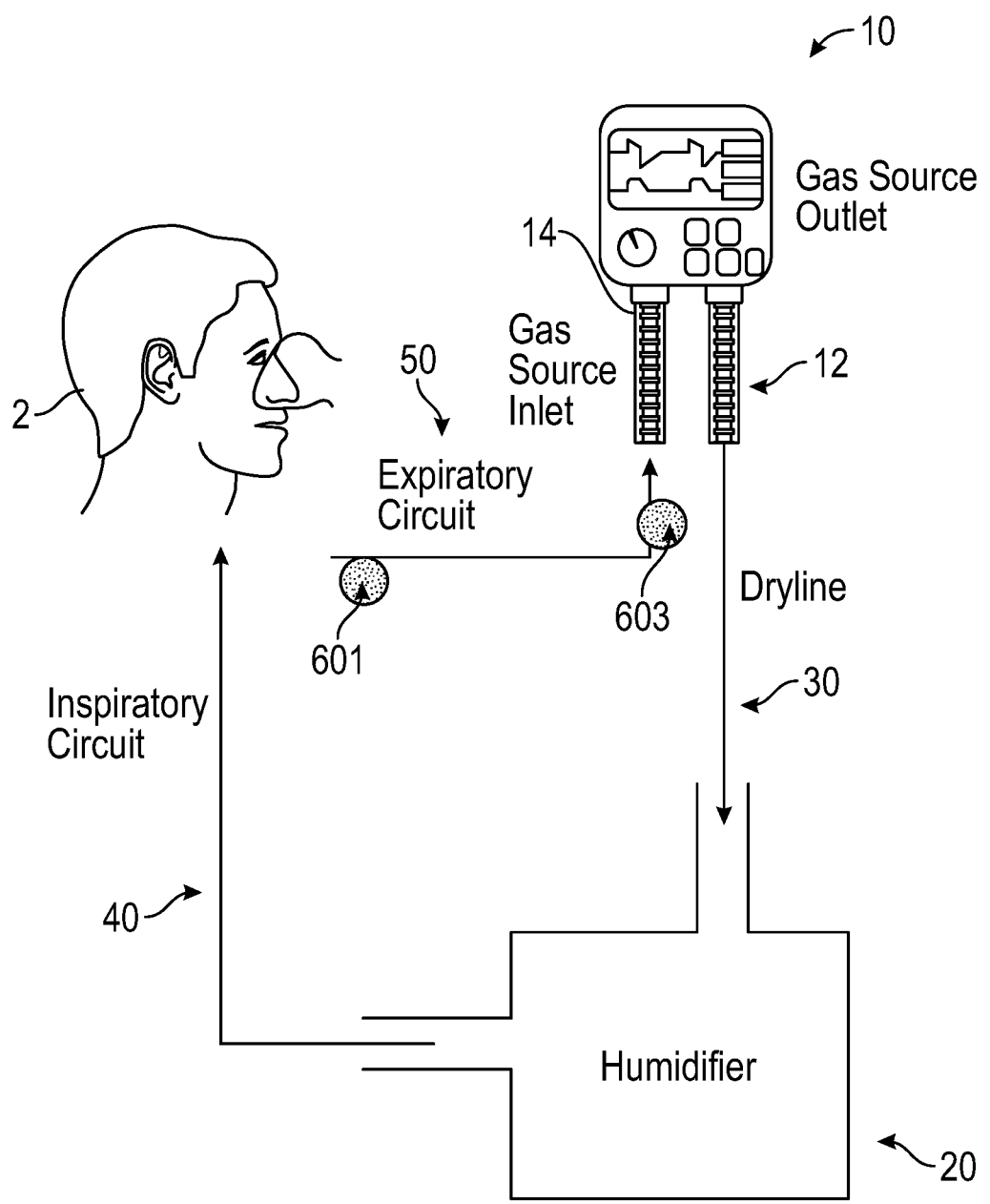
FIG. 6 illustrates an example setup for detecting incorrect flow condition using humidity sensors coupled to an expiratory conduit.

FIG. 6 illustrates an example configuration of the expiratory conduit 50 having a humidity sensor 601 installed at one end and a humidity sensor 603 installed at another end. The humidity sensors 601, 603 can be installed at a patient end and at a gas supply end of the expiratory conduit 50, respectively. The humidity sensors 601, 603 can be coupled to an outer surface or an inner surface of the expiratory conduit 50. The humidity sensors 601, 603 can be integrated with the expiratory conduit 50. The humidity sensors 601, 603 can be coupled to other conduits (for example, the dryline 30 and the inspiratory conduit 40) of the humidification system 1.

A water vapor permeable tube can be used as the expiratory conduit. The water vapor permeable tube can be impermeable to liquid water. For example, the expiratory limb may be water vapour permeable and liquid water impermeable, such as the EVAQUA™ expiratory limb from Fisher & Paykel Healthcare Limited. Humidity sensors that measure humidity can be placed on both ends of the expiratory limb. Optionally, the sensors can measure absolute humidity. During normal flow conditions, the gases (which include the patient's exhaled gases) can travel from the patient towards the inlet of the gases source. A heater wire can be incorporated in the expiratory limb to heat the gases above dew point to reduce rainout. When the expiratory limb is water (that is, moisture) vapor permeable and liquid water impermeable, water (that is, moisture) vapor may pass from the inside to outside of the expiratory limb. This in turn can reduce the humidity or absolute humidity of the gases as they travel from the patient to the gases source. The rate of diffusion of water vapor through the tube wall is dependent on the difference in partial pressure of water vapor between the breathing gases inside the tube, and ambient gases outside the tube, which in turn is dependent on the absolute humidity of the breathing gases and ambient gases. Therefore, during normal flow conditions, the downstream humidity sensor (closer to the gases source) can measure a lower absolute humidity than the upstream humidity sensor (closer to the patient) measuring the relatively warm and humid gases expired by the patient. On the other hand, during incorrect flow conditions, the downstream and upstream humidity sensors may measure a substantially similar humidity because of the relatively low humidity content from the gases source. In this regard, the difference between the humidity measured by the two humidity sensors can be compared with a threshold value to determine whether an incorrect (or a normal) flow condition is present.

The humidity sensor(s) can be in electronic communication with a controller. The controller can be a controller of the gases source or a controller of the humidifier. The controller can be the same controller for controlling the heater wire in the expiratory limb. The controller can receive measurements from the humidity sensor(s) and process the received measurements. The controller can determine a reverse flow condition and/or indication of incorrect connections as described herein. The electrical communication can be wired or wireless.

Figure 6A:
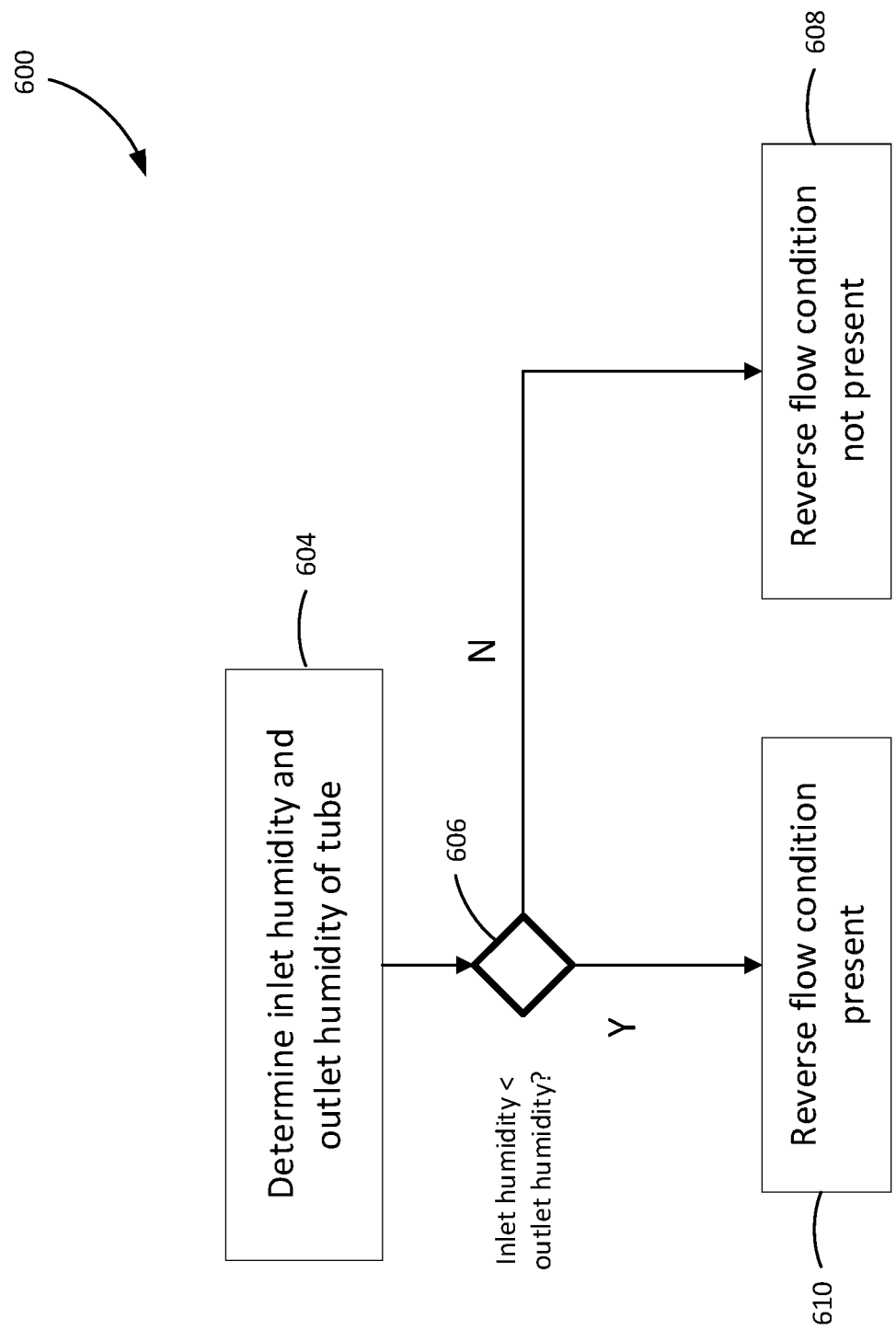
FIG. 6A illustrates an example method of detecting incorrect flows by comparing humidity at different locations of a humidification system.

As shown in the method 600 of FIG. 6A, the controller can begin a reverse flow detection algorithm. An inlet humidity level and an outlet humidity level of a conduit (for example, the dryline conduit 30, the inspiratory conduit 40, or the expiratory conduit 50) can be determined at step 604. The inlet humidity level can be compared to the outlet humidity level at step 606. If the inlet humidity level is greater than the outlet humidity level, the controller can determine that incorrect flow is not present at step 608. If the inlet humidity level is not greater than the outlet humidity level, the controller can determine that incorrect flow is present at step 610.

Processes Utilizing Time of Flight Sensors

Time of flight sensors can be used to detect the presence of a reverse flow condition. An example time of flight sensor includes ultrasonic sensors. Other types of suitable time of flight sensors can also be used. A difference in time from when an ultrasonic signal is transmitted from the first transducer until it is received by the second transducer can be measured.

In one example, if the time difference measured for transmission in the downstream direction (that is, from the transmitter upstream of the receiver) is below a threshold this is indicative of a normal flow condition, and if the time is greater than a threshold time this is indicative of a reverse flow condition. This is because in a normal flow condition the flow carries the acoustic waves, whereas in a reverse flow condition the flow moves against the direction of the acoustic waves, and creates a resistance to the acoustic wave transmission. If there is no flow, the travel time will be the same in both directions. When the flow is present sound moves faster if travelling in the same direction as the flow as compared moving against flow of gases.

A controller, which may be the controller in the humidifier or in the gases source, can be in electrical communication with the time of flight sensors, such as the ultrasonic transducers. The controller is configured to instruct the ultrasonic transducer to emit acoustic signal(s) and receive the signals from the ultrasonic transducers, that is, acoustic transducers. The controller can process the received signals and determine the direction of flow based on the time of flight measurement, that is, the transit time between the sound travelling between the transducers. The electrical communication can be wired or wireless.

Figure 7A:
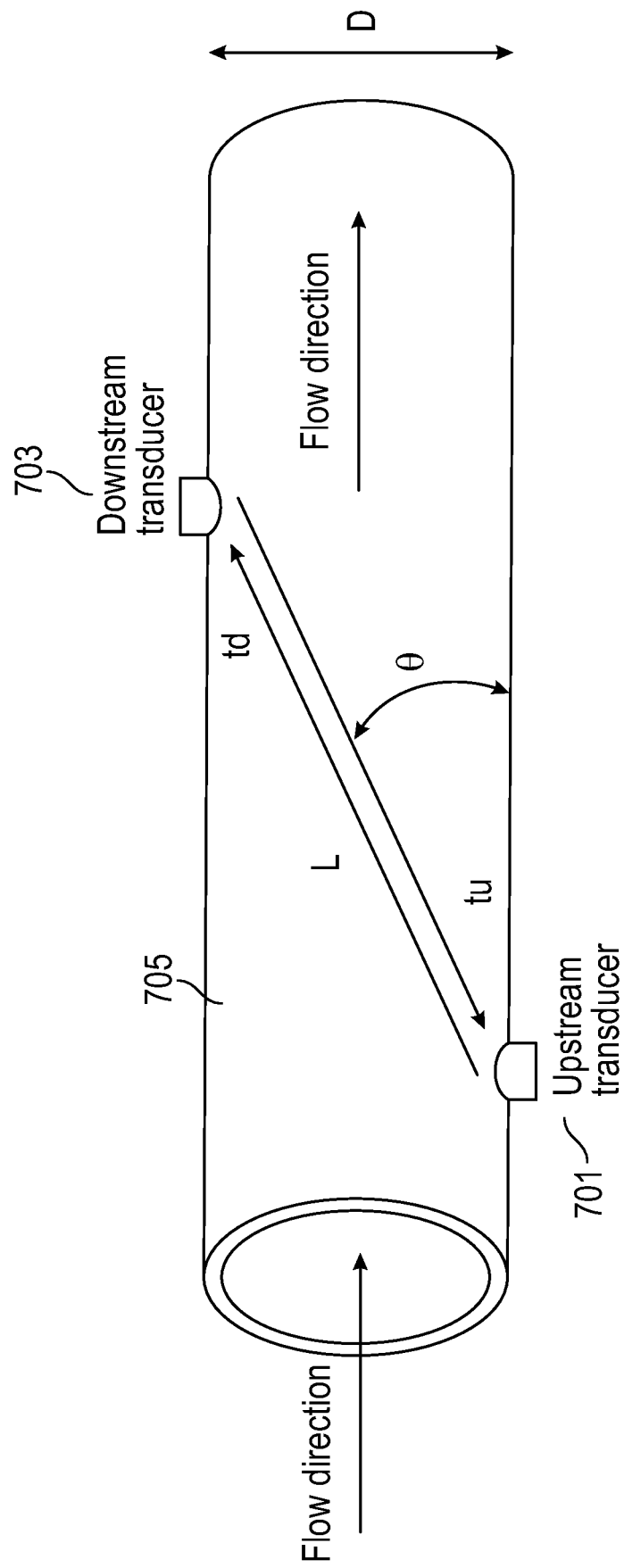
FIG. 7A illustrates an example setup for detecting incorrect flow condition using two ultrasonic sensors.

Referring to FIG. 7A, the time for an ultrasonic signal to travel between the transducer 701 to 703 (T1) will be faster than the time for the signal to travel from 703 to 701 (T2), in a normal flow condition. The time of flight can be determined based on the distance (which is calculated using D, the angle θ, and a trigonometric function) divided by speed of sound. In a reverse flow condition, T2 would be higher than T1. Alternatively, a reverse flow condition may be determined by emitting one signal from 701 to 703 and measuring a transit time of the signal detected at 703. If the transit time is less than a threshold, this is indicative of a normal flow. If the transit time is greater than the threshold, this is indicative of a reverse flow. The angle between the two transducers can be predefined. For example the angle may be between 30 and 70 degree with respect to an axis defined by the length of the conduit or tube. The ultrasonic sensors or transducers 701, 703 may be located within the inspiratory tube in the illustrated embodiment of FIG. 7A. The transducers 701 and 703 may be ultrasonic transceivers capable of outputting ultrasonic signals and detecting ultrasonic signals. Alternatively, one of the sensors or transducers 701, 703 may be a transmitter of ultrasonic waves and one sensor may be a receiver (for example, a microphone).

Processes Based on Humidification Chamber Geometry

Figure 8A:
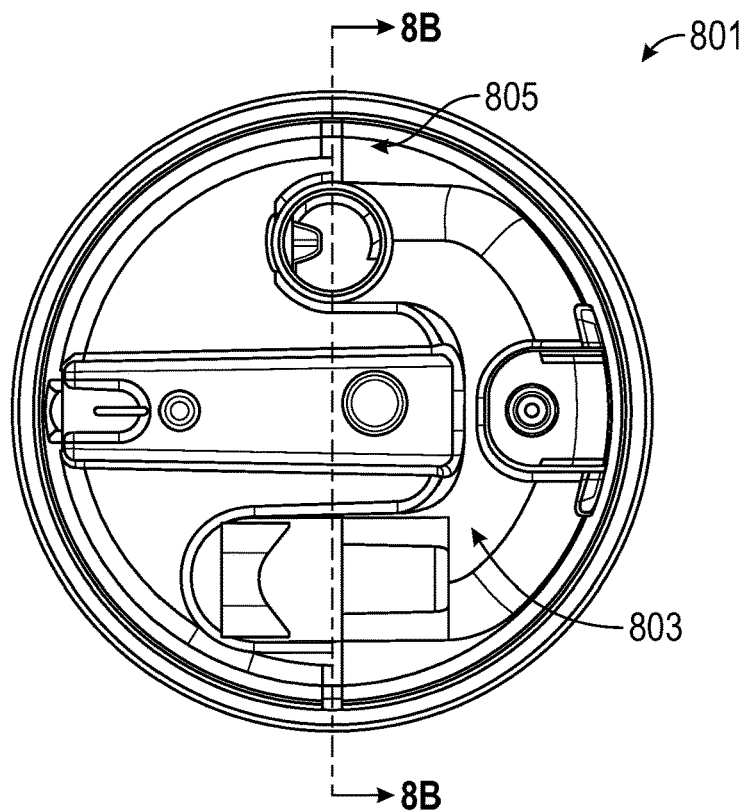
FIG. 8A illustrates a top view of an example humidification chamber.
Figure 8B:
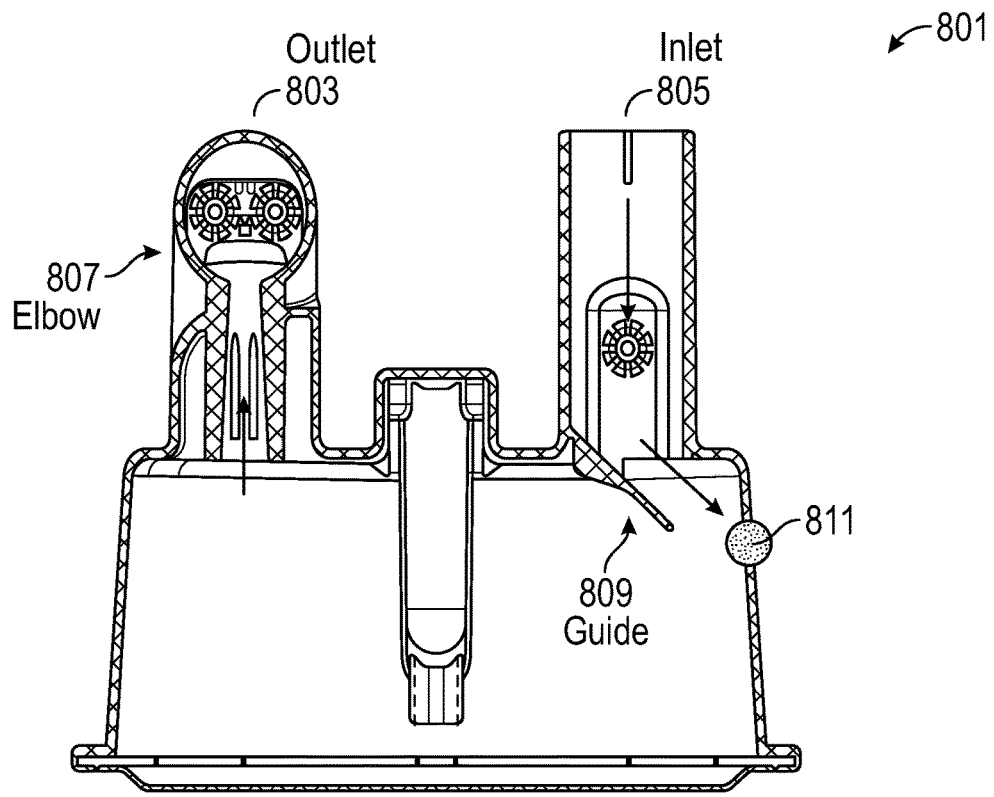
FIG. 8B illustrates an example cross-sectional view of the humidification chamber of FIG. 8A.

Humidification chamber geometry can be used to determine whether there is incorrect flow for the humidification system. An example of the Humidification chamber is shown in FIGS. 8A-8B. The humidification chamber 801 is asymmetrical. The humidification chamber 801 can include an inlet 805 coupled to a flow guide 809 and an outlet 803 that includes an elbow 807. The elbow 807 can be at an angle of about 90°.

The flow guide 809 can act as a baffle or direct flow for the purposes of determining flow direction. The flow guide may direct the gases flow to the inner surface of the humidification chamber. A flow sensor within the humidification chamber can measure a higher flow rate during normal flow conditions than during incorrect flow conditions because the geometry of the flow path can act as a nozzle during incorrect flow conditions. The flow sensor can be positioned at the region of the humidification chamber 801 where the flow rate is the greatest. The flow sensor can be located at a region 811 shown in FIG. 8B. The region 811 can be located adjacent to the flow guide 809. The flow sensor may be integrally formed within the humidification chamber or it may protrude into the humidification chamber. The flow measured by the flow sensor value can be compared to a threshold. If the measured flow is above the threshold, it can be indicative of normal flow conditions. However, if the measured flow is less than the threshold, it can be indicative of incorrect flow conditions. Alternatively, or additionally, a temperature sensor near the inlet 805 of the humidification chamber 801, for example, at location 811, can measure a lower temperature during normal flow conditions than during incorrect flow conditions as the gases flowing through the inlet 805 are ambient or relatively colder than the heated and humidified gases.

A pressure sensor can also be used instead of the flow sensor. The pressure sensor may contain a diaphragm configured to deflect when there is a flow of gas. The diaphragm may deflect more during normal flow conditions because the inlet of the humidification chamber can direct more flow towards the diaphragm, whereas the diaphragm may be positioned in such way that the flow of gases has minimal effect on the diaphragm during incorrect flow conditions. When gas is flowing from the inlet to the outlet, the flow guide can direct flow of the gas.

Figure 9A:
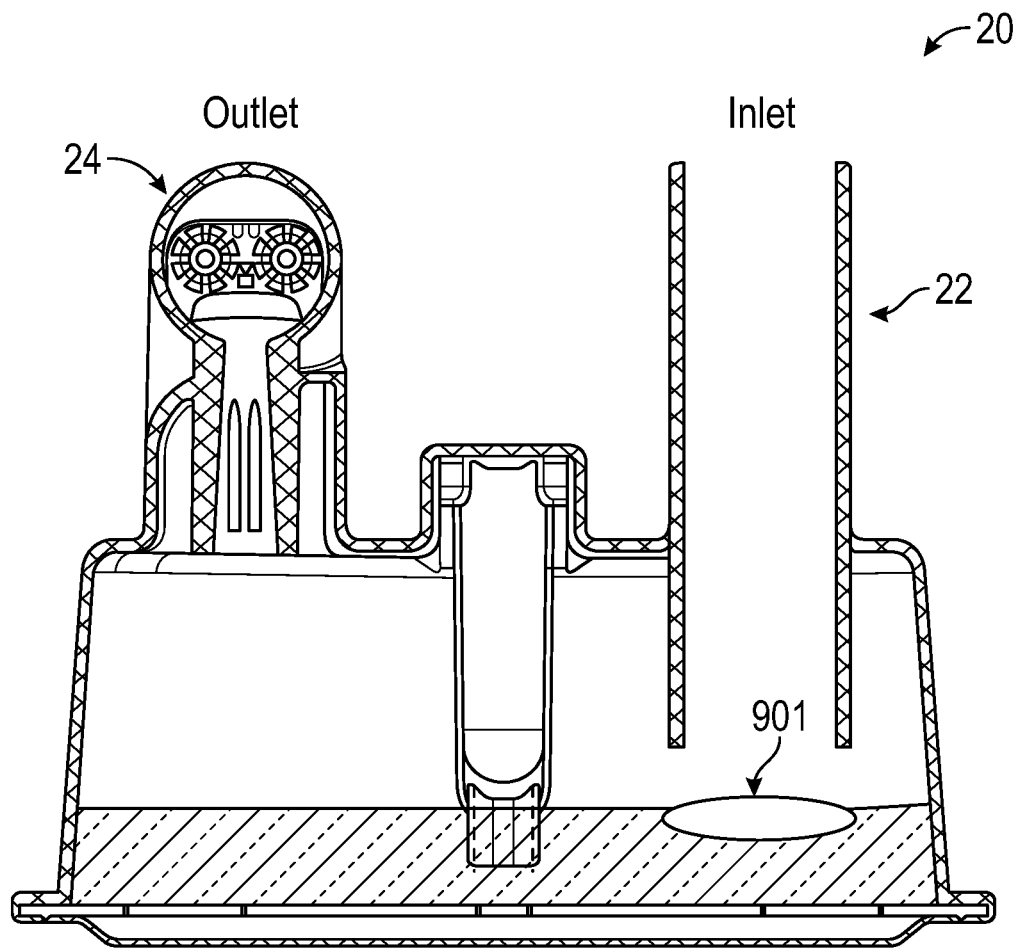
FIG. 9A illustrates an example cross-sectional view of the humidification chamber of FIG. 8A, showing regional cooling of water surface.

The guide 809 may alternatively be used to direct the gases flow towards a focused region of the water surface in the humidifier. As shown in FIG. 9A, the gas can be directed towards a focused region 901 of the water surface directly underneath the inlet. The gas may be directed to the focused region via a guide 809 or due to an inlet that is shaped and configured to guide gases onto the focused region. For example, the inlet as shown in FIG. 9A includes an elongate tube that extends into the chamber to cause flow of gases to be directed onto the focused region 901. During normal flow, the gases flowing through the inlet can be cold (such as being ambient). Therefore, the directed gas can rapidly cool the focused region of the water surface more than the remainder of the water surface. A temperature sensor can measure this cooling effect. During incorrect flow, the gas cannot be directed by the guide to cause a rapid cooling effect on the focused region. Therefore, if the water surface at the focused region does not cool below a particular threshold, an incorrect flow condition can be detected.

Figure 9B:
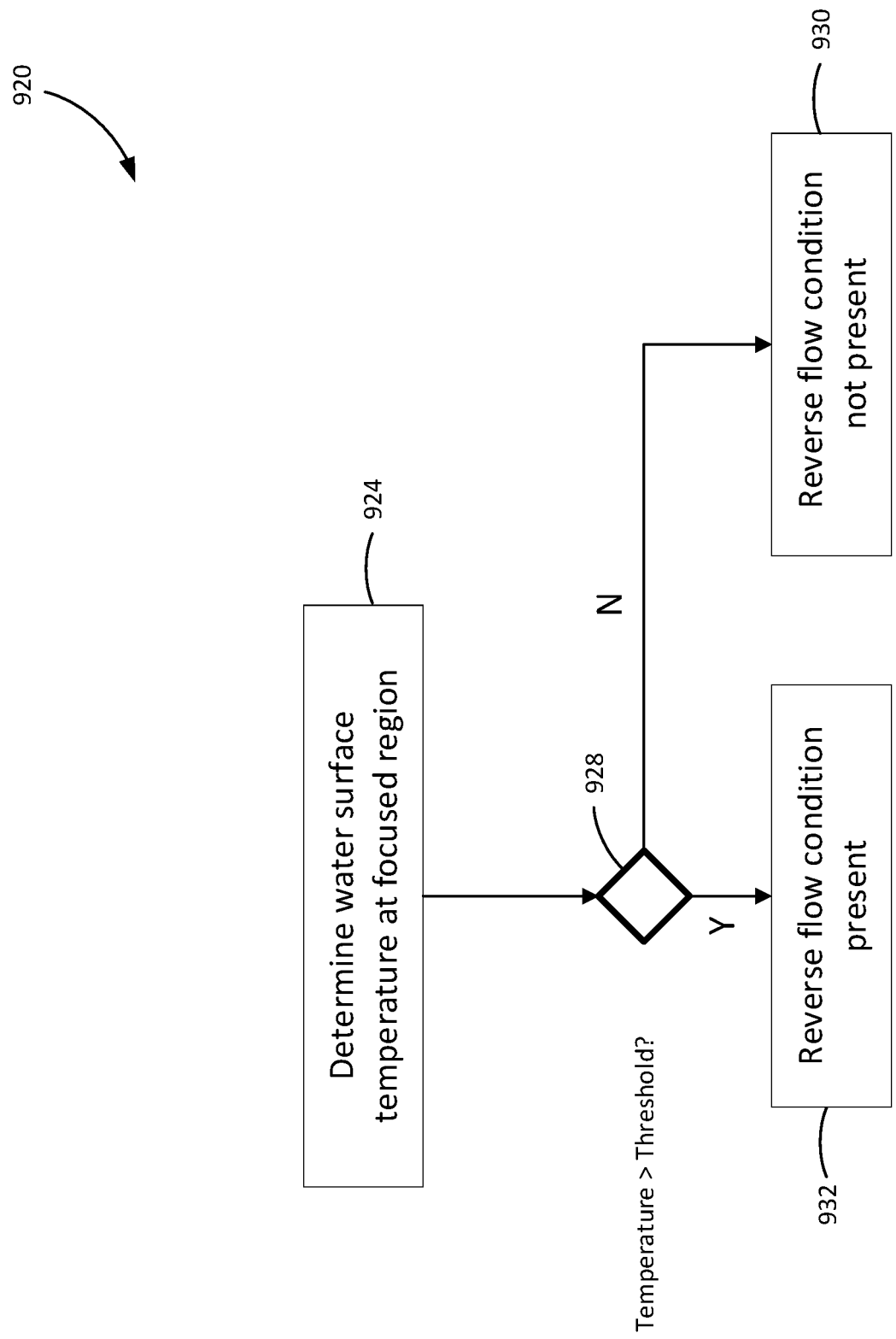
FIG. 9B illustrates an example method of detecting incorrect flow using regional water surface temperature measurements in a humidifier.

In a method 920, shown in FIG. 9B, the controller can begin a reverse flow detection algorithm. The controller can determine a first water surface temperature at a first location at step 924. The first location can be approximately below the inlet of the humidifier. At step 928, the controller can determine whether the measured temperature at the focused region is below a threshold temperature (such as room temperature measured by an ambient temperature sensor). If the temperature at the focused region is higher than the threshold temperature, the controller can determine that incorrect flow is present at step 932. If the temperature at the focused region is below the threshold temperature, the controller can determine that incorrect flow is not present at step 934. Alternatively and/or additionally, a comparison of water temperatures measured at the focused region of the water surface and at another area of the water surface away from the focused region can also determine whether there is incorrect flow in the humidification system. This is because in a reverse flow condition warmed gases are delivered to the chamber, since the gases are warmed by the heater wire of a conduit (for example, an inspiratory conduit or expiratory conduit) as the gases come from the patient. This can be indicative of an incorrect set up (that is, incorrect connections) as shown in FIG. 2A or FIG. 2C.

Figure 9C:
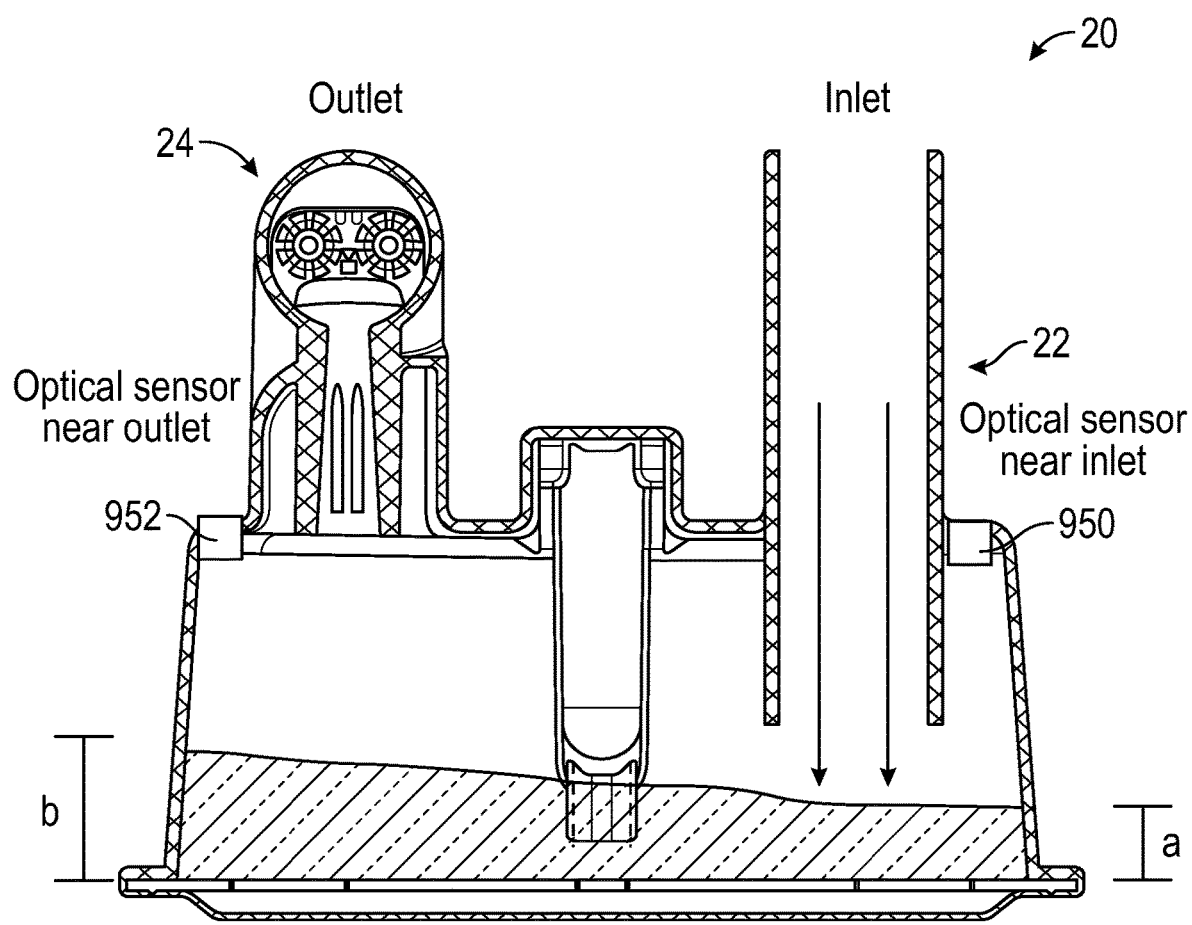
FIG. 9C illustrates an example cross-sectional view of the humidifier of FIG. 8A showing an example directed gases flow changing water surface level.

Alternatively and/or additionally, a comparison of the contour of water level at different locations of the humidifier can also determine whether there is incorrect flow in the humidification system. During normal flow conditions, gases flowing through the inlet 22 can displace the water near the inlet 22 of the humidifier 20 such that water level "a" is smaller than water level "b", as shown in FIG. 9C. This is because the gases flowing into the chamber 20 via the inlet 22 can cause the water to displace due to a force from the inlet gases. This can be particularly the case when higher flows are used e.g. above 20 L/min. The higher the flow the greater the displacement of the water. If "b" is not greater than "a" by a predetermined threshold, an incorrect flow condition can be detected. This difference can be measured, for example, by optical sensors placed at the inlet and outlet of the humidifier. The optical sensors may be placed adjacent to the inlet and the outlet of the humidifier, as shown in FIG. 9C. The water levels near or adjacent to the inlet 22 and the outlet 24 can be measured by sensors 950, 952. The sensors 950, 952 can be optical sensors. The sensors 950, 952 can be in communication with a controller of the system (for example, a controller of the humidifier or a controller of the gases source). The sensors 950, 952 can wirelessly communicate with the controller such that the controller can receive signals from the sensors. The controller can execute a method to detect reverse flow conditions and/or detect the presence of incorrect connections.

Figure 9D:
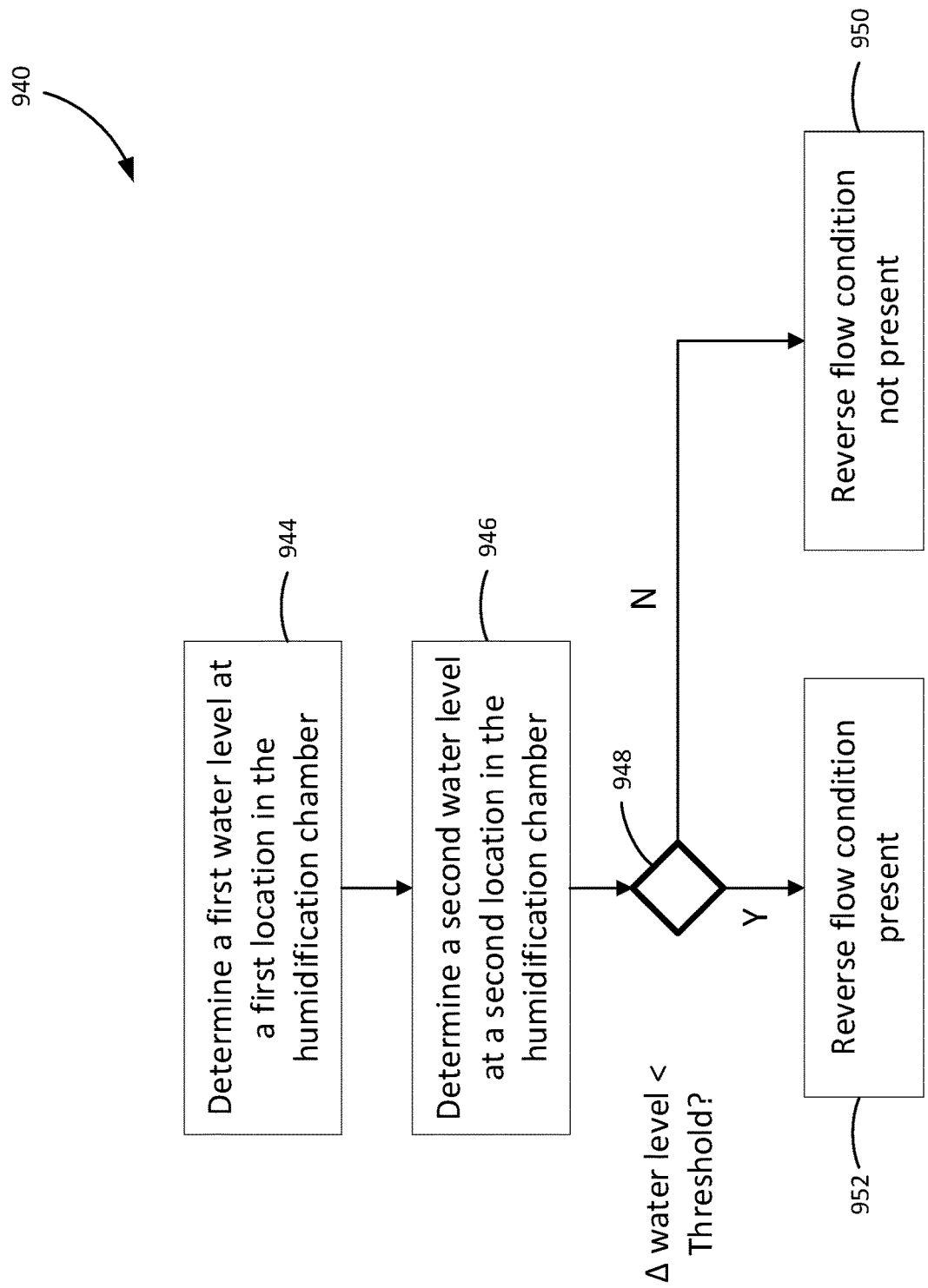
FIG. 9D illustrates an example method of detecting incorrect flow using water surface level measurements.

In a method 940 shown in FIG. 9D, the controller can begin a reverse flow detection algorithm. The controller can determine a first water level at a first location in the humidification chamber 801 at step 944. The controller can determine a second water level at a second location in the humidification chamber 801 at step 946. The first location and the second location are different. The first location can be near the inlet of the humidification chamber 801. The second location can be near the outlet of the humidification chamber 801. At step 948, the controller can compare the first water level and the second water level as described above. For example, the controller can determine whether the second water level is greater than the first water level by a predetermined threshold. Optionally, a preliminary step can be added to establish a baseline water level at either or both of the first and second locations in the absence of a gases flow. The baseline can allow more accurate comparison of the first and second water levels in the event that the chamber is placed on a surface that is not level. If the difference does not exceed the threshold, the controller can determine that incorrect flow is present at step 952. If the difference exceeds the threshold, the controller can determine that incorrect flow is not present at step 950. In some examples, the first water level and the second water level can be an average of measured water levels over a predetermined length of time. The average can be updated at a predetermined frequency. The method can determine a reverse flow condition that is indicative of incorrect connections.

Figure 10:
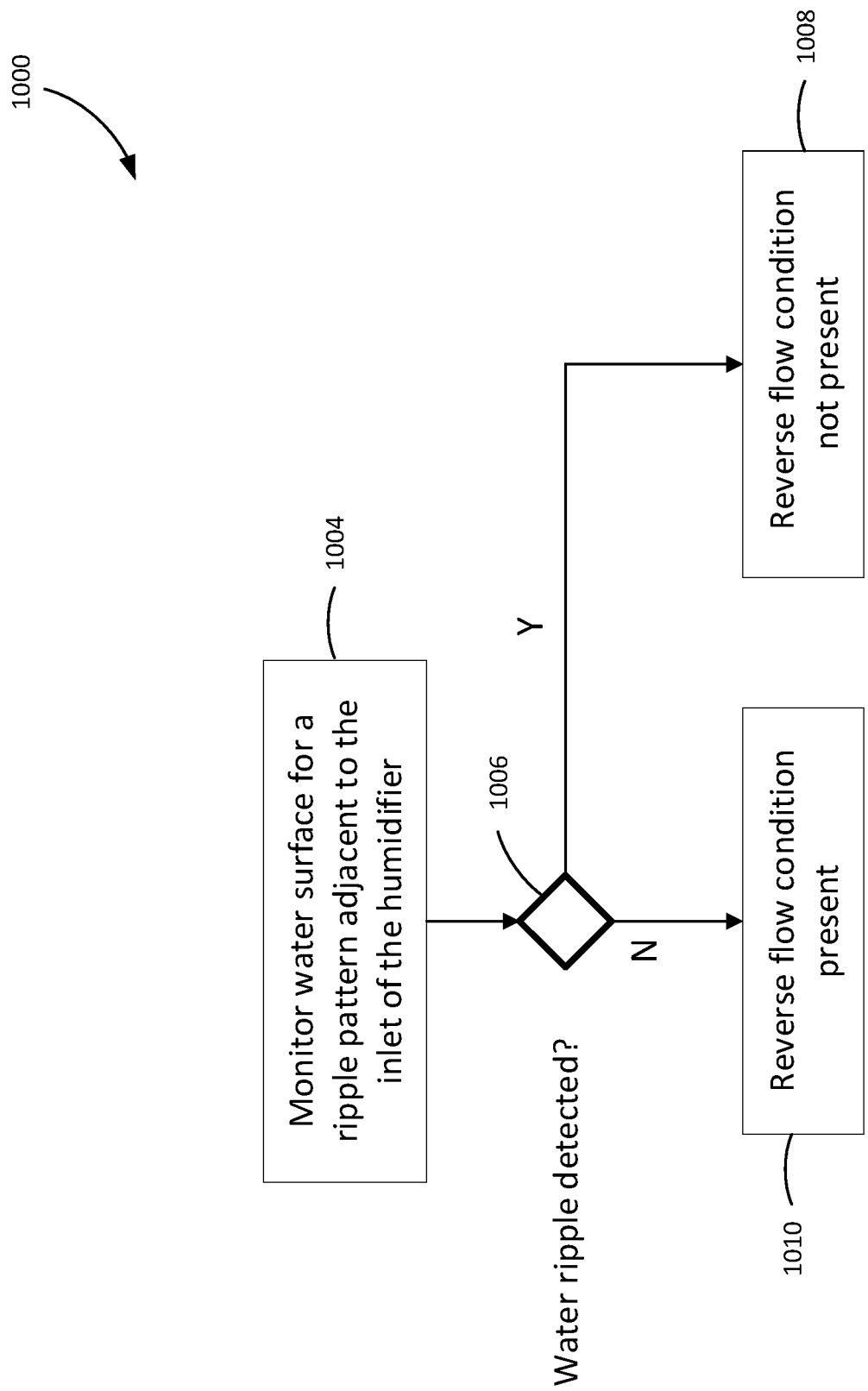
FIG. 10 illustrates an example method of detecting incorrect flow by detecting water ripple patterns.

A detection of ripple pattern on the water surface can also indicate an incorrect flow condition caused by an incorrect connection. The inlet and outlet may be provided at different angles to the water surface (or a guide 809 as shown in FIG. 8B may be used) to provide a difference in the pattern or direction of the ripples for the normal and reverse flows. In a method 1000 shown in FIG. 10, the controller can begin a reverse flow detection algorithm. At step 1004, a sensor monitors a water surface adjacent to the inlet of the humidifier for a ripple pattern. The sensor may be placed below the inlet and/or outlet of the humidifier, or directed at a surface of the water below the inlet and/or outlet of the humidifier. The sensor can be in electronic communication with the controller of the system (for example, a controller of the humidifier or a controller of the gases source). The sensors can wirelessly communicate with the controller such that the controller can receive signals from the sensors. At step 1006, the controller determines whether water ripple is detected. The ripple pattern may be a predetermined pattern that would be detected by a sensor (for example, an optical sensor) that is stored in the controller. The controller may be configured to either detect a ripple by comparing the detected optical sensor signals with a predetermined stored ripple (that is, a predetermined pattern) that can be detected by an optical sensor, or classifying an image of the water surface using image/pattern recognition techniques. During normal flow conditions, the gases flowing through the humidifier inlet can be focused. The focused flow can create a ripple pattern on the surface of the water in the humidifier. However, during incorrect flow conditions, the ripple would not be observed since there is no flow guide coupled to the outlet of the humidifier. In the incorrect flow condition, the water surface can be substantially level. If ripple is detected, the controller can determine that there is no incorrect flow at step 1008. If ripple is not detected, the controller may determine that incorrect flow is present at step 1010. If a ripple is not detected this can be indicative of a reverse flow condition indicative of an incorrect connection (for example, like FIG. 2A or 2C).

The various sensor(s) disclosed above can be in electronic communication with a controller. The controller can be a controller of the gases source or a controller of the humidifier. The controller can receive measurements from the sensor(s) and process the received measurements. The controller can determine a reverse flow condition and/or indication of incorrect connections as described herein. The electrical communication can be wired or wireless.

Processes Based on Differential Pressure Measurements

When gases are circulated within the humidification system, the flow of the gases and the geometries of the conduits and humidifier can affect pressure at different locations of the humidification system. By analyzing the geometric dimensions and determining pressures at different locations, the direction of flow can be determined, which, as noted above, can be indicative of whether there is an incorrect connection in the humidification system.

Figure 11A:
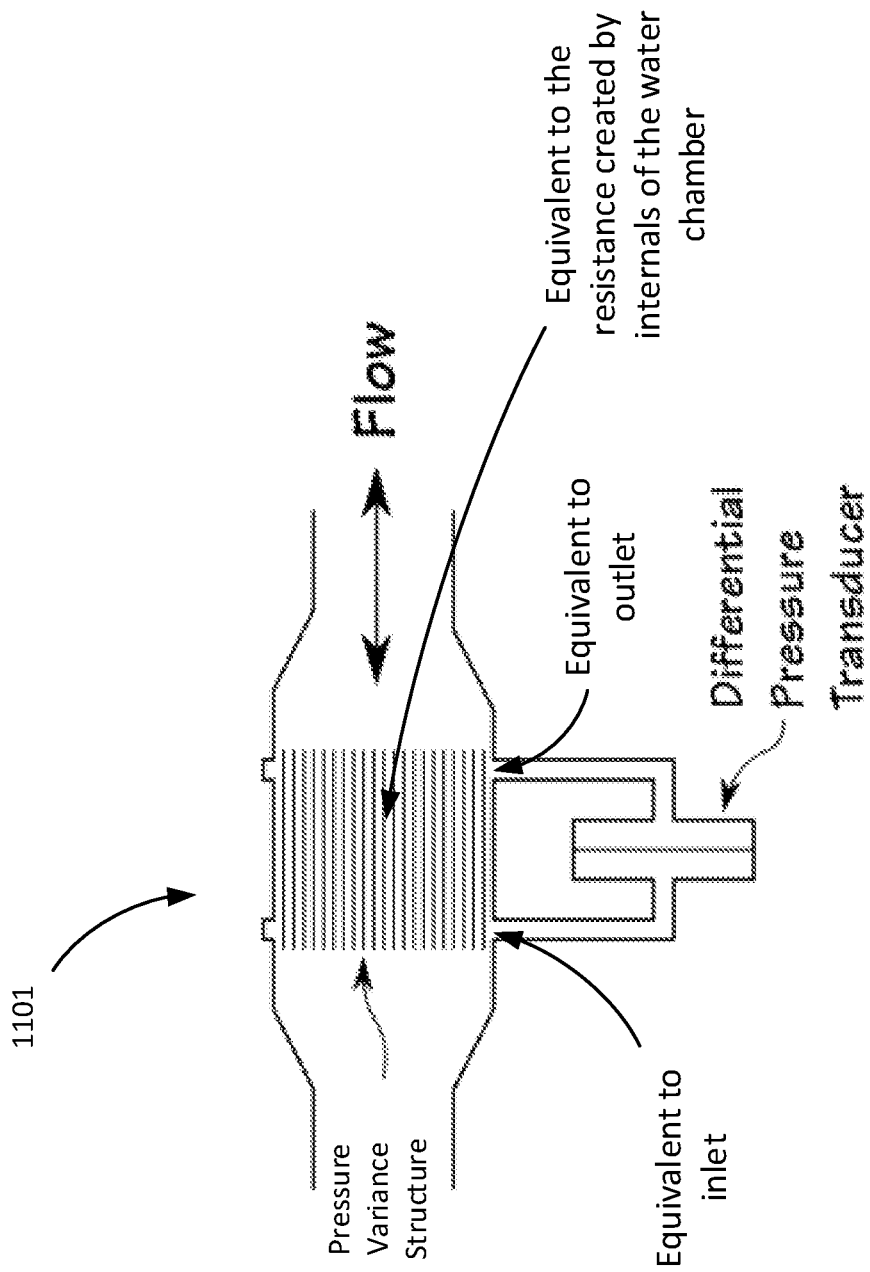
FIG. 11A illustrates an example pneumotach configured to determine flow velocity using differential pressure.

Differential pressure can be used to measure a gases flow rate using Bernoulli's principle, that is, a change in the speed of a fluid can correlate to a change in pressure. The flow rate can be determined by a differential pressure sensor or a pneumotach 1101, shown in FIG. 11A, which generates a pressure drop directly proportional to the flow rate. The pneumotach includes a pressure variance structure, that is, a structure to vary the pressure of gases flowing through the pneumotach from one end to the other end. The pressure variance structure can comprise one or more flow restrictions or other structures that cause a pressure to change that is, drop. Differential pressure measurements can be made at various locations within the humidifier. Reverse flow can be detected using the direction of the pressure differential. The differential pressure sensor or pneumotach 1101 can output a positive flow during normal flow conditions and a negative flow during incorrect flow conditions. As shown in FIG. 11A, the points of pressure measurement and the pressure variance structure can correspond with appropriate regions of the chamber. For example the pressure variance structure can comprise floats within the chamber. The floats within the chamber are one example of a structure that contribute to an overall pressure drop across the chamber. The floats can be positioned within the chamber to control the flow of water in auto filling chambers. The floats can occupy a substantial volume of the chamber and can act as a restriction that causes a change in pressure of the gases as the gases flow through the chamber. Alternatively the pressure variance structure may be the change in shape of the inlet port and outlet port relative to the chamber. There can be a constriction at the outlet port. Other flow restrictions or structures can be used within the pneumotach 1101 or differential pressure sensor to create a pressure drop in the gases path. Pressure can be measured at the ends of the flow restriction is measured by a differential pressure sensor or two pressure sensors, and the controller determining the difference. The differential pressure measurement can correspond to the direction of gases flow. For example the differential pressure measurement is an inlet pressure minus an outlet pressure. A positive differential pressure can indicate higher pressure at the inlet of the chamber and a lower pressure at the outlet of the chamber. This denotes a normal flow. A negative pressure differential can indicate a reverse flow condition. This is because in a reverse flow conditions, gases can enter the chamber at the outlet and reduce in pressure due to the flow restriction of the floats in the chamber.

Figure 11B:
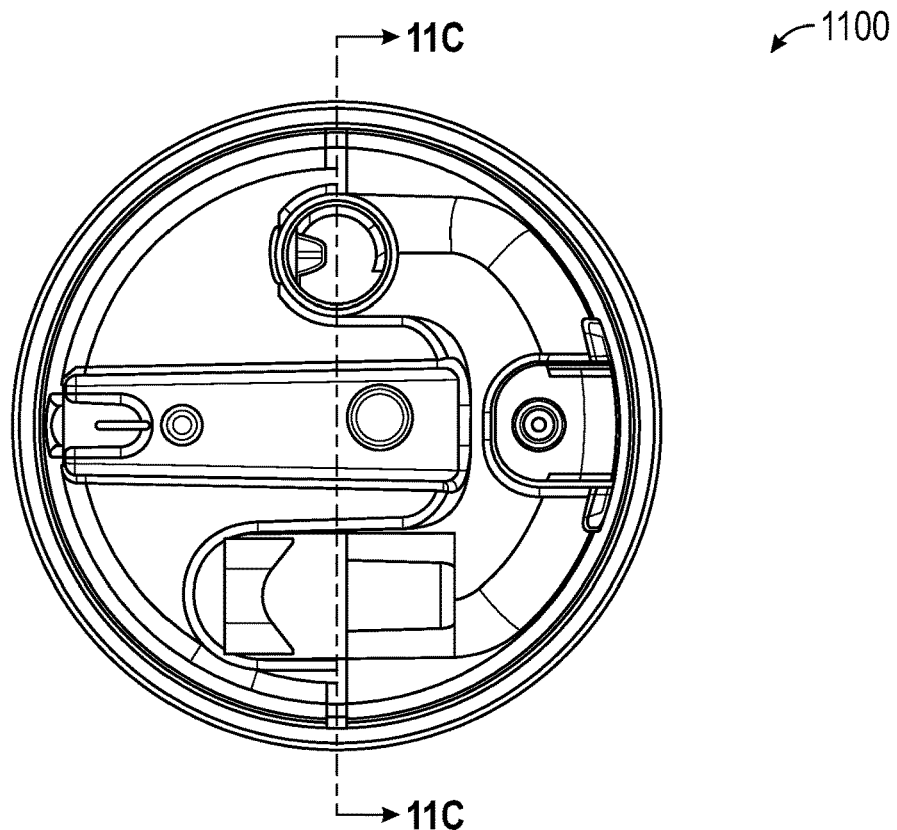
FIG. 11B illustrates a top view of an example humidification chamber.
Figure 11C:
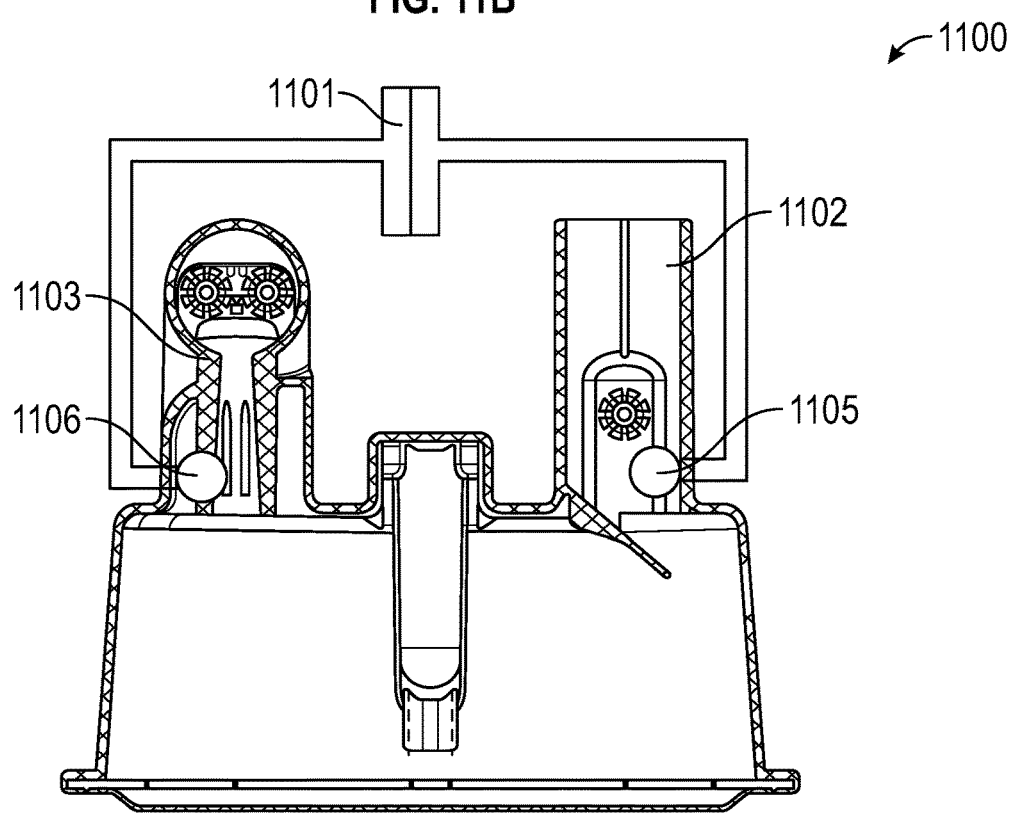
FIG. 11C illustrates an example cross-sectional view of the humidification chamber of FIG. 11B, showing example locations where pressure measurements can be made and a pneumotach being used with the chamber.

FIG. 11B shows a top view with a cross section labelled 11C corresponding to the cross section shown at FIG. 11C. FIG. 11C shows a cross section of the chamber 1100 of FIG. 11B with a pneumotach 1101 positioned on the chamber in an operative position to determine differential pressure across the chamber. The pneumotach can connect across the chamber 1100 (that is, between the inlet port and the outlet port). As shown in FIGS. 11B and 11C, differential pressure measurement can be made across the humidification chamber using the water and floats as flow resistance. The floats act as a flow restriction for the pneumotach 1101. FIG. 11C shows an example sensing arrangement positioned on the chamber. The pressure measurements can be taken near the inlet 1102 and the outlet 1103 of the humidification chamber 1100. In this example, flow direction can be determined by measuring the magnitude of the pressure drop between the inlet 1102 and the outlet 1103. During normal flow conditions, the pressure differential between the inlet and the outlet can be positive. During incorrect flow conditions, the pressure differential between the inlet and the outlet can be negative. The pneumotach 1101 can alternatively be located along the inspiratory conduit, the expiratory conduit, and the dryline conduit.

Figure 11D:
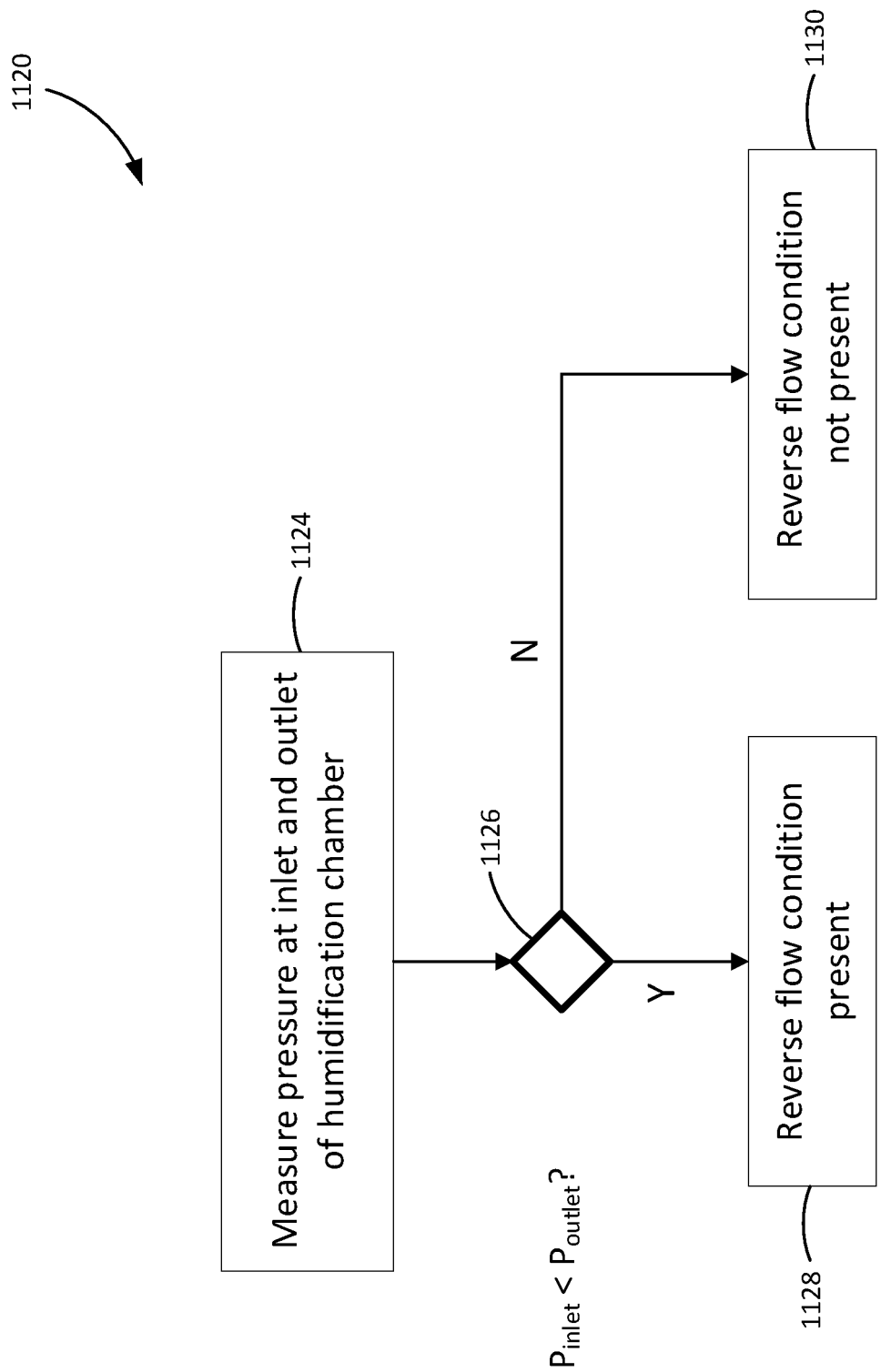
FIG. 11D illustrates an example method of detecting incorrect connections using differential pressure measurements in a humidification system.

In a method 1120 shown in FIG. 11D, the controller can begin a reverse flow detection algorithm. The controller can determine a first pressure reading at a first location near the inlet and a second pressure reading at a second location near the outlet at step 1124. More specifically step 1124 can include measuring a differential pressure between the inlet and outlet pressures. Step 1126 can include comparing the differential pressure. Step 1126 can include checking a sign of the differential pressure that is measured by the differential pressure sensor. At step 1126 if the inlet pressure is less than the outlet (that is, a negative pressure differential is measured), then the controller can proceed to step 1128. Step 1128 can include returning a reverse flow condition being present. Alternatively, at step 1126 if the inlet pressure is greater than the outlet pressure (that is, a positive pressure differential is measured), then the controller can proceed to step 1130. At step 1130 returns a normal flow (that is, no reverse flow detected). If the controller determines an output of reverse flow at step 1106, this can be indicative of incorrect connections in the system. Following the determination of reverse flow at step 1126, the controller may transmit a message or signal to the user interface to display to the user the occurrence of a reverse flow condition. The user interface may present an alarm to the user (for example, a visual alarm or an audible alarm) if a reverse flow condition is determined.

Figure 12A:
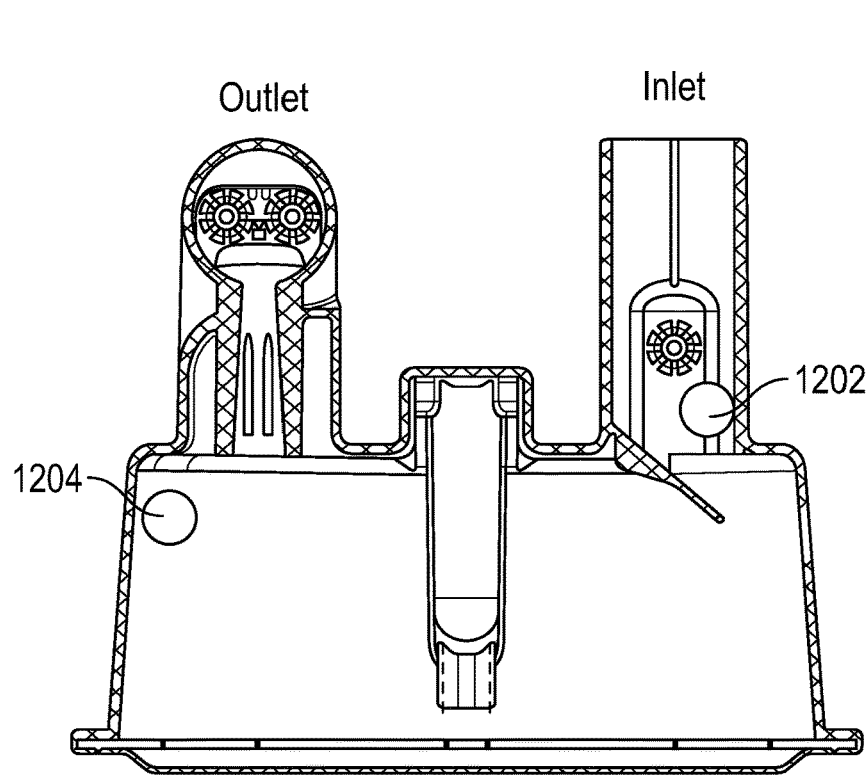
FIGS. 12A and 12B illustrate an example cross-sectional view of the humidifier of FIG. 8B showing example locations where pressure measurements can be made.

FIG. 12A illustrates example first and second locations for pressure sensing devices 1202, 1204. The example locations are illustrated as solid dots. Pressure sensing devices can be placed in the humidifier or humidification chamber immediately before the entrance of the outlet and/or within the inlet of the humidifier or humidification chamber. In this case, the pressure sensing device near the outlet can have a greater cross-sectional area than at the inlet. Inlet pressure sensor 1202 is associated with the inlet (that is, inlet port) of the chamber and outlet pressure sensor 1204 is associated with the outlet of the chamber. In the illustrated in FIG. 12A the inlet pressure sensor 1202 is located in the inlet (that is, inlet port) of the chamber 1200. As shown in FIG. 12A the outlet pressure sensor 1204 is located outside the outlet (that is, outlet port) but adjacent the outlet. At step 1126, the controller can compare the first and second pressure readings (that is, comparing readings from the inlet pressure sensor 1202 and outlet pressure sensor 1204). If the pressure measured at the inlet pressure sensor 1204 is greater than the outlet pressure sensor 1204, then the method steps to step 1128. If the pressure measured at the outlet pressure sensor 1204 is greater than the pressure measured at the inlet pressure 1202 (that is, inlet pressure is less than outlet pressure), the method steps to step 1130. If a reverse flow condition is detected as per step 1130, this is indicative of incorrect connections. The controller may transmit a signal or message to a user interface (for example, a screen of a humidifier or a screen of the gases source) to present a message or alarm to a user.

Figure 12B:
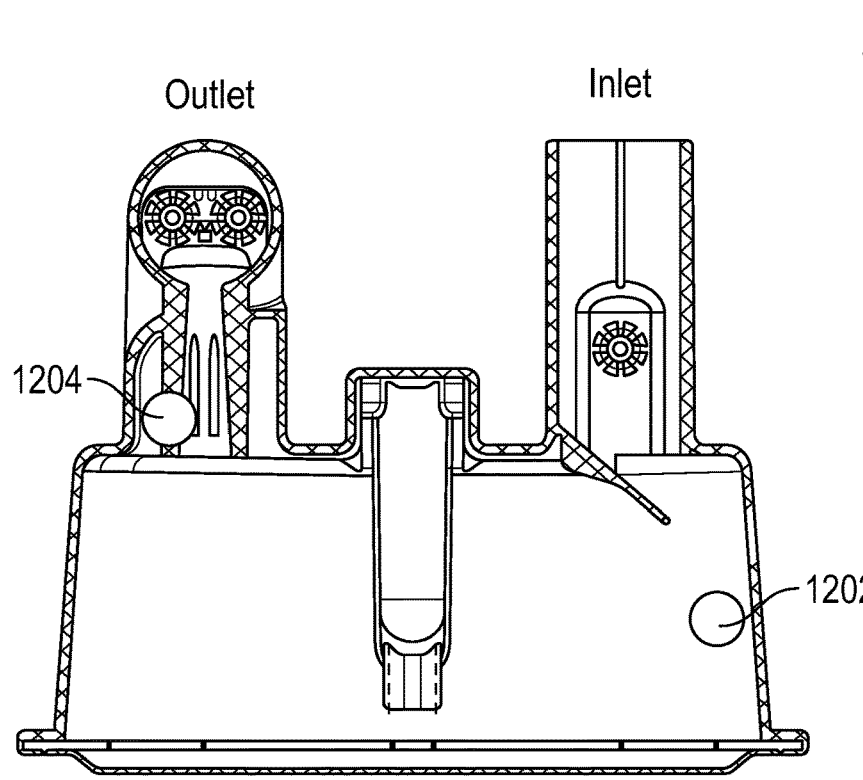

FIG. 12B illustrates a further example of first and second locations for pressure sensing devices. As shown in FIG. 12B the inlet pressure sensor 1202 can be positioned outside the inlet and adjacent the inlet. The outlet pressure sensor 1204 can be positioned in the outlet. The pressure sensor arrangement of FIG. 12B can be used when the controller executes the method of FIG. 11D.

Figure 12C:
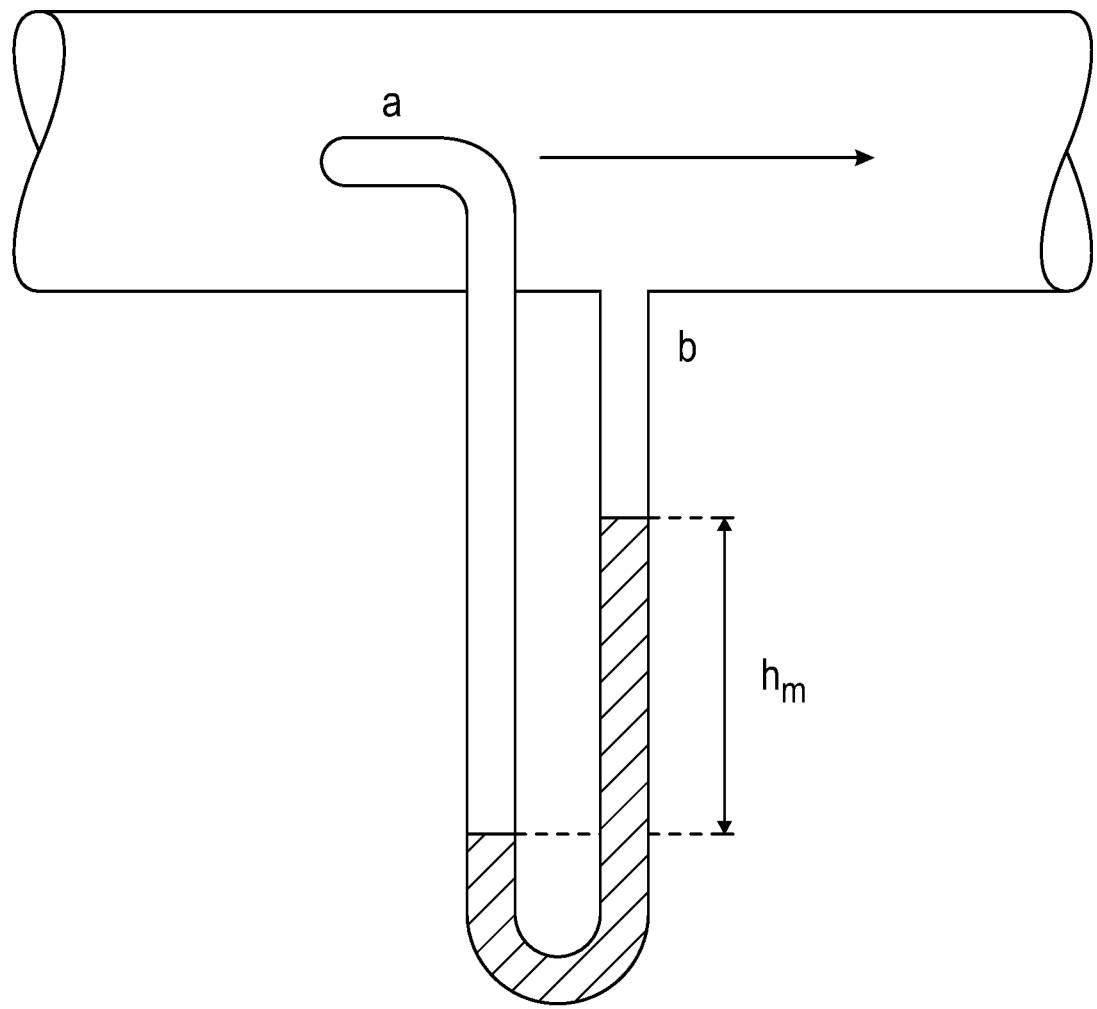
FIG. 12C illustrates an example pitot tube configured to be positioned in a humidification system.

Additionally or alternatively, a pitot tube can be used to detect difference in pressure for example pressure difference across a tube in the gases flow path. An example of a pitot tube positioned in a tube (which can be any conduit in the humidification system) is shown in FIG. 12C. When there is flow from left to right as indicated by the arrow (for example, during normal flow conditions), the pressure at location "a" can be greater than the pressure at location "b", resulting in a pressure difference hm. If flow is from right to left (for example, during reverse flow conditions), the pressure at "a" will be slightly less than pressure at "b", or the pressure difference hm can be less than in normal flow conditions. Therefore, the pressure difference being less than a threshold value may indicate reverse flow. The pitot tube arrangement may be positioned in the inspiratory tube and can be used to determine the presence of a reverse flow condition. The pitot tube shown in FIG. 12C may alternatively be arranged in the outlet of the chamber. The pitot tube is mounted using a suitable mounting arrangement. Additionally, only one pressure sensor may be used and its readings compared against a threshold, rather than using two pressure sensors. The pitot tube can be coupled to a differential pressure sensor that is then coupled to the controller. The differential pressure sensor is configured to measure the pressure difference that is processed by the controller to determine a pressure difference in the pitot tube. The controller can output a normal flow condition or a reverse flow condition.

The pressure sensor(s) and/or pressure sensing devices disclosed above can be in electronic communication with a controller. The controller can be a controller of the gases source or a controller of the humidifier. The controller can receive measurements from the pressure sensor(s) and/or pressure sensing devices and process the received measurements. The controller can determine a reverse flow condition and/or indication of incorrect connections as described herein. The electrical communication can be wired or wireless.

Processes Based on Mechanical Components

The humidification system can include various types of mechanical structures set up to detect connections errors. These structures can provide visual cues to the user of the humidification system when there is incorrect flow.

Figure 13A:
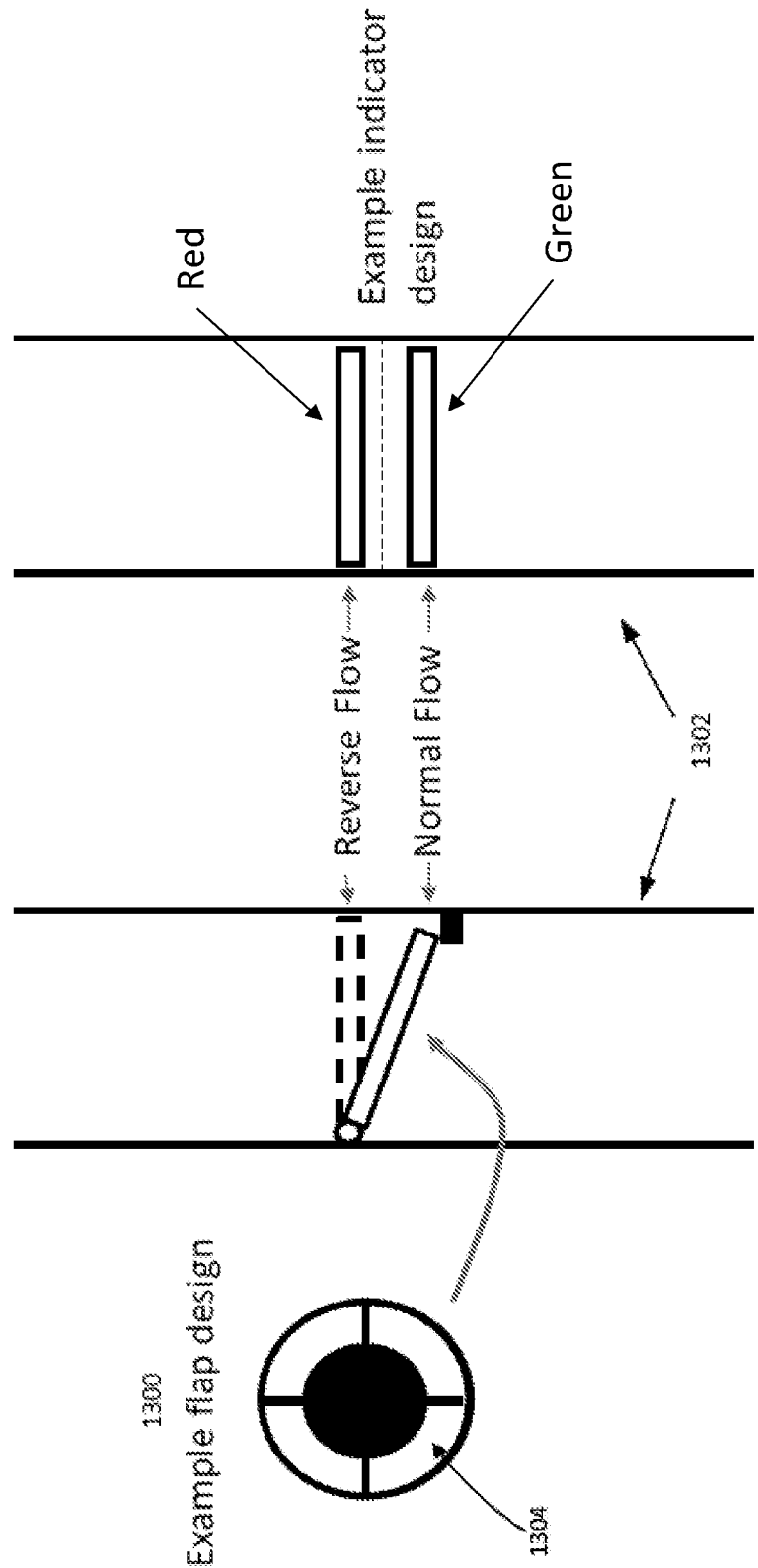

FIG. 13A illustrates a flap 1300 positioned across a cross-section of a conduit 1302 of the humidification system. The flap 1300 can be hingedly coupled to an inner wall of the conduit 1302. The flap 1300 can be circular in shape, or have a shape that is similar to the cross-section of the conduit. The flap 1300 can include one or more apertures 1304 configured to allow the gases to flow therethrough. The flap 1300 can be configured to move between a first position corresponding to normal flow conditions and a second position corresponding to incorrect flow i.e. reverse flow. When in the first position (in a normal flow condition), the flap 1300 may form an angle with respect to a transverse axis of the conduit 1302. The flap 1300 can be configured such that during normal flow conditions, the flap 1300 does not move, but during incorrect flow, the flap may incline, decline, or block the conduit 1302.

The flap shown in FIG. 13A can be incorporated with an indicator that can change color depending on the flow direction. When the flap is in the first position corresponding to the normal flow condition, the indicator can be in a first color (such as green). On the other hand, when the flap is in the second position corresponding to an incorrect flow condition, the indicator can be in a second color different from the first color (such as red). The flap may be located in the inspiratory conduit and/or the expiratory conduit. In some examples, the indicator can include a first marker of a first color and a second marker of a second color. The markers can be positioned in a tube or a conduit. The first marker and second marker can be spaced apart. The flap can be moveable between a first position and a second position. When in a first position, the flap can align with the first marker. When in a second position, the flap can align with the second marker. A reverse flow condition can be visually indicated to a user based on the position of the flap. For example, a normal flow condition can be indicated when the flap is in the first position adjacent the first marker of a first color. A reverse flow condition can be indicated when the flap is in a second position adjacent the second marker of a second color.

The humidification system can include one or more flaps. The one or more flaps can be positioned different locations of the humidification system.

FIG. 13B illustrates valves for indicating incorrect flow conditions. The valve 1306 can be a one-way valve that allows gases to flow during normal flow conditions but not during incorrect flow conditions. During normal flow conditions, the valve 1306 can move to an open position to enable flow across the conduit. During incorrect flow conditions, the valve 1306 can be at a closed position to prevent the flow across the conduit. A blockage in one of the conduits of the humidification system could trigger an alarm indicative of incorrect flow. As shown in FIG. 13B, the valve can include flaps that are straight when in a closed position and curved when in an open position. In the illustrated example, the valve can be a one way valve that includes two flaps. Optionally, the valve can include more than two flaps or just one flap. A flow sensor 1308 on the humidifier may be able to detect this blockage and trigger the alarm.

The flow sensor 1308, as in the illustrated example, may be located upstream (that is, located opposite of the direction of normal flow) from the valve. During normal flow conditions, the flow sensor 1308 will detect a flow and determine a flow rate. On the other hand, the flow sensor 1308 may not detect a flow when incorrect flow conditions are present. The detection of no flow by the flow sensor 1308 can be indicative an incorrect flow condition, which can be an indication of an incorrect connection in the humidification system. The arrangements of FIGS. 13A and 13B may be positioned in an inspiratory conduit or at an outlet of the chamber. Alternatively the arrangements of FIG. 13A and FIG. 13B may be located in an expiratory tube.

The flow sensor disclosed above can be in electronic communication with a controller. The controller can be a controller of the gases source or a controller of the humidifier. The controller can receive measurements from the flow sensor and process the received measurements. The controller can determine a reverse flow condition and/or indication of incorrect connections as described herein. The electrical communication can be wired or wireless.

Figure 14:
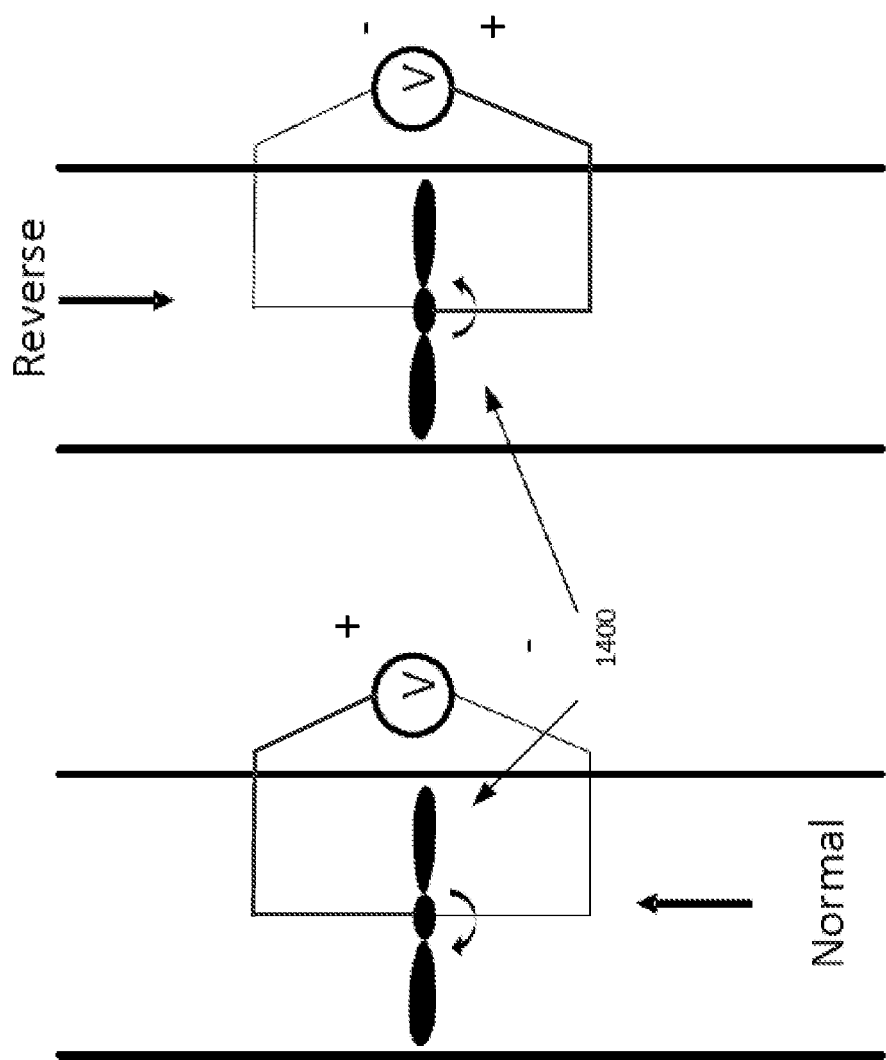

FIG. 14 illustrates a turbine 1400 configured to rotate in different rotational directions under different flow directions. The rotational direction of the turbine within a conduit may indicate a direction of a flow by detecting a direction of an electrical current generated by movement of the turbine 1400. The direction of electrical current may be determined by sensing the positive and negative terminals of the turbine. The relative voltage difference can be indicative of the direction of the current, and thus, the rotational direction of the turbine. The shaft of the rotor may be connected to a Hall Effect sensor, which is an arrangement of a current flowing coil and a magnet connected to a shaft of the rotor. Thus, when the rotor rotates, a voltage and/or pulse is induced. As shown in FIG. 14, the turbine can rotate clockwise during normal flow conditions and rotate counter-clockwise during incorrect flow conditions. The direction of the turbine during normal and incorrect flow conditions can also be reversed.

The Hall Effect sensor disclosed above can be in electronic communication with a controller. The controller can be a controller of the gases source or a controller of the humidifier. The controller can receive measurements from the Hall Effect sensor and process the received measurements. The controller can determine a reverse flow condition and/or indication of incorrect connections as described herein. The electrical communication can be wired or wireless.

Figure 15:
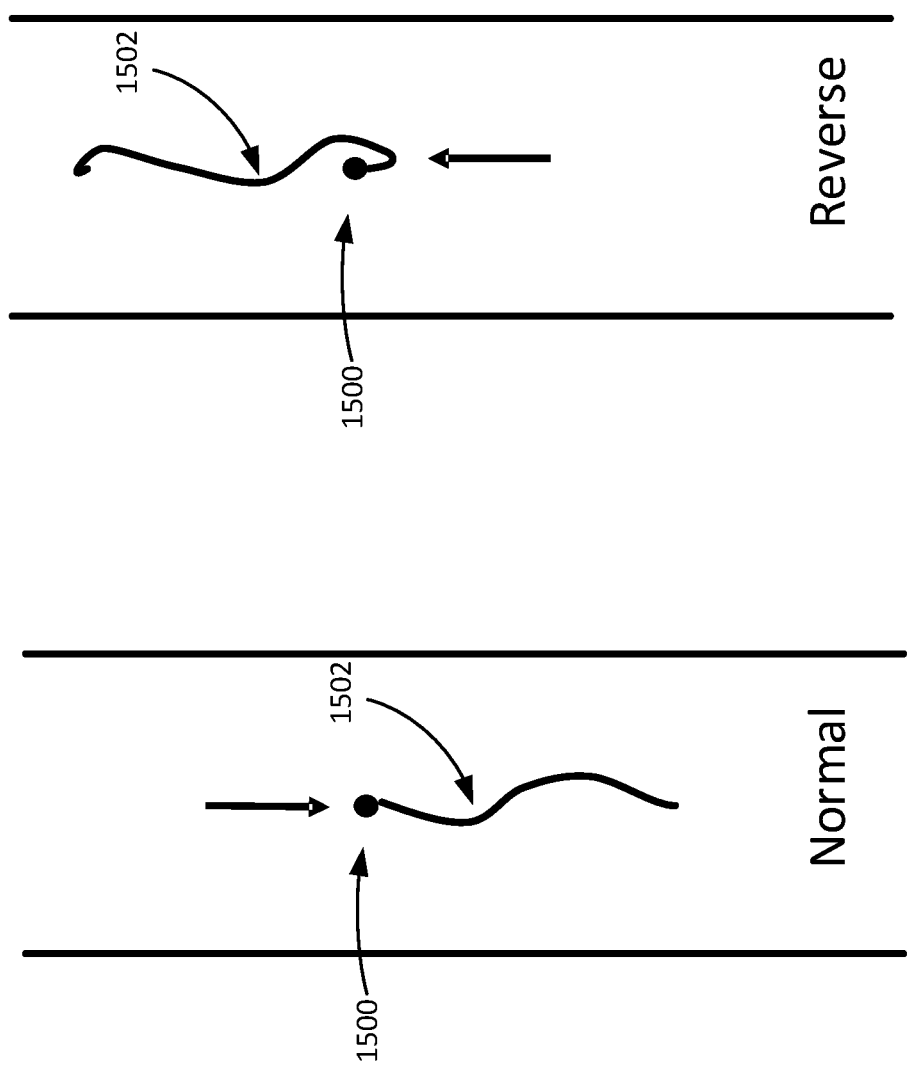

FIG. 15 illustrates a flexible attachment that can include a head 1500 and a tail 1502. The head 1500 can be fixedly attached to an inner surface of a conduit of the humidification system. The tail 1502 can include a first end attached to the head 1500 and a second end positioned opposite from the first end. The tail 1502 can be configured to move in a direction corresponding to a flow direction through the conduit. The tail 1502 can allow visual indication between normal flow conditions and reverse flow conditions as shown in FIG. 15. As shown in FIG. 15, the tail 1502 includes a substantially 180° turn near the first end in a reverse flow condition. The flexible attachment including the head and tail can be mounted into one of the conduits, for example, the inspiratory conduit or expiratory conduit or within a port of the humidifier chamber.

Figure 16:
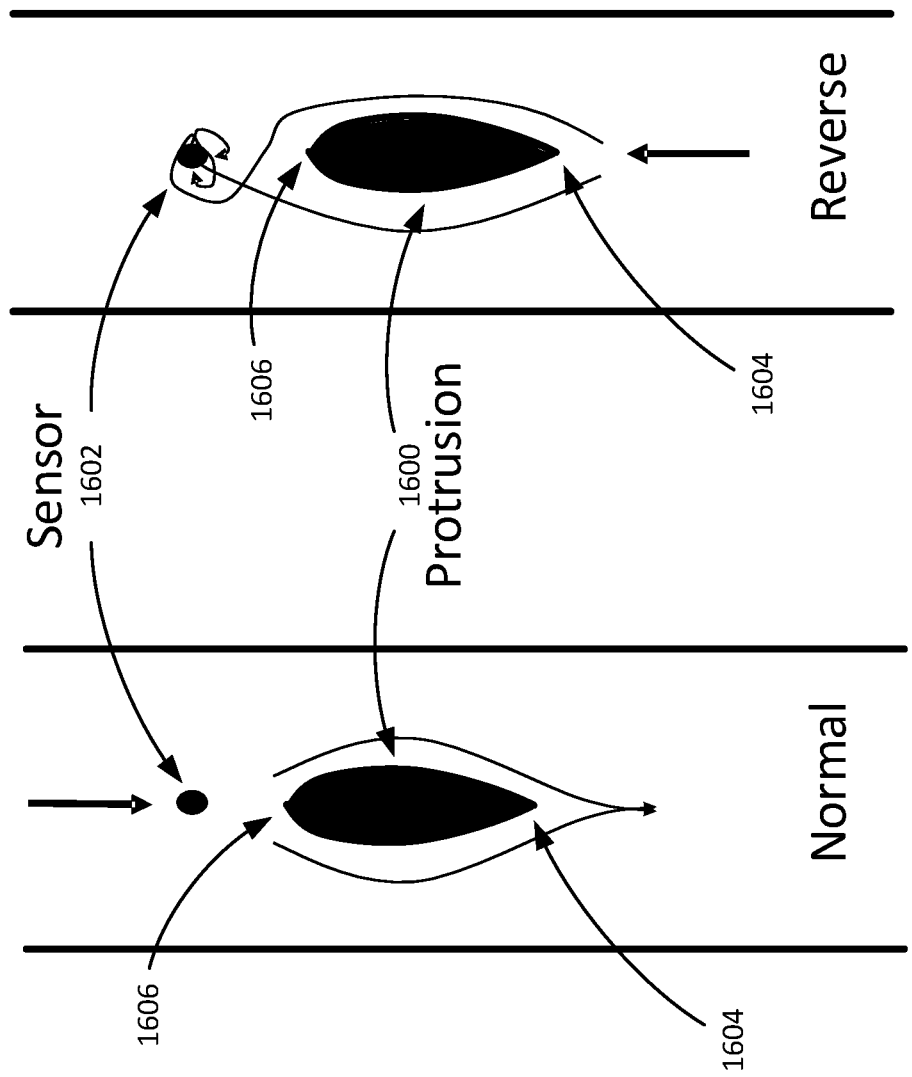

FIG. 16 illustrates a protrusion 1600 may be positioned within a conduit. The protrusion 1600 can be shaped to create flow patterns that may be detectable either visually or by a sensor 1602 that can detect alternative vortices. For example, during normal flow conditions the protrusion 1600 may cause little to no change to flow characteristics. During reverse flow conditions, the protrusion 1600 can create turbulence or vortices that are visible or about the sensor 1602 configured to detect the alternating vortices. The protrusion 1600 can be a bluff body. The protrusion can include a first end 1604 and a second end 1606, where the first end 1604 has a narrower tip and the second end 1606 has a rounder tip. In some examples, the protrusion can be in a shape of a teardrop. As noted above, the shapes of the first end 1604 and the second end 1606 can create flow patterns that may be detectable either visually or by the sensor 1602. The protrusion can be positioned such that the second end 1606 faces towards the sensor 1602 while the first end 1603 faces away from the sensor 1602.

The protrusion 1600 may be moulded into one of the conduits (for example, the gases delivery conduit 40 and the gases transport conduit 50). Alternatively, the protrusion 1600 may be located in the outlet of the humidification chamber of the humidifier 20. The protrusion may be dimensioned and sized so that it does not significantly reduce flow within the humidification system 1 (for example, in the conduits and/or the humidification chamber).

Processes Utilizing a Flow Path Controller

The humidifier can include two ports that are connected to the outlet of the gases source and the inlet of the gases source, where either port can be connected to the outlet and the inlet. The humidifier can direct the flow path such that the incoming gas from the ventilator is humidified before it reaches the patient, irrespective of which humidifier port the incoming gas is connected to.

Figure 17:
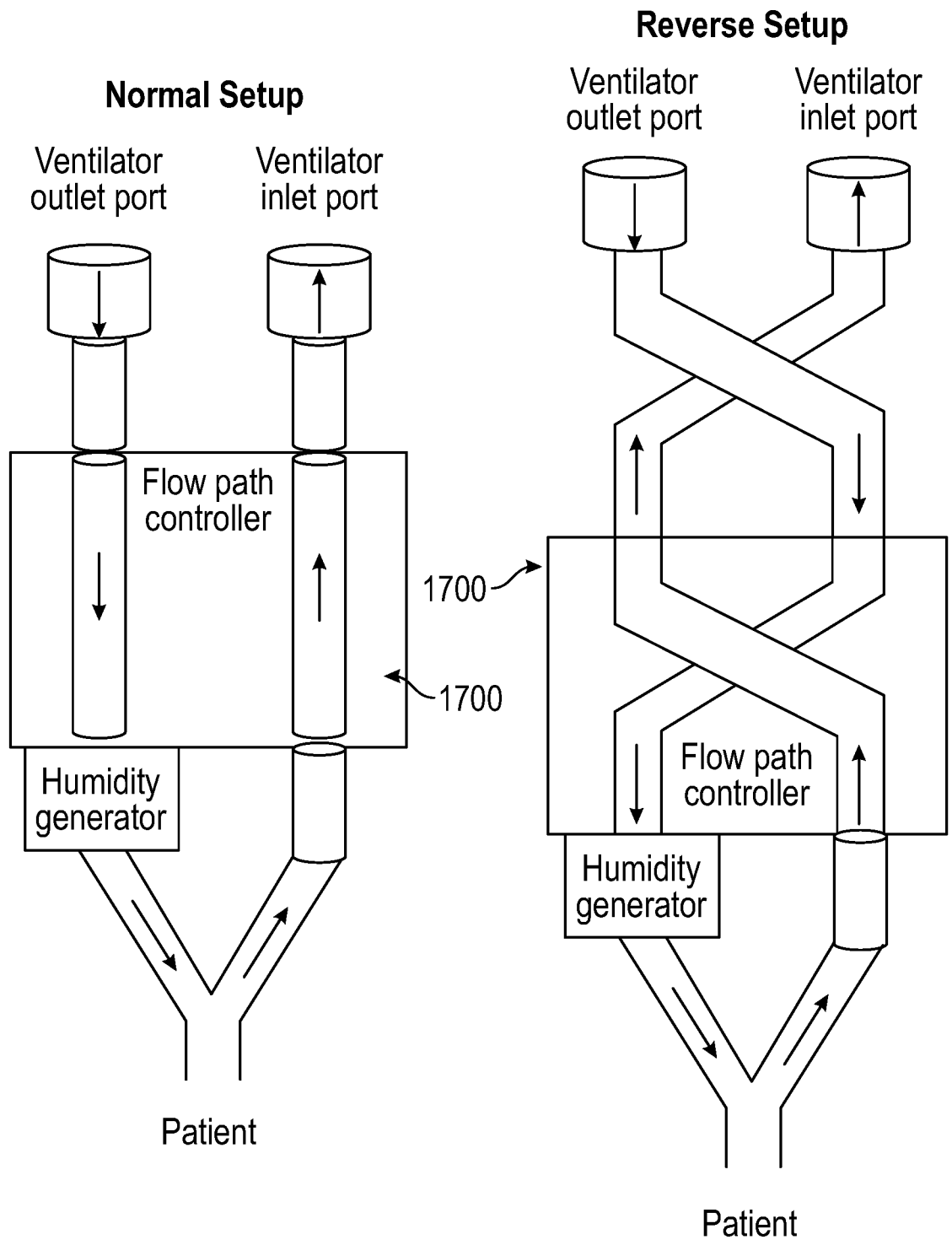
FIGS. 17 and 17A illustrate an example flow path controller setup configured to detect and rectify incorrect flows.
Figure 17A:
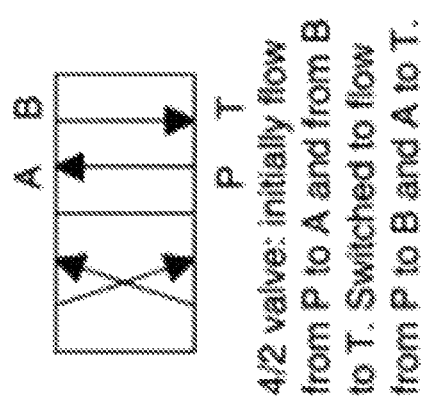

FIG. 17 illustrates an example flow path controller 1700. Switching of the flow path may be achieved, for example, using a 4/2 valve in the flow path controller 1700. FIG. 17A illustrates an example illustration of the 4/2 valve. The 4/2 valve can be arranged such that gases can flow from point P to point A and from point B to point T. The 4/2 valve can be actuated so that gases can flow from point P to point B and from point A to point T instead. Using the flow path controller 1700 and the 4/2 valve, gases flow direction in the humidification system can be changed. For example, as shown in FIG. 17, the 4/2 valve and the flow path controller 1700 can be arranged such that when in a normal setup, gases flow from the ventilator outlet port to the humidity generator and from the patient to the ventilator inlet port. However, when there is an incorrect connection that can cause gases to flow from the ventilator outlet port to the patient and from the humidity generator to the ventilator inlet port, the flow path controller 1700 can rectify the reverse flow condition by switching to reverse set up as shown in FIG. 17. The reverse setup can change direction of the flow of gases in the humidification system by changing configuration of the flow path.

The humidifier can use one or more flow sensors to detect which of its ports is connected to the ventilator outlet and direct a flow from the ventilator outlet to the humidity generator. Alternatively and/or additionally, the humidifier can use one or more pressure sensors to detect which of its ports is connected to the ventilator and redirect the flow path appropriately. The valve may be controlled by a controller of the system (for example, a controller of the humidifier) to direct flow in the correct direction and avoid a reverse flow condition.

Alternatively, control of the flow can be done on the ventilator, which can control which ventilator port is used as the outlet after determining which ventilator port is connected to the humidifier's inlet and/or outlet port. The flow path controller can be integrated as part of the humidifier or connected upstream of the humidifier.

The one or more flow sensors disclosed above can be in electronic communication with a controller. The controller can be a controller of the gases source or a controller of the humidifier. The controller can receive measurements from the one or more flow sensors and process the received measurements. The controller can determine a reverse flow condition and/or indication of incorrect connections as described herein. The electrical communication can be wired or wireless.

Processes Based on Condensation Detection at Humidification Chamber Inlet

During a normal flow condition, condensation tends to form on the humidification chamber outlet, from which the humidified gases exit the chamber. The gases can be cooled by the wall of the chamber outlet, which is exposed to ambient conditions. During a normal flow condition, there tends to be significantly less or no condensation that forms on the inlet of the chamber as the incoming gases from the dryline are typically dry and/or cooler than the gases exiting the chamber. During a reverse flow condition, condensation can form on the chamber inlet because the heater plate can become energized and heat up the gases travelling from the chamber outlet to the chamber inlet. When the chamber outlet set point is not reached, an increased power is supplied to the heater plate. The ambient temperature outside the chamber is typically lower than the temperature of the gases. The connections around the chamber outlet are typically not heated. In other words, there is typically a section between the inspiratory conduit and the chamber which is not heated. Due to the typically colder ambient temperature (relative to the humidified gases), a net heat transfer is created from the inside of the chamber to the outside of the chamber. Thus, the gases flowing out of the chamber inlet in a reverse flow direction tend to condense on the inner surface of the chamber inlet or on a region near the chamber inlet. Even if power to the heater plate of the chamber has reduced or been disabled, the gases can still be humidified as the gases travel from the chamber outlet to chamber inlet if the temperature of the water is relatively high compared with the temperature of the gases.

The presence of condensation can be detected directly (for example, by detecting the moisture itself) or indirectly (for example, by detecting a predetermined temperature change of the inner surface of, or near, the chamber inlet). The presence of condensation can be detected by any suitable sensors, for example, a humidity sensor, which can optionally be a capacitive sensor, an optical sensor, or any other moisture sensors, or a thermopile or other suitable temperature sensors that can detect the temperature change of the inner surface. The sensors can be configured to measure a parameter associated with formation of condensation on the inner surface of the inlet of the chamber. Optionally, the sensor can be coupled to an inlet port of the humidification chamber. The sensor can be located within the humidifier itself or be an intermediate component configured to be coupled to the humidifier (for example, in a sensor cartridge removably engageable with the humidifier and/or humidification chamber).

Figure 18A:
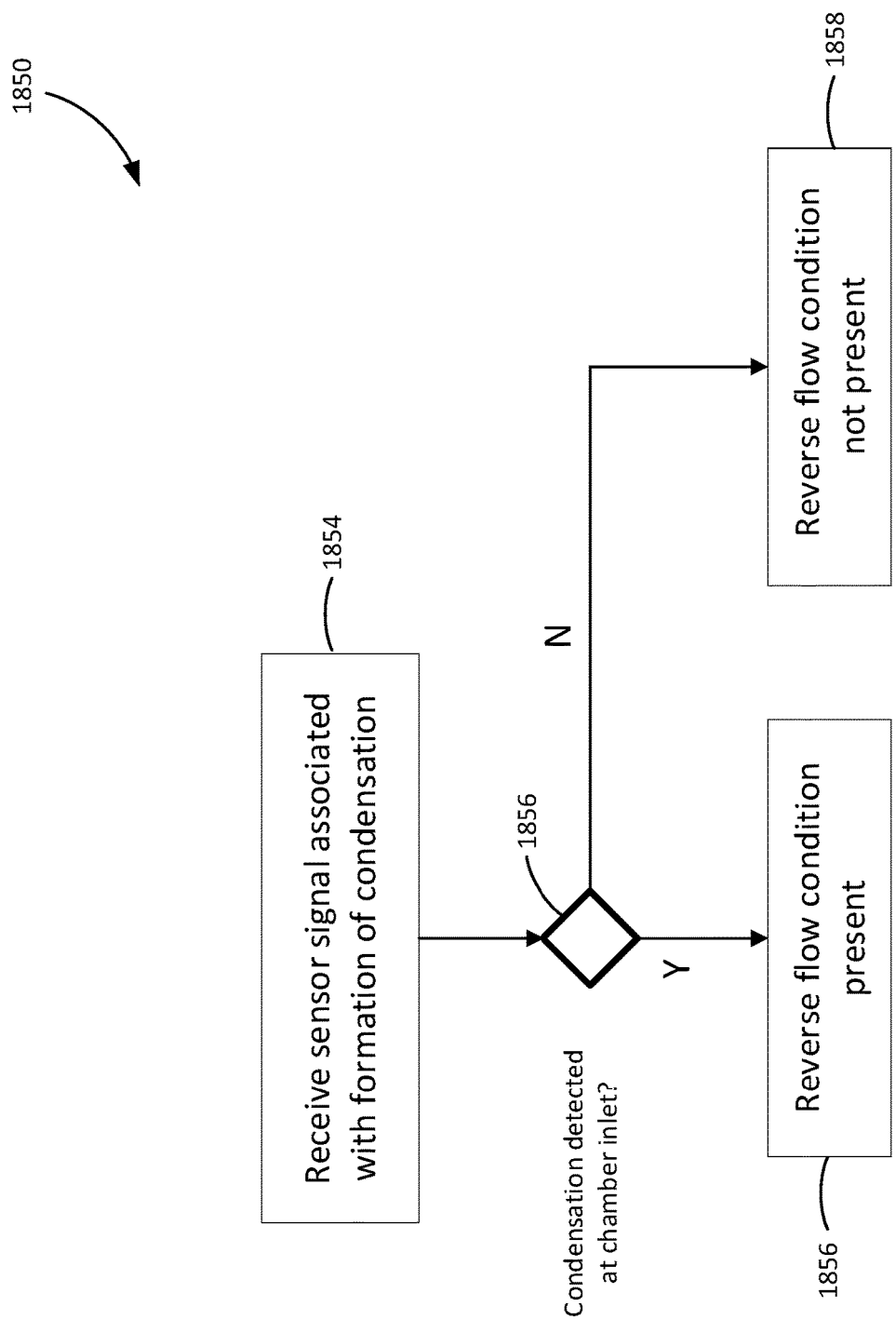
FIG. 18A illustrates an example method of detecting incorrect flow based on moisture detection at a chamber inlet.

As shown in the method 1850 of FIG. 18A, the controller of the humidification system can begin a reverse flow detection algorithm by receiving a signal from a sensor in the humidification system at step 1854. The signal can be indicative of the presence of condensation at or near the inner surface of the inlet of the humidification chamber. At decision step 1856, the controller can determine whether condensation is present on the inner surface of the chamber inlet. If condensation is detected on the inner surface of the chamber inlet, this may indicate the humidifier is connected incorrectly and the controller can output a determination that reverse flow is present at step 1860. If condensation is not detected on the inner surface of the chamber inlet, the controller can determine that reverse flow is not present at step 1858. Alternatively, the sensor could be provided on the outlet of the chamber, in which case an absence of condensation can be indicative of reverse flow.

Figure 18B:
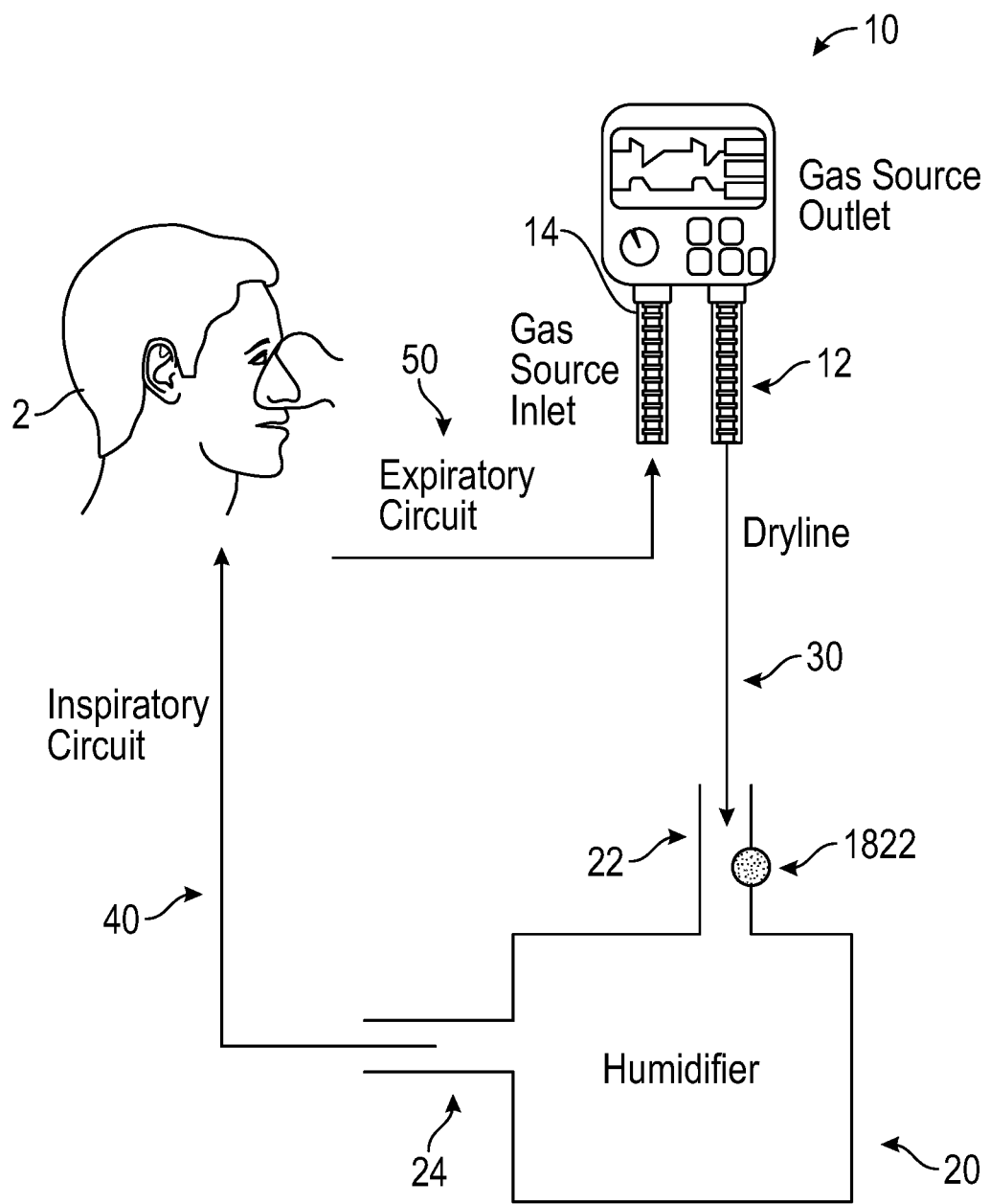
FIG. 18B illustrates example setup for detecting moisture at an inlet of a humidification chamber.

FIG. 18B illustrates an example humidification chamber 20 of the humidification system disclosed herein. The humidification chamber 20 can include a sensor (or sensors) 1822 located at or proximate the chamber inlet 22. The sensor or sensors may or may not be in direct contact with the gases flow. In some configurations, the sensor or sensors may or may not be in direct contact with the humidification chamber of the humidifier 20. In some configurations, the sensor or sensors may be housed within the humidifier 20. The sensor or sensors 1822, as discussed above, can measure a parameter associated with formation of condensation on the inner surface of the chamber inlet 22 proximate the chamber inlet 22, or a sidewall of the humidification chamber 20. Alternatively, the chamber can include a deflection assembly configured to deflect the incoming gases to a region of the side wall of the humidification chamber. The sensor can be configured to sense a parameter at that region (irrespective of the direction of the gases). The sensor 1822 and the configuration shown in FIG. 18B can be used to execute the method 1850. The method 1850 may be executed by the controller of the humidifier, which can be the humidifier 20 and/or the gases source 10.

Upon detecting reverse flow/incorrect connection conditions, the controller of the humidifier can output a signal or alarm for presence of reverse flow/incorrect connection conditions and/or display the electronic indicator. The humidifier can optionally include a display module for displaying the signal or alarm.

Figure 18C:
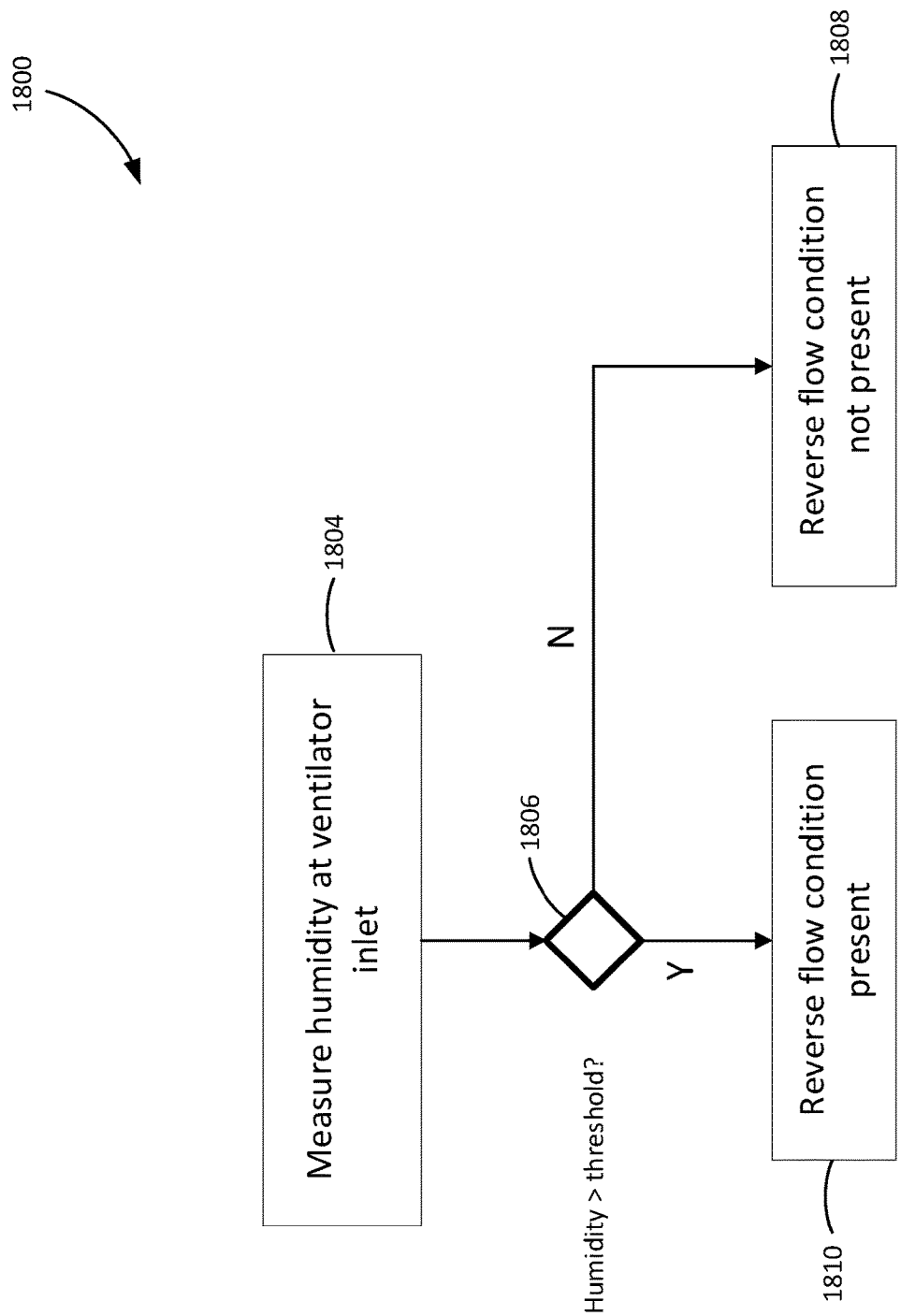
FIG. 18C illustrates an example method of detecting incorrect flow based on humidity measurement at a gases source inlet.

Processes Based on Humidity Detection at Gases Source (for Example. Ventilator) Inlet Detection of reverse flow conditions can also be carried out at the gases source supply side. The humidifier may generate an unexpected level of humidity when the flow passing through the humidifier is reversed. As shown in the method 1800 of FIG. 18C, the controller of the gases source (which may be the same as the controller of the humidification system or a separate controller) can begin a reverse flow detection algorithm. At step 1804, the gases source controller can determine the humidity at the inlet ("from patient") port of the ventilator, such as via input from a humidity sensor at that location. At step 1806, the controller can determine whether the measured humidity exceeds a threshold. If the measured humidity is outside of the expected humidity level, this may indicate the humidifier is connected incorrectly and the controller can output a determination that reverse flow is present at step 1810. If the measured humidity is not above the threshold, the controller can determine that reverse flow is not present at step 1808. Optionally, the humidity sensor can be coupled to an outlet ("to patient") port of the ventilator.

Figure 18D:
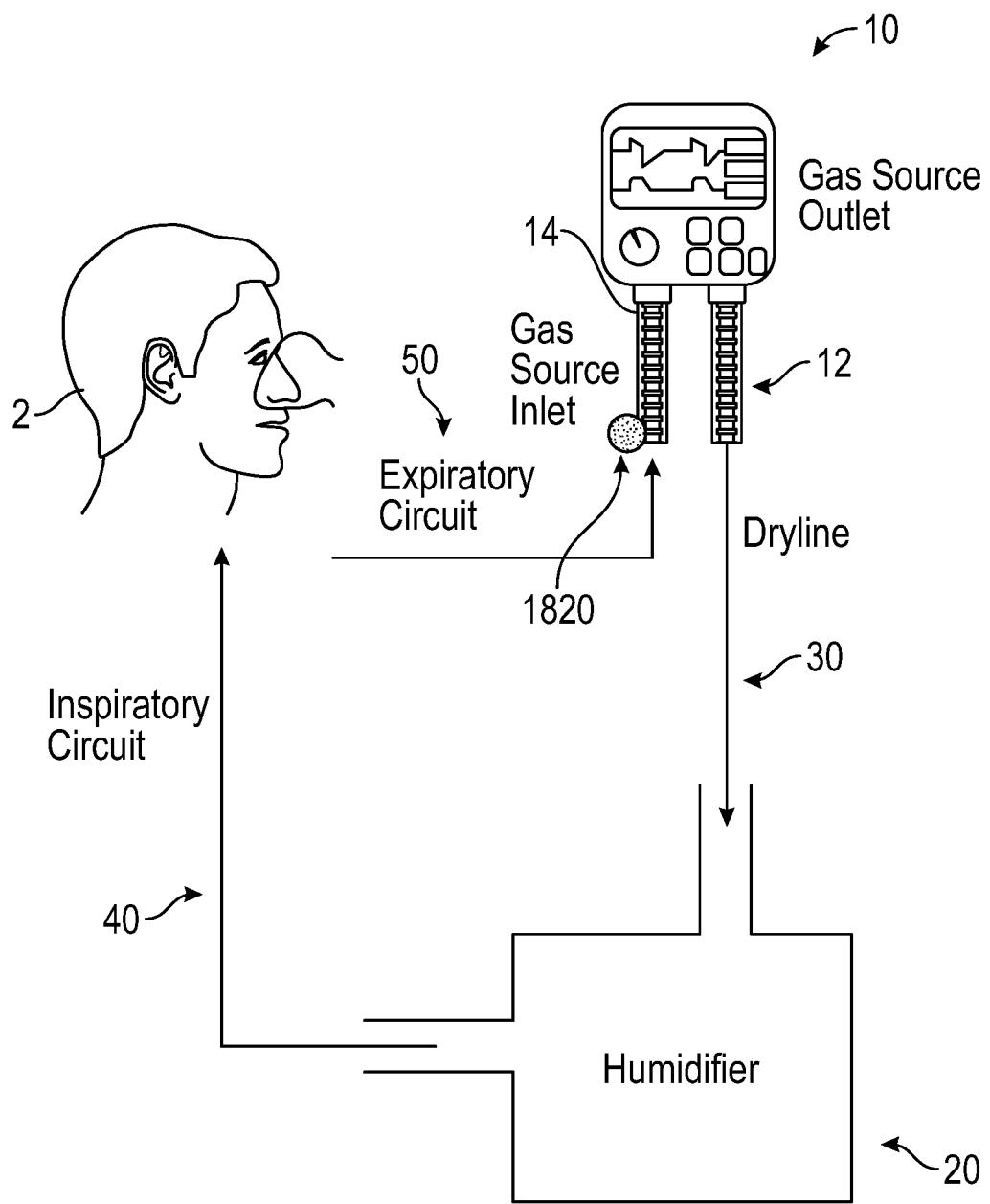
FIG. 18D illustrates example setup for measuring humidity at the gases source inlet gases source.

FIG. 18D illustrates an example gases source 10 of the humidification system disclosed herein. The gases source 10 can include a sensor 1820 coupled to the inlet 14. The sensor 1820, as discussed above, can measure humidity at the inlet 14 of the gases source 10. The sensor 1820 and the configuration shown in FIG. 18B can be used to execute method 1800. The method 1800 may be executed by the controller of the gases source.

The gases source can have a controller. The controller of the gases source may detect reverse flow/incorrect connection conditions, such as using the processes disclosed herein. Upon detecting reverse flow/incorrect connection conditions, the controller of the gases source can output a signal or alarm for presence of reverse flow/incorrect connection conditions and/or display the electronic indicator. The gases source can optionally include a display module for displaying the signal or alarm.

The humidity sensor disclosed above can be in electronic communication with a controller. The controller can be a controller of the gases source or a controller of the humidifier. The controller can receive measurements from the humidity sensor and process the received measurements. The controller can determine a reverse flow condition and/or indication of incorrect connections as described herein. The electrical communication can be wired or wireless.

Processes Based on Tube/Conduit Identification

Figure 19:
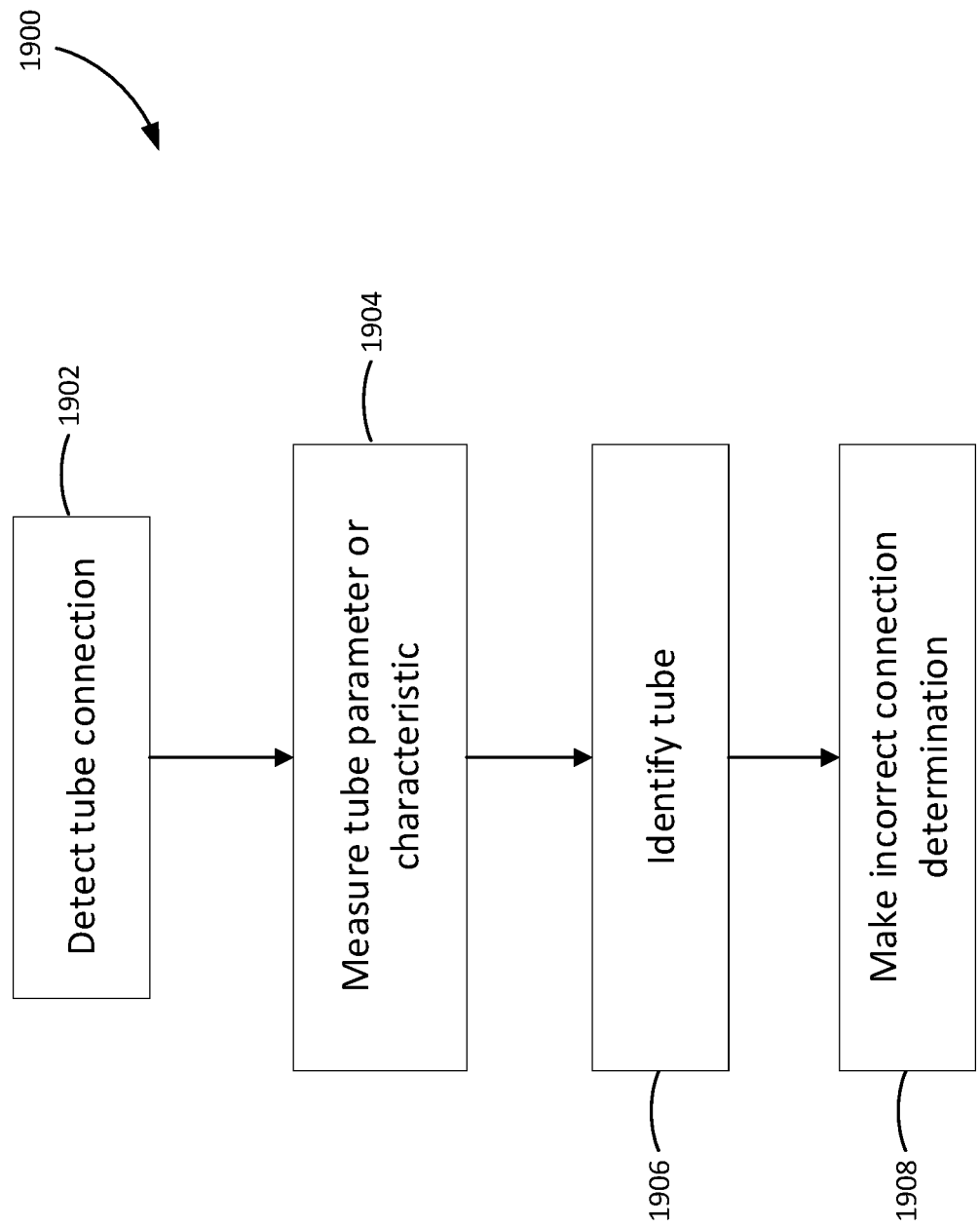
FIG. 19 illustrates an example method of detecting incorrect connection based on tube identification.

As shown in a method 1900 in FIG. 19 the gases source (for example, the ventilator) controller may detect presence of a conduit or tube being connected to its inlet and/or outlet port at step 1902. Specifically, the method 1900 may be used to detect the type of the tube and/or identifying the tube connected to a gases source of the humidification system 1. At step 1904, the controller can determine a parameter or characteristic of the tube. The controller can identify the type of tube connected at the ventilator's outlet and/or inlet gas ports based on the parameter or characteristic. The inspiratory conduit and the expiratory conduit may have different properties to allow the ventilator to identify the type of conduit connected at step 1906. At step 1908, the controller can use the tube identification information to determine whether a conduit is connected incorrectly to one or multiple gas ports. Alternatively, the humidifier controller may detect presence of a conduit or tube being connected to the inlet and/or outlet of the humidifier.

An example of tube identification can involve resistance detection. Each tube type may have a different embedded identification resistor or heater wire resistance, which can be detected when coupled to the ventilator. The different types of tubes can each have different resistance values. When connected, the ventilator can apply a voltage (or induce a current) and measure the current (or voltage) to differentiate different types of tubes.

Different types of tubes can also be distinguished using radio-frequency identification (RFID) technology. Each tube type can have a different RFID tag that may be active, passive, or semi-passive. The ventilator and/or humidifier can include an RFID reader on the inlet and/or the outlet to read the RFID tag on the tubes. The RFID reader of the ventilator can include an RF signal generator, receiver/signal detector, and a controller.

Each type of tube can alternatively and/or additionally include a different barcode or a QR code that can be detected by the ventilator when connected.

Different types of tubes can also be distinguished using different colors and/or different electromagnetic properties including, but not limited to, absorption, emission, reflection, and/or refraction properties. The ventilator can include optical sensor that may detect the color or the different characteristics of the electromagnetic wave emitted or reflected by the different types of tubes.

Example characteristics of the tube can also include features that may be present or not present at different physical locations. The feature may include a conductive surface or a component whose presence that can be detected. The feature may include a component that produces a detectable response to different types of signals including, but not limited to an electric field, magnetic field, electromagnetic signal, acoustic signal, and the like. The feature can include a structural feature that can be optically detected. The feature may be detected using any detection method discussed herein. The detection method can also include detection of functional features in the tube such as detecting the presence of a heater wire by measuring inductance, magnetic field, and/or heater wire resistance.

Each tube type may also include a magnet installed with different polarity facing the gases source. For example, the dryline and the expiratory conduit can be identified by having the opposite polarity facing the gases source. The inspiratory conduit can be detected, for example, by the absence of a magnet. Alternatively, each tube type may have two or more magnets, or the position or magnetic field of the magnets may be varied to permit identification of a wider range of tubes. The gases source can include a corresponding sensor that can detect the polarity of the magnet and therefor the tube type. The ventilator can also include magnets such that the incorrect tube configuration can result in the tube being repelled by the gases source connector.

The tube identification devices and/or sensors disclosed above can be in electronic communication with a controller. The controller can be a controller of the gases source or a controller of the humidifier. The controller can receive measurements from the tube identification devices and/or sensors and process the received measurements. The controller can determine a reverse flow condition and/or indication of incorrect connections as described herein. The electrical communication can be wired or wireless.

Processes Based on Ventilator Connector Geometry

The gases source (for example, the ventilator) can include connectors that may be provided with differing physical shapes and/or dimensions as a mechanism to prevent incorrect connections. For example, the gases source outlet port can be designed to only fit the inspiratory tube and the gases source inlet port can be designed to only fit the expiratory tube.

This may prevent incorrect connections to the gases source since the tubes could not be connected to the ventilator unless the correct tube connector is coupled to the gases source inlet or outlet.

Example differing connections features can include, but are not limited to, 22 mm taper inlet and 20 mm taper outlet, square inlet and circular outlet, keyed connectors and/or shapes or written text on the connectors.

Processes Based on User Assistance

Figure 20:
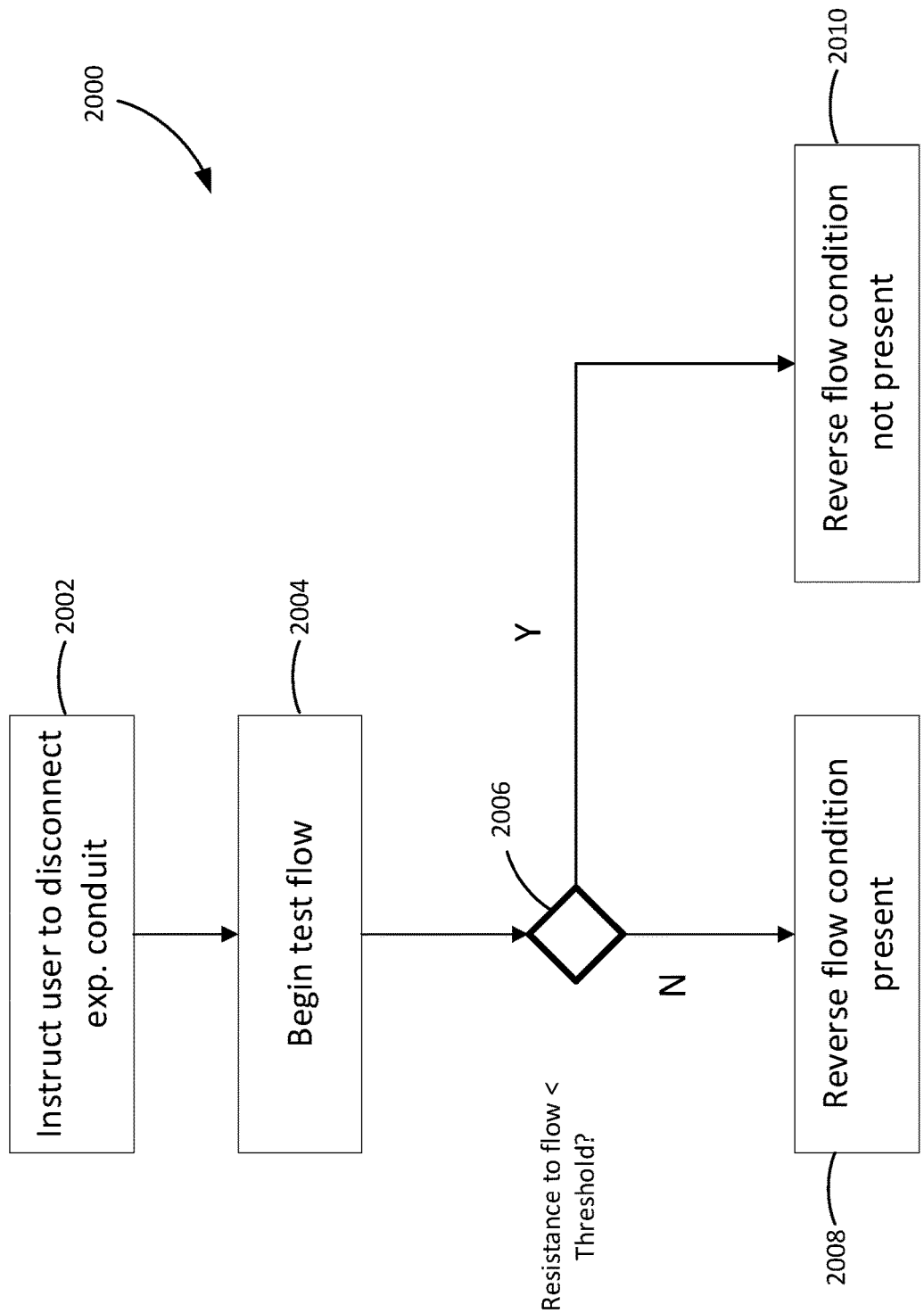
FIG. 20 illustrates an example user-assisted method of detecting incorrect connection.

Assistance from a user and/or caregiver may be used to detect incorrect connections in the humidification system. In an example method 2000 of FIG. 20, the ventilator controller can instruct a user, for example, via messages and/or audible cues on a display of the humidification system, to disconnect the expiratory conduit 50 at step 2002. The controller can also optionally instruct the user to connect the inspiratory conduit 40 in addition to disconnecting the expiratory conduit. At step 2004, the ventilator controller can cause the ventilator to generate a test flow to be provided to its outlet port. At step 2006, the ventilator controller can determine if the expiratory conduit was disconnected from the outlet port or from the inlet port, such as by determining whether a resistance to flow at the outlet port exceeds a threshold. The resistance to flow may be determined from a pressure measurement, a flow rate measurement, or otherwise, at the outlet port. In a correct set up, the expiratory conduit can be disconnected from the inlet port and the ventilator may detect a high resistance to flow when providing air at the outlet port, which is still connected to the dryline. In an incorrect set up (the expiratory conduit was connected to the outlet port), the ventilator may detect a lower resistance to flow when providing air at the outlet port as the outlet port is no longer connected to a tube. If the resistance to flow is below the threshold, the controller can determine reverse flow is present at step 2008. If the resistance to flow exceeds the threshold, the controller can determine reverse flow is not present at step 2010.

The devices or sensors for determining the resistance to flow disclosed above can be in electronic communication with a controller. The controller can be a controller of the gases source or a controller of the humidifier. The controller can receive measurements from the devices or sensors for determining the resistance to flow and process the received measurements. The controller can determine a reverse flow condition and/or indication of incorrect connections as described herein. The electrical communication can be wired or wireless.

Processes Based on Communications Between the Humidifier and Gases Source

Figure 21:
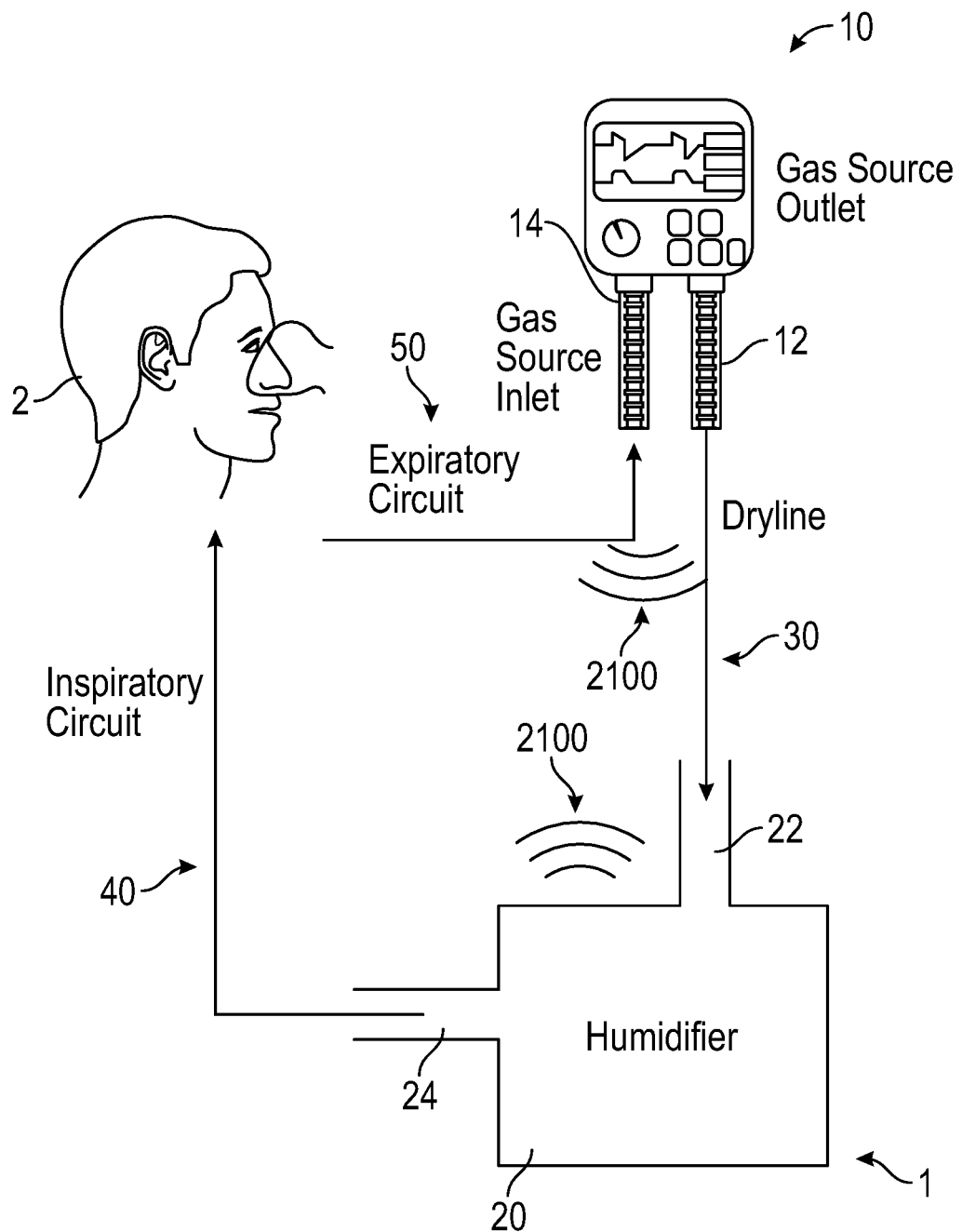
FIG. 21 illustrates an example humidification system having a gases source and a humidifier in electronic communication between each other.

An electronic communication between the humidifier and the gases source may be used to detect reverse flow conditions and/or incorrect connections. The humidifier and the gases source can be arranged so that they can establish electronic communication with each other. The electronic communication between the humidifier and the gases source can be wireless via Bluetooth®, 3G/4G/5G, near-field communication (NFC), Wi-Fi, or other types of suitable wireless communication protocols. Alternatively, the electronic communication between the humidifier and the gases source can be via a wired connection such as RS-232, USB, Ethernet, or other types of wired communication protocols. Once electronic communication is established, the humidifier and the gases source can transmit electrical signals and information between each other. FIG. 21 illustrates an example humidification system 1 including the gases source 10 and the humidifier 20 having a wireless electronic communication 2100 between each other.

Figure 21A:
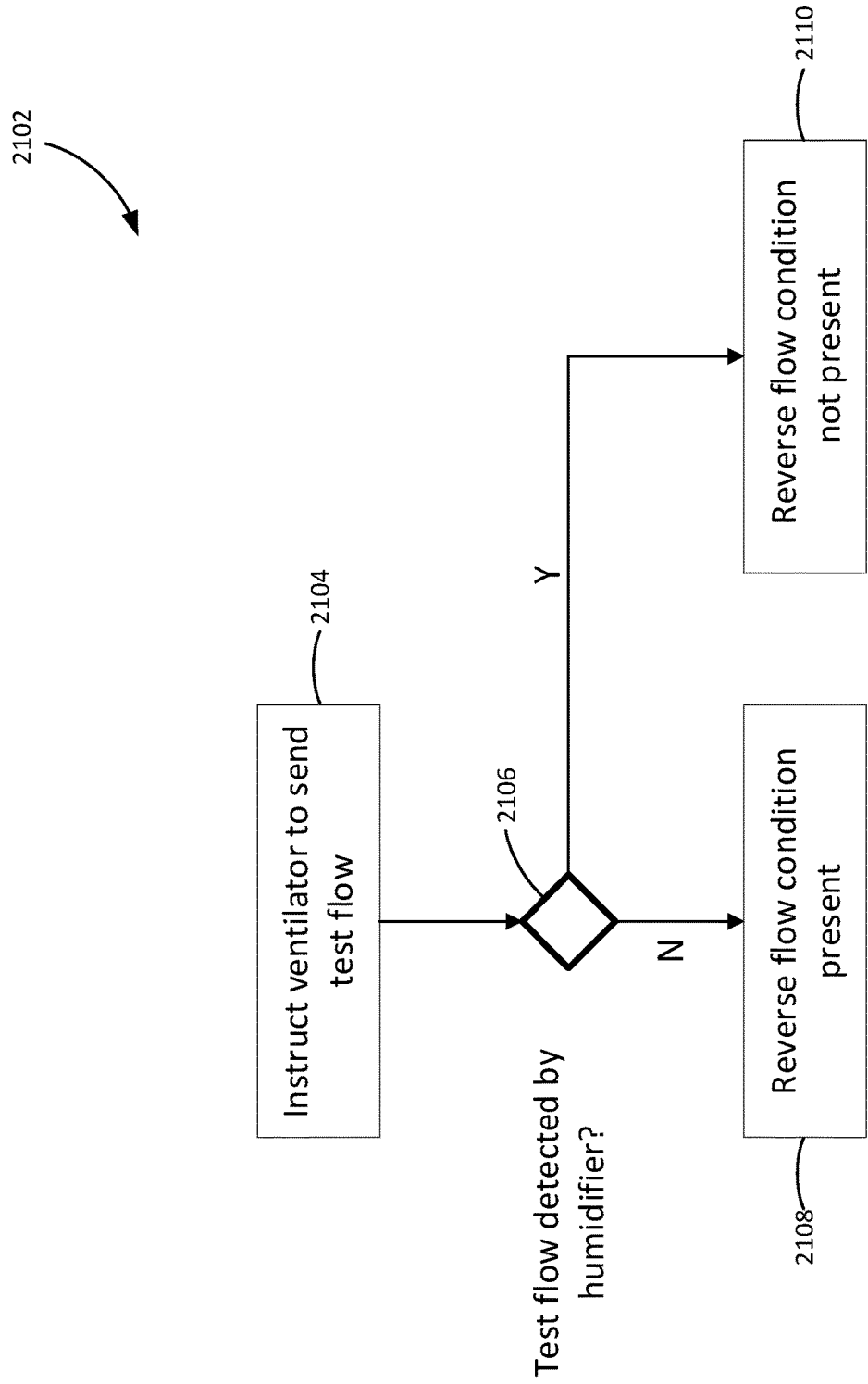
FIG. 21A illustrates an example method of detecting incorrect flow by a test flow using communication between the humidifier and the gases source.

In a method 2102 of FIG. 21A, the controller of the humidification system can begin a reverse flow detection algorithm. Alternatively, the controller of the gases source system can begin a reverse flow detection algorithm. The gases source and humidifier controllers can communicate with each other to establish when the test procedure will begin and when the humidifier should expect to measure this response. At step 2104, the controller can instruct the ventilator to send a test flow. At step 2106, the controller can determine whether the test flow is detected at the humidifier inlet. During normal flow conditions, the test flow is detected by the humidifier at its inlet. During reverse flow conditions, the humidifier may not detect this test flow, or at least may not detect the expected test flow rate, as the test flow travels via a different path to the humidifier. If the expected test flow is detected by the humidifier, at step 2110, the controller can determine reverse flow is not present. If the expected test flow is not detected by the humidifier, at step 2108, the controller can determine reverse flow is present. Additionally or alternatively to flow rate, pressure can be monitored to characterize the test flow.

Additionally or alternatively, in normal flow conditions (when the tubes are correctly connected), the humidity measured at the ventilator outlet ("To Patient") port may be similar to that measured at the dryline and humidifier inlet. The humidity measured at the ventilator inlet ("From Patient") port may be similar to that measured at the end of the expiratory conduit during normal flow conditions. The controller of the humidification system and/or the ventilator can measure humidity at the ventilator outlet port, the dryline, and/or the humidifier inlet. Reverse flow conditions can be identified, for example, if the humidity measured at the ventilator outlet is significantly different than the humidity measured at the dryline and/or humidifier inlet. The controller of the humidifier and/or the ventilator can also measure humidity at the ventilator inlet port and the expiratory conduit. A significant difference between the humidity measured at the ventilator inlet and the humidity measured at the expiratory conduit may also indicate reverse flow conditions. Instead of or in addition to humidity, other parameters, such as $CO_2$ concentration, $O_2$ concentration, and/or temperature may be measured and used to detect reverse flow conditions.

The humidifier can inject a tracer into the gas stream and the ventilator can include corresponding sensors at the inlet and/or outlet of the ventilator. The ventilator and humidifier controllers can communicate with each other to establish when the tracer will be injected by the humidifier and when the ventilator should expect to detect the tracer. When the tubes are connected correctly, the ventilator can detect the tracer at the inlet. When the tubes are connected incorrectly, the ventilator can detect the tracer at the outlet. The tracer can also be injected by the patient rather than by the humidifier controller. Alternatively and/or additionally, the tracer can also be injected by the ventilator with corresponding sensors on the humidification system. Tracer can include but not limited to water, heat, carbon dioxide, or others.

The humidifier can also detect reverse flow conditions using any one of the methods disclosed above and communicate the presence of reverse flow conditions to the gases source. The humidifier can generate an electronic signal indicative of presence of reverse flow conditions and transmit the electronic signal to the gases source or a controller of the gases source. The gases source or the controller of the gases source, upon receipt of the electronic signal from the humidifier, can generate a display indicative of presence of reverse flow conditions on a user interface and/or sound an audible alarm. The user interface may be on the gases source or the humidifier. The gases source and/or humidifier may alternatively or additionally transmit the electronic signal to a remote patient monitoring station, which may sound or display an alarm.

Humidifier operation may be controlled via the controller of the gases source. Operating parameters of the humidifier can be set by the user interface that may be integrated with the gases source or the humidifier. When a reverse flow condition is detected, the user can stop the humidifier via the gases source user interface (or humidifier user interface) and stop the gases source to correct the reverse flow condition.

The methods and sensor arrangements disclosed herein can be used in the inspiratory conduit, dryline, expiratory conduit, or a portion of the chamber (for example, inlet port or outlet port). The disclosed sensing arrangements may indicate and/or determine a reverse flow condition and/or the presence of incorrect connections in the humidification system. Multiple sensor arrangements may be used within the system for providing humidified gases to detect reverse flow and/or presence of incorrect connections. The controller of the system (for example, a controller of the gases source or a controller of the humidifier) may output a signal to a user interface to indicate to the user a presence of a reverse flow condition and/or incorrect connections within the system. The user interface may be the interface of the gases source or the humidifier. The user interface may be an audio visual device (for example, a touch screen or a series of indicator lights and a speaker or multiple screens). The indication of a reverse flow condition may be replicated on the humidifier screen and the gases source screen, as the humidifier controller and gases source controller may be in electronic communication with each other. Similarly, the indication may be replicated on a screen of a patient monitoring station in electronic communication with the humidifier and/or gases source.

The sensor arrangements disclosed above can be in electronic communication with a controller. The controller can be a controller of the gases source or a controller of the humidifier. The controller can receive measurements from the sensor arrangements and process the received measurements. The controller can determine a reverse flow condition and/or indication of incorrect connections as described herein. The electrical communication can be wired or wireless.

Figure 21B:
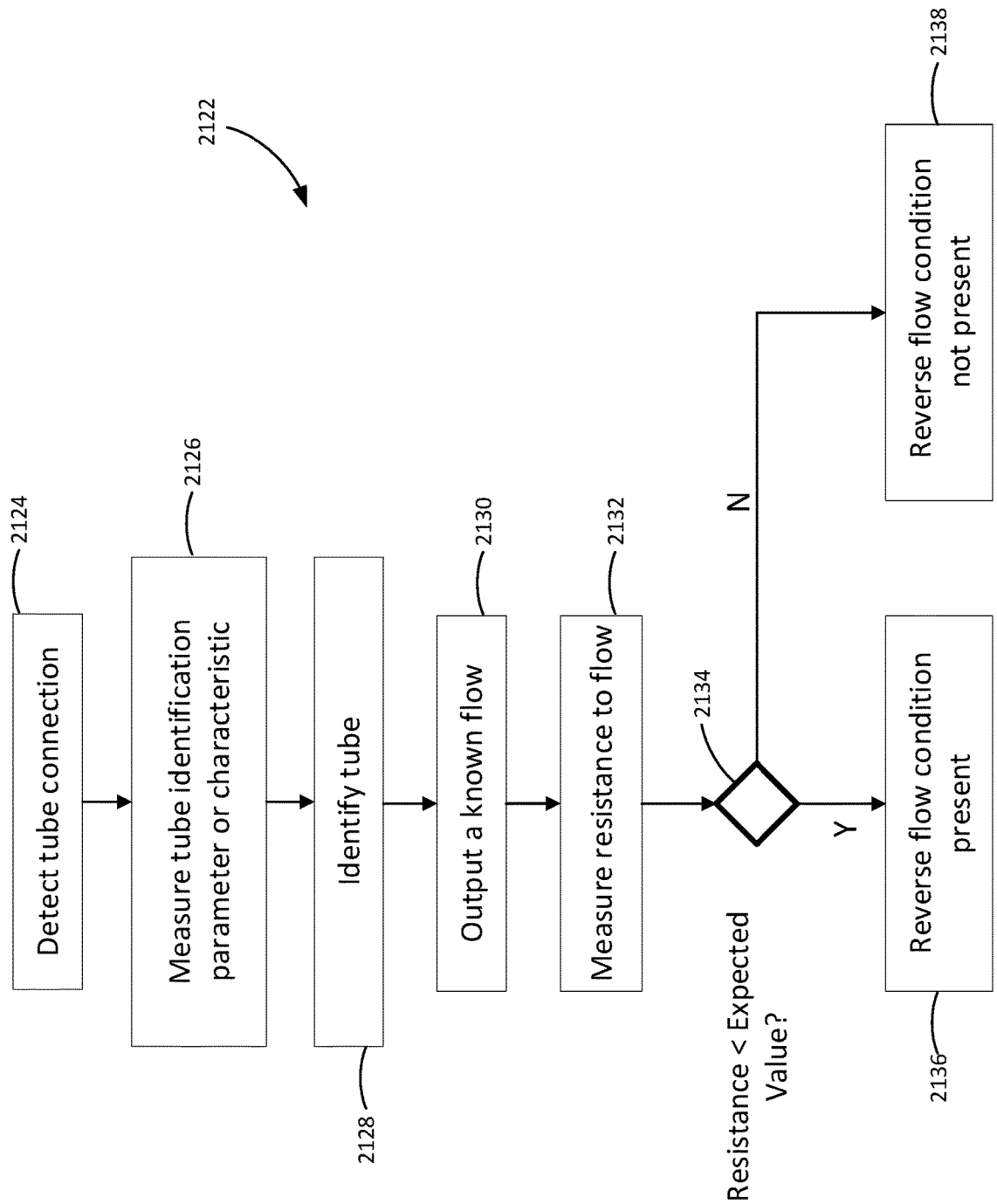
FIG. 21B illustrates an example method of detecting incorrect flow by tube identification and resistance to flow measurements.

FIG. 21B illustrates an example method 2122 that combines identification of a tube/conduit and comparison of measured characteristics and/or parameters of the tube/conduit against expected values. At step 2124, the controller of the humidifier can detect a tube connection, that is, connection of tubes connected to the inlet and/or outlet of the humidification chamber. At step 2126, the controller of the humidifier can measure a tube identification parameter or characteristic. At step 2128, the controller of the humidifier can identify the tube based on the measured tube identification parameter or characteristic. The tube identification parameter or characteristic can include, for example, a capacitance value, an inductance value, or a resistance value. Optionally, the tube identification parameter or characteristic can also include any other tube/conduit identification method disclosed herein.

The controller of the gases source and the controller of the humidifier can optionally be in communication, for example, electrical and/or data communication, with each other to perform the method 2122. At step 2130, the controller of the humidifier can communicate with the controller of the gases source to instruct the gases source to output a known flow based on the identification of the tube. At step 2132, the controller of the gases source can measure a resistance to flow value on the inspiratory side of the gases source, that is, the resistance of flow as the gases exit the outlet of the gases source. During a normal flow condition, the outlet of the gases source would be connected to, in turn, the dryline, the humidification chamber, and the inspiratory conduit. In a reverse flow condition such as shown in FIG. 2A, the outlet of the gases source would be connected to the expiratory conduit. The expiratory side, including, for example, a combination of the expiratory conduits, connectors, ports, and/or the like, has a lower resistance to flow than the inspiratory side, including for example, a combination of the dryline, the humidification chamber, and the inspiratory conduit. Optionally, the patient interface can be disconnected, for example, at an end of the wye-piece configured to be connected to the patient interface (for example, the patient interface connection port 66 as shown in FIG. 1A), when the resistance to flow is measured at the inspiratory side and/or the expiratory side. Alternatively, the patient interface and the wye-piece can be removed from the inspiratory and expiratory conduits. The patient ends of the inspiratory conduit and the expiratory conduit may be unimpeded as the gases source outputs gases at the known flow rate at step 2130. The resistance to flow measured at the inspiratory side or at the expiratory side corresponds to the inspiratory conduit or the expiratory conduit respectively, and is not influenced by different types of patient interfaces that are being used. Such a measurement of the resistance to flow can be more accurate.

At decision step 2134, the controller of the humidifier can communicate with the controller of the gases source to receive the measured resistance to flow value so as to compare the measured resistance to flow value to an expected resistance to flow value. The humidifier controller can store expected values, such as an expected resistance to flow value, corresponding to the identified tube in a memory of the humidifier controller.

If the measured resistance to flow value is less than the expected resistance to flow value, at step 2136, the controller of the humidifier can determine reverse flow is present. If the measured resistance to flow value is not less than the expected resistance to flow value, at step 2138, the controller of the humidifier can determine reverse flow is not present.

Alternatively, the tube identification steps 2124, 2126, 2128 can be performed by the controller of the gases source, which can detect connection of the tube connected to the inlet and outlet of the gases source. In this case, a communication between the controllers of the gases source and the humidifier may not be necessary to perform the method 2122 as the steps in method 2122 can be all performed by the controller of the gases source.

The controller of the system (for example, a controller of the gases source or a controller of the humidifier) may output a signal to a user interface to indicate to the user a presence of a reverse flow condition and/or incorrect connections within the system. The user interface may be the interface of the gases source or the humidifier. The user interface may be an audio visual device (for example, a touch screen or a series of indicator lights and a speaker or multiple screens). The indication of a reverse flow condition may be replicated on the humidifier screen, the gases source screen, and/or a user interface of a patient monitoring station, as the humidifier controller and gases source controller may be in electronic communication with one another. When a reverse flow condition is detected, the user can stop the humidifier via the gases source user interface (or humidifier user interface) and stop the gases source to correct the reverse flow condition.

Figure 22A:
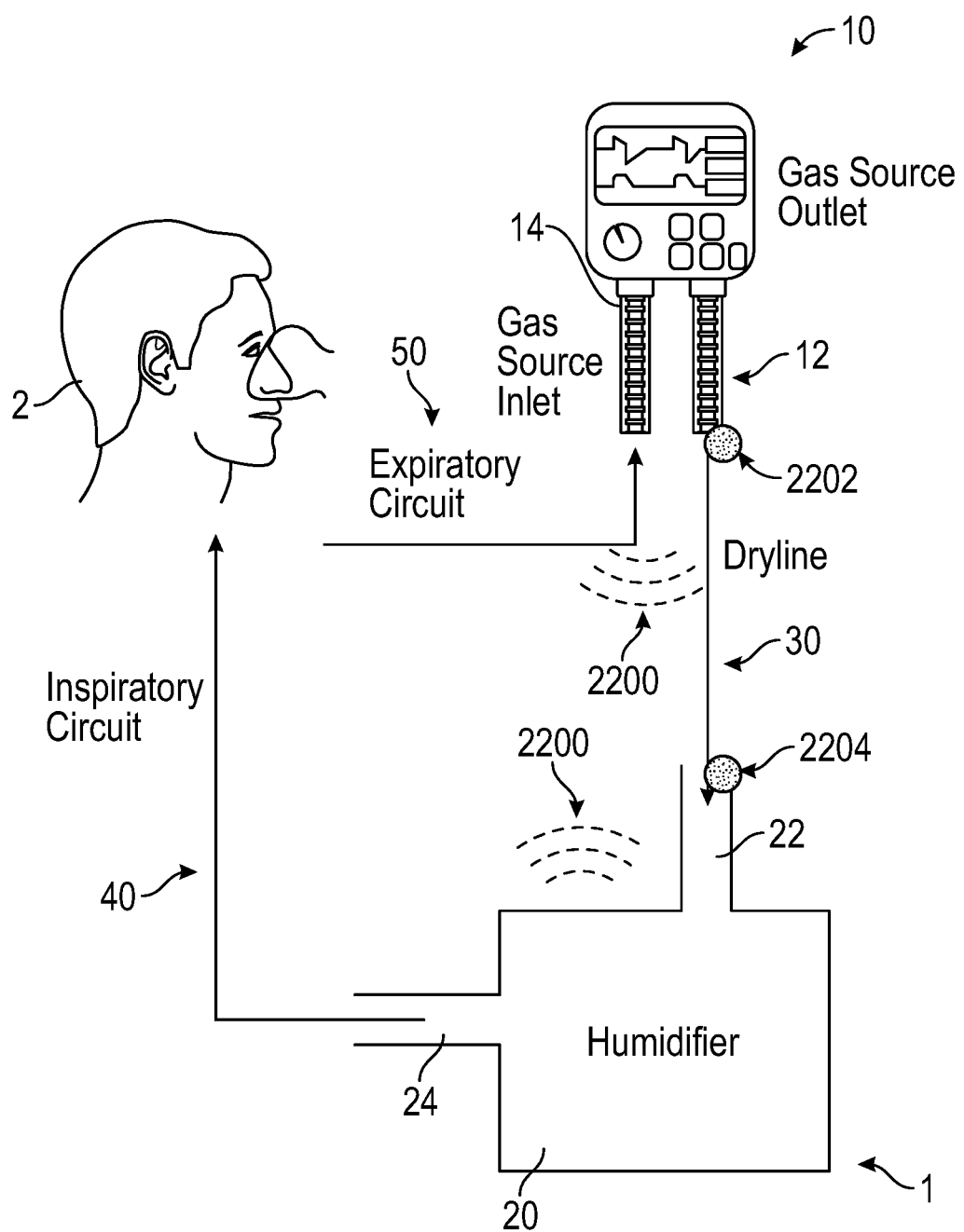
FIG. 22A illustrates an example humidification system configured to detect a reverse flow condition by comparing temperature differences at two ends of the dryline.

FIG. 22A illustrates a respiratory humidification system configured to monitor, under normal flow conditions, the temperature at the gases source outlet 12 using a first temperature sensor 2202 and the temperature at the humidification chamber inlet 22 using a second temperature sensor 2204. As disclosed herein, the connection between the gases source outlet 12 and the humidification chamber inlet 22 is established by the dryline 30. The dryline 30 is typically shorter than the expiratory conduit 50. Example lengths of the dryline can be between about 100 mm to about 1,000 mm, or between about 300 mm to about 900 mm, or between about 400 mm to about 800 mm, or between about 500 mm to about 800 mm, or between about 500 mm to about 600 mm, or between about 700 mm to about 800 mm. During normal flow conditions, the temperature of the gases coming out of the gases source outlet 12 at a first end of the dryline 30 can be substantially similar to or slightly higher than a standard ambient temperature. Assuming the ambient temperature is slightly lower than the temperature of the gases coming from the gases source outlet 12, the gases will cool very slightly as the gases travel through the dryline 30 towards the chamber inlet 22 at a second end of the dryline 30.

When the dryline 30 and the expiratory conduit 50 are switched during set up of the humidification system, such as shown in FIG. 2A, the first end of the dryline 30 can connect to the gases source inlet 14 and the second end of the dryline 30 can connect to the chamber inlet 22. The temperature difference between the first and second ends of the dryline 30 under this reverse flow condition can become reversed in polarity and the absolute temperature difference can be greater than in the normal flow condition. In this reverse condition, humidified gases travel from the chamber outlet 24 to the chamber inlet 22. After leaving the chamber 20 and entering the dryline 30, the humidified gases can cool down faster than the dry, cooler gas from the gases source 10 in the dryline 30, which does not have a heating element. The faster cooling is due to the greater difference between the temperature of the humidified gases leaving the chamber inlet 22 and the ambient temperature than the temperature difference between the cooler gas from the gases source 10 and the ambient temperature. Accordingly, the temperature at the chamber inlet 22 in the reverse flow condition can be much higher than the temperature at the gases source inlet 14. The temperature at the chamber inlet 22 in the reverse flow condition can also be much higher than the temperature at the gases source outlet 12.

The first temperature sensor 2202 can be located at the first end of the dryline 30 and the second temperature sensor 2204 can be located either at the second end of the dryline 30 or the chamber inlet 22. In this configuration, the first and second temperature sensors 2202, 2204 can be in electrical communication with the controller of the humidifier 20. There may be no communication between the controllers of the humidifier 20 and the gases source 10 related to the comparison of the temperature readings of the first and second temperature sensors 2202, 2204. Alternatively, the first temperature sensor 2202 can be located at the gases source outlet 12 and the second temperature sensor 2204 can be located either at the second end of the dryline 30 or the chamber inlet 22. In this alternative configuration, the first temperature sensor 2202 can be in electrical communication with the controller of the gases source 10 and the second temperature sensor 2204 can be in electrical communication with the controller of the humidifier 20. The controllers of the gases source 10 and the humidifier 20 can be in communication (for example, electrical and/or data communication) with each other so that one of the controllers of the gases source 10 or the humidifier 20 can compare the temperature readings of the first and second temperature sensors 2202, 2204.

Figure 22B:
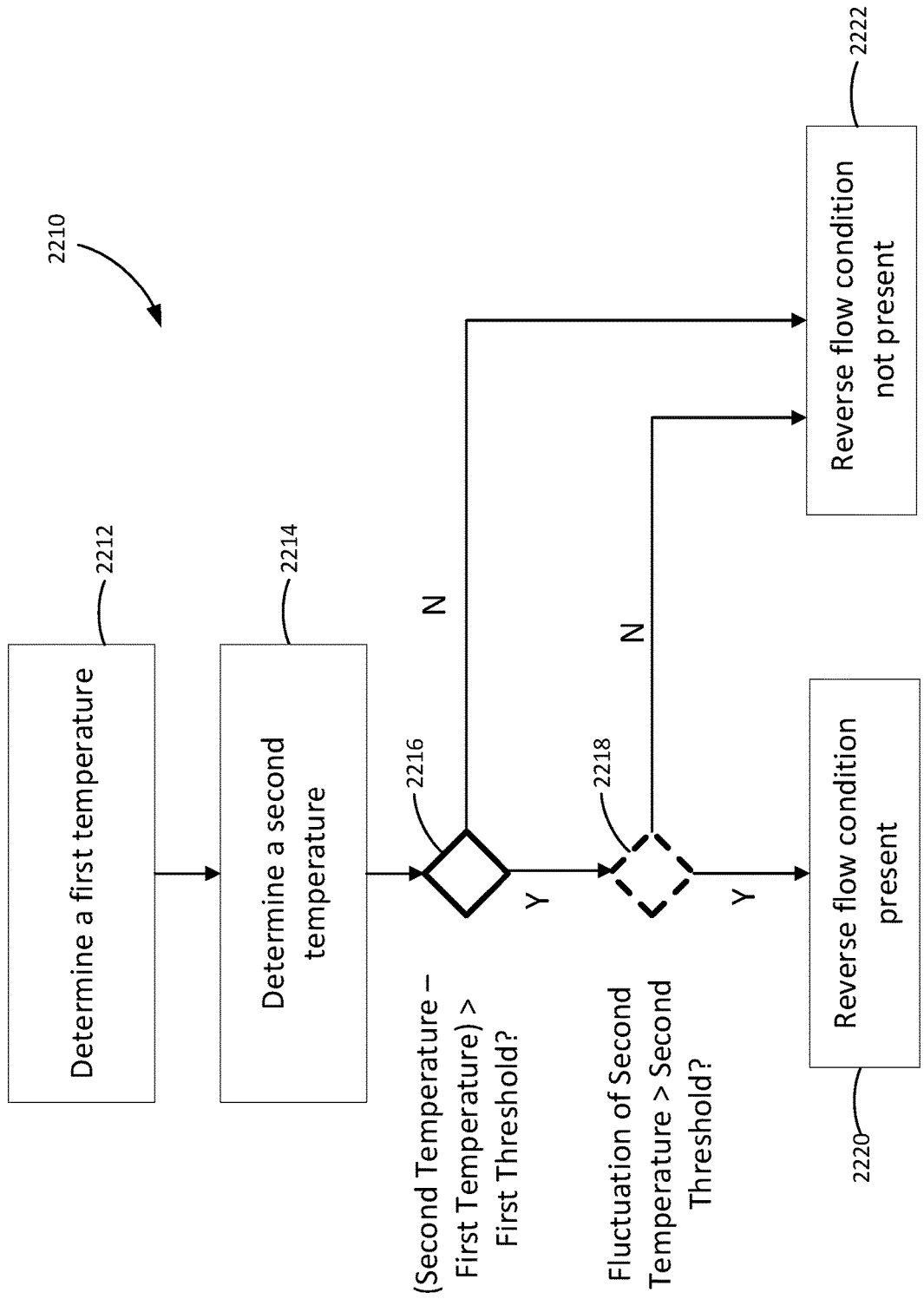
FIG. 22B illustrates another example method of detecting incorrect flow by monitoring temperature(s) at two ends of the dryline.

FIG. 22B illustrates an example method 2210 that compares temperature measurements from the first and second temperature sensors, which are, under normal flow conditions, indicative of temperatures at or near the outlet of the gases source and at or near the inlet of the humidification chamber. At step 2212, the control system (for example, a controller of the gases source or a controller of the humidifier) can determine a first temperature from the first sensor, which can be indicative of the temperature at or near the outlet of the gases source and/or at or near the first end of the dryline, depending on whether the system is under a normal flow condition or a reverse flow condition such as shown in FIG. 2A. At step 2214, the control system can determine a second temperature from the second sensor, which can be indicative of the temperature at or near the inlet of the chamber and/or at or near the second end of the dryline, depending on whether the system is under a normal flow condition or a reverse flow condition such as shown in FIG. 2A.

At decision step 2216, the control system can determine whether the second temperature is greater than the first temperature by a first threshold. The first threshold can be, for example, between about 0.1° C. to about 5° C., or between about 0.5° C. or about 4° C., or between about 1° C. to about 3° C. If the second temperature is higher than the first temperature by more than the first threshold, at step 2220, the control system can determine reverse flow is present. If the second temperature is not higher than the first temperature by more than the first threshold, at step 2220, the control system can determine reverse flow is not present.

At decision step 2218, the control system can optionally determine whether a fluctuation of the second temperature has exceeded a second threshold. The temperature fluctuation at the chamber inlet differs during the normal flow condition and during a reverse flow condition such as shown in FIG. 2A. The temperature fluctuation at the chamber inlet can be smaller during the normal flow condition than during the reverse flow condition such as shown in FIG. 2A. The greater fluctuation of the temperature at the chamber inlet is likely due to the heated and humidified gases flowing from the chamber outlet to the chamber inlet and/or the gases source pulsing the heated and humidified gases. If the fluctuation of the second temperature is higher than the second threshold, at step 2220, the control system can determine reverse flow is present. If the fluctuation of the second temperature does not exceed the second threshold, at step 2220, the control system can determine reverse flow is not present.

Wireless Sensors

The sensors described above may be wired or wireless (for example, utilizing Bluetooth, WiFi, RFID, Near Field Communication, or any other wireless communication protocols).

For example, when the sensor communicates with the controller via RFID, active and/or passive RFID tags may be used. Active tags would require a power source to function, whereas passive tags collect energy from a nearby RFID reader's interrogating radio waves. The RFID tags can be attached with different sensors, such as temperature, humidity, moisture, pressure, magnetic field, and the like.

The passive RFID tags may remove the need to design additional electrical connectors and a power source. It can be applied to consumables such as the expiratory tube, Y-piece, dryline, or otherwise for the purpose of reverse flow detection.

The wireless sensor(s) disclosed above can be in electronic communication with a controller. The controller can be a controller of the gases source or a controller of the humidifier. The controller can receive measurements from the wireless sensor(s) and process the received measurements. The controller can determine a reverse flow condition and/or indication of incorrect connections as described herein. The electrical communication can be wired or wireless.

Terminology

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "injecting a tracer" include "instructing injection of a tracer."

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A method of detecting reverse flow condition in a respiratory humidification system comprising a controller, a gases source, a humidifier, and a breathing circuit, the humidifier comprising a base comprising a heater plate and a humidification chamber that carries humidification fluid, the humidification chamber positionable on the base, the breathing circuit comprising an inspiratory conduit, an expiratory conduit, and a dryline, the method comprising:
    introducing a flow of gas into a humidification chamber inlet;
    directing the flow of gas via a flow guide coupled to the inlet towards a focused region of a surface of the humidification fluid;
    detecting a change in the surface of the humidification fluid; and
    outputting an indication of reverse flow condition based on the detected change in the surface of the humidification fluid.

2. The method of claim 1, wherein the focused region of the surface of the humidification fluid is directly underneath the humidification chamber inlet.

3. The method of claim 1, wherein the flow guide comprises an elongate tube that extends into the humidification chamber to cause the flow of gas to be directed onto the focused region.

4. The method of claim 1, wherein detecting the change in the surface comprises measuring a temperature of a humidification fluid surface below or adjacent the inlet of the humidification chamber, and wherein the temperature at the focused region being above a threshold temperature is indicative of a reverse flow condition.

5. The method of claim 4, wherein detecting the change in the surface comprises comparing a temperature at the focused region with a temperature at another area of the humidification fluid surface away from the focused region.

6. The method of claim 1, wherein detecting comprises monitoring a contour of a humidification fluid surface in the humidification chamber.

7. The method of claim 6, wherein monitoring the contour of the humidification fluid surface comprises monitoring a humidification fluid level at a first location and a humidification fluid level at a second location, wherein a difference between the first location and the second location not exceeding a threshold is indicative of a reverse flow condition.

8. The method of claim 7, wherein the first location is near the inlet of the humidification chamber and the second location is near an outlet of the humidification chamber.

9. The method of claim 7, wherein a preliminary step of establishing a baseline humidification fluid level at the first location or the second location is determined in an absence of the flow of gas.

10. The method of claim 6, wherein monitoring the contour of the humidification fluid surface is performed by an optical sensor.

11. The method of claim 1, wherein detecting a change in the surface of the humidification fluid comprises detecting a ripple pattern on the humidification fluid surface.

12. The method of claim 11, wherein the controller is configured to detect a ripple by comparing the detected ripple pattern with a predetermined ripple pattern or classifying the ripple pattern using an image or pattern recognition technique.

13. The method of claim 11, wherein the ripple pattern being detected is indicative of a normal flow condition, and the ripple pattern not being detected is indicative of a reverse flow condition.

14. The method of claim 11, wherein monitoring the ripple pattern is performed by an optical sensor.

15. The method of claim 1, wherein the respiratory humidification system is configured to deliver respiratory therapy to a patient, the system further comprises:
    a user interface;
    a first breathing circuit configured for connecting a gases source and the humidification chamber;
    a second breathing circuit configured for connecting the gases source and the patient, the first breathing circuit configured to be upstream of the second breathing circuit in a normal flow condition; and
    a reverse flow indicator located in a gases flow path of the system, wherein the reverse flow indicator is in a first configuration during normal flow and a second configuration different from the first configuration during reverse flow.

* * * * *